United States Patent
Sablon et al.

(10) Patent No.: US 7,196,183 B2
(45) Date of Patent: Mar. 27, 2007

(54) HEPATITIS C VIRUS GENOTYPE, AND ITS USE AS PROPHYLACTIC, THERAPEUTIC AND DIAGNOSTIC AGENT

(75) Inventors: Erwin Sablon, Merchtem (BE); Leen-Jan Van Doorn, Ridderkerk (NL); Wim Quint, Nootdorp (NL)

(73) Assignee: Innogenetics N.V., Ghent (BE)

(*) Notice: Subject to any disclaimer, the term of this patent is extended or adjusted under 35 U.S.C. 154(b) by 714 days.

(21) Appl. No.: 10/230,381

(22) Filed: Aug. 29, 2002

(65) Prior Publication Data

US 2003/0152591 A1   Aug. 14, 2003

Related U.S. Application Data

(60) Provisional application No. 60/345,642, filed on Jan. 8, 2002.

(30) Foreign Application Priority Data

Aug. 31, 2001 (EP) .................................. 01120969

(51) Int. Cl.
C07H 21/04 (2006.01)
C12P 19/34 (2006.01)
C12Q 1/70 (2006.01)

(52) U.S. Cl. .......................... 536/23.1; 435/91.4; 435/5

(58) Field of Classification Search ..................... None
See application file for complete search history.

(56) References Cited

U.S. PATENT DOCUMENTS

| | | | |
|---|---|---|---|
| 5,043,272 A | 8/1991 | Hartley | |
| 5,077,193 A | 12/1991 | Mishiro et al. | |
| 5,173,994 A | 12/1992 | Gillum et al. | |
| 5,176,994 A | 1/1993 | Mishiro et al. | |
| 5,252,743 A | 10/1993 | Barrett et al. | |
| 5,350,671 A | 9/1994 | Houghton et al. | |
| 5,372,928 A | 12/1994 | Miyamura et al. | |
| 5,427,909 A | 6/1995 | Okamoto et al. | |
| 5,428,145 A | 6/1995 | Okamoto et al. | |
| 5,514,539 A | 5/1996 | Bukh et al. | |
| 5,527,669 A | 6/1996 | Resnick et al. | |
| 5,550,016 A | 8/1996 | Okamoto | |
| 5,620,852 A | 4/1997 | Lin et al. | |
| 5,629,153 A | 5/1997 | Urdea | |
| 5,629,158 A | 5/1997 | Uhlen | |
| 5,820,852 A | 10/1998 | Burgess et al. | |
| 5,846,704 A | 12/1998 | Maertens et al. | |
| 5,871,903 A | 2/1999 | Miyamura et al. | |
| 5,882,852 A | 3/1999 | Bukh et al. | |
| 6,051,696 A | 4/2000 | Maertens et al. | |
| 6,171,784 B1* | 1/2001 | Maertens et al. | 435/5 |
| 6,190,864 B1 | 2/2001 | Cha et al. | |
| 6,297,370 B1 | 10/2001 | Cha et al. | |
| 6,416,946 B1 | 7/2002 | Chien et al. | |
| 6,495,670 B1 | 12/2002 | Maertens et al. | |
| 6,548,244 B2 | 4/2003 | Maertens et al. | |
| 6,762,024 B2 | 7/2004 | Maertens et al. | |

FOREIGN PATENT DOCUMENTS

| | | |
|---|---|---|
| EP | 0 435 229 | 7/1991 |
| EP | 0 461 863 | 12/1991 |
| EP | 0 463 848 | 1/1992 |
| EP | 0 469 348 | 2/1992 |
| EP | 0 510 952 | 10/1992 |
| EP | 0 511 559 | 11/1992 |
| EP | 0 532 167 | 3/1993 |
| EP | 0 408 918 | 11/1993 |
| EP | 0 318 216 | 12/1993 |
| EP | 0 529 493 | 12/1997 |
| EP | 0 531 974 | 12/1999 |
| EP | 0 419 182 | 1/2000 |
| EP | 0 388 232 | 1/2005 |
| GB | 2 239 245 | 6/1991 |
| JP | 04-179482 | 6/1992 |

(Continued)

OTHER PUBLICATIONS

Bukh, J. "Sequence analysis of the 5' noncoding region of hepatitis C virus" Proc. Natl. Acad. Sci. Jun. 1992, 89: 4942-4946.*

Jha, J. and Arankalle, V.A., Hepatitis C Virus Isolate NIV-10 5' Non-Coding Region. Sep. 2000, NCBI (PubMed), Nucleotide No. AF134759.*

Nagayama, et al., "Characteristics of hepatitis C viral genome associated with disease progression", Unpublished, Apr. 27, 2000, Database accession No. AF207756, XP002214568, Abstract.

Tokita, et al., "The entire nucleotide sequence of three hepatitis C virus isoleates in genetic groups 7-9 and comparison with those in the other eight genetic groups", Sep. 8, 1998, Database accession No. D84265, XP002214569; J. Gen. Virol., 79 (1998) 1847-1857.

Tokita, et al., "Heptatis C virus variants from Jakarta Indonesia classifiable into novel genotypes in the second (2e and 2f), tenth, (10a) and eleventh (11a) genetic groups", Database accession No. D63822, XP002214570, Abstract, J. Gen. Virol., vol. 77, 1996, pp. 293-301.

(Continued)

*Primary Examiner*—Bruce R. Campell
*Assistant Examiner*—Michelle Horning
(74) *Attorney, Agent, or Firm*—Nixon & Vanderhye P.C.

(57) ABSTRACT

The present invention relates to genomic nucleotide sequences and amino acid sequences corresponding to the non-coding and coding region of a new type of HCV. The invention relates to new HCV types and subtypes sequences which are different from the known HCV types and subtypes sequences. Particularly, the present invention relates to said new HCV type sequences; a process for preparing them, and their use for diagnosis, prophylaxis and therapy. More particularly, the present invention provides new type-specific sequences of the 5' NCR, Core, the E1 and the NS5 regions of the new HCV type. These new HCV sequences are useful to diagnose the presence of HCV type genotypes or serotypes in a biological sample. Moreover, the availability of these new type-specific sequences can increase the overall sensitivity of HCV detection and should also prove to be useful for prophylactic and therapeutic purposes.

27 Claims, 13 Drawing Sheets

FOREIGN PATENT DOCUMENTS

Figure 3A:
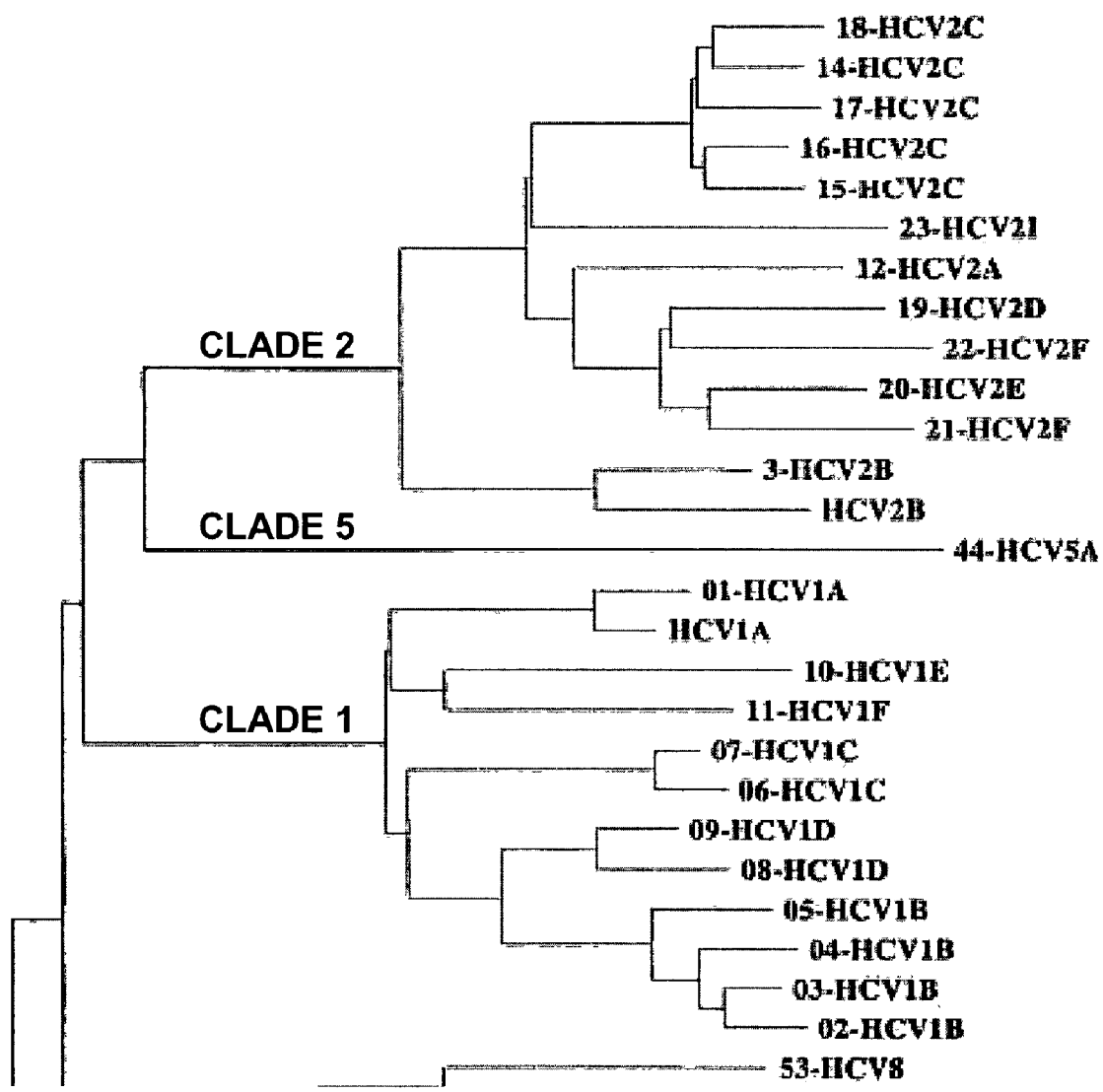

| | | |
|---|---|---|
| JP | 06-319563 | 11/1994 |
| WO | WO 89/10977 | 11/1989 |
| WO | WO 91/06674 | 5/1991 |
| WO | WO 91/14779 | 10/1991 |
| WO | WO 92/02642 | 2/1992 |
| WO | WO 92/10588 | 6/1992 |
| WO | WO 92/19743 | 11/1992 |
| WO | WO 93/00365 | 1/1993 |
| WO | WO 93/04088 | 3/1993 |
| WO | WO 03/06126 | 4/1993 |
| WO | WO 93/10239 | 5/1993 |
| WO | WO 93/23569 | 11/1993 |
| WO | WO 94/25601 | 11/1994 |
| WO | WO 95/01442 | 1/1995 |

OTHER PUBLICATIONS

Tokita, et al., "Hepatitis C virus variants from Vietnam are classifiable into the seventh, eigth and ninth major genetic groups", Database accession No. 89955, XP002214571, Abstract, Proc. Natl. Acad. Sci. USA, vol. 91, 1994, pp. 11022-11026.
Stuyver, et al., "hepatitis C genotyping by means of a 5'-UR/core line probe assays and molecular analysis of untypable samples", Virus Research, vol. 38, 1995, pp. 137-157, XP002057867.
Giannini, et al., "Comparative analysis of two assays for genotyping heptatitis C virus based on genotype-specific primers or probes", J. Hepatol., vol. 23, 1995, pp. 246-253, XP001104530.
Robertson, et al., "Classification, nomenclature and databse development for hepatitis C virus and related viruses: proposals for standardization", Arch. Virol., vol. 143, No. 12, 1998, pp. 24983-2503, XP001104551.
Apichartpiyakul et al, Journal of Clinical Microbiology, 1994, vol. 32, No. 9, pp. 2276-2279.
Bukh et al, Proc. Natl. Acad. Sci., 1992, vol. 89, pp. 4942-4946.
Bukh et al, Proc. Natl. Acad. Sci., 1993, vol. 90, pp. 8234-8238.
Bukh et al, Proc. Natl. Acad. Sci., 1994, vol. 91, pp. 8239-8243.
Castillo et al, Journal of Virological Methods, 1992, vol. 38, pp. 71-80.
Cha et al, Journal of Clinical Microbiology, 1991, vol. 29, pp. 2528-2534.
Cha et al, Proc. Natl. Acad. Sci., 1992, vol. 89, pp. 7144-7148.
Chan et al, Proc. Natl. Acad. Sci., 1979, vol. 76, No. 10, pp. 5036-5040.
Chan et al, Journal of General Virology, 1992, vol. 73, pp. 1131-1141.
Chayama et al, Journal of Gastroenterology and Hepatology, 1993, vol. 8, pp. 150-156.
Chen et al, Virology, 1992, vol. 188, pp. 102-113.
Choo et al, Proc. Natl. Acad. Sci., 1991, vol. 88, pp. 2451-2455.
Co et al, Proc. Natl. Acad. Sci., 1991, vol. 88, pp. 2869-2873.
Driesel et al, Arch Virol, 1994, vol. 139, pp. 379-388.
Enomoto et al, Biochemical and Biophysical Research Communications, 1990, vol. 170, No. 3, pp. 1021-1025.
Flores et al, Nucleic Acids Research, 1990, vol. 18, No. 4, pp. 901-911.
George et al, Macromolecular Sequencing and Synthesis Selected, Methods and Applications, 1988, pp. 127-149.
Halfon et al, Journal of Clinical Microbiology, 2001, vol. 39, No. 5, pp. 1771-1773.
Han et al, Proc. Natl. Acad. Sci., 1991, vol. 88, pp. 1711-1715.
Horie et al, J. Biochem., 1989, vol. 106, pp. 1-4.
Hotta et al, Journal of Clinical Microbiology, 1994, vol. 32, No. 12, pp. 3049-3051.
Hu et al, Journal of Clinical Investigation, 1992, vol. 89, pp. 2040-2045.
Inchauspe et al, Hepatology, 1991, vol. 14, pp. 595-600.
Innis et al, In "PCR protocols. A guide to methods and applications", 1990, pp. 1-12.
Kato et al, Proc. Natl. Acad. Sci., 1990, vol. 87, pp. 9524-9528.
Kennell, Progr. Nucl. Acid Res. Mol. Biol., 1971, vol. 11, pp. 259-301.
Lee et al, Journal of Clinical Microbiology, 1992, vol. 30, No. 6, pp. 1602-1604.
Liu et al, Gene, 1992, vol. 114, pp. 245-250.
Majzoub et al, The Journal of Biological Chemistry, 1983, vol. 258, No. 23, pp. 14061-14064.
Martell et al, Journal of Virology, 1992, vol. 66, No. 5, pp. 3225-3229.
Meyerhans et al, Nucleic Acids Research, 1992, vol. 20, No. 3, pp. 521-523.
Mori et al, Biochem Biophys Res Commun, 1992, vol. 183, pp. 334-342.
Nakao et al, J Gen Virol, 1991, vol. 72, pp. 2105-2112.
Nedjar et al, Journal of Virological Methods, 1991, vol. 35, pp. 297-304.
Ogata et al, Proc. Natl. Acad. Sci., 1991, vol. 88, pp. 3392-3396.
Okamoto et al, Japan J. Exp. Med., 1990, vol. 60 No. 3, pp. 167-177.
Okamoto et al, Journal of General Virology, 1991, vol. 72, pp. 2697-2704.
Okamoto et al, Journal of General Virology, 1992, vol. 73, pp. 673-679.
Okamoto et al, Virology, 1992, vol. 188, pp. 331-341.
Qu et al, Journal of General Virology, 1994, vol. 75, pp. 1063-1070.
Rosel et al, Journal of Virology, 1985, vol. 56, No. 3, pp. 830-838.
Shuldiner et al, The Journal of Biological Chemistry, 1989, vol. 264, No. 16, pp. 9428-9432.
Simmonds et al, Journal of Clinical Microbiology, 1993, vol. 31, No. 6, pp. 1493-1503.
Simmonds et al, Journal of General Virology, 1993, vol. 74, pp. 661-668.
Sommer et al, Nucleic Acids Research, 1989, vol. 17, p. 8749.
Stratagene Catalog 1988, p. 39.
Stuyver et al, Biochemical and Biophysical Research Communications, 1993, vol. 192, No. 2, pp. 635-641.
Stuyver et al, Journal of Virology, 1993, vol. 74, pp. 1093-1102.
Stuyver et al, Proc. Natl. Acad. Sci., 1994, vol. 91, pp. 10134-10138.
Takamizawa et al, Journal of Virology, 1991, vol. 65, No. 3, pp. 1105-1113.
van Doorn et al, Journal of General Virology, 1995, vol. 76, pp. 1871-1876.
van Doorn et al, Journal of Hepatology, 1994, vol. 21, pp. 122-129.
Wallace et al, Methods in Enzymology, 1987, vol. 152, pp. 432-442.
Weiner et al, Lancet, 1990, vol. 335, pp. 1-3.
Weiner et al, Virology, 1991, vol. 180, pp. 842-848.
Williams et al, Biochemistry, 1992, vol. 31, pp. 9768-9776.
Yuan et al, Proc. Natl. Acad. Sci., 1983, vol. 80, pp. 1169-1173.
US 6,180,768, 01/2001, Maertens et al. (withdrawn)

\* cited by examiner

SEQ ID NO:1

```
 31          40          50          60          70          80
            -290        -280        -270        -260        -250
 |           |           |           |           |           |
CCCTGTGAGG  AACTACTGTC  TTCACGCAGA  AAGCGTCTAG  CCATGGCGTT 81          90         100         110         120         130
            -240        -230        -220        -210        -200
 |           |           |           |           |           |
AGTATGAGTG  TCGTGCAGCC  TCCAGGACCC  CCCCTCCCGG  GAGAGCCATA 131         140         150         160         170         180
            -190        -180        -170        -160        -150
 |           |           |           |           |           |
GTGGTCTGCG  GAACCGGTGA  GTACACCGGA  ATTGCCAGGA  AGACCGGGTC 181         190         200         210         220         230
            -140        -130        -120        -110        -100
 |           |           |           |           |           |
CTTTCTTGGA  TTAACCCGCT  CTATGCCTGG  TCATTTGGGC  GTGCCCCGC 231         240         250         260         270         280
             -90         -80         -70         -60         -50
 |           |           |           |           |           |
GAGACTGCTA  GCCGAGTAGT  GTTGGGTCGC  GAAAGGCCTT  GTGGTACTGC 281         290         300         310         320         329
             -40         -30         -20         -10          -1
 |           |           |           |           |           |
CTGATAGGGT  GCTTGCGAGT  GCCCCGGGAG  GTCTCGTAGA  CCGTGCACC
```

FIGURE 1A

SEQ ID NO:2

```
ATGAGCACGA ATCCTAAACC TCAAAGACAA ACCAAAAGAA ACACCAACCG
TTNCCCTAAG GATATTAAGT TCCCGGGCGG CGGACAGATC GTTGGTGGAG
TTTACTTGTT ACCACGCAGG GGCCCACGAT TGGGTGTGCG TGCGGCGAGG
AAGGCTTCCG AGCGATCGGA GCCGCGGAGT AAACGTCAGC GTATTCCAAA
GGCTCGCCAG CCTACGGGCC GGCATTGGGG TCAACCCGGT TACCCATGGC
CCCTCTACGG CAACGAGGGC TGCGGTTGGG CAGGATGGCT CCTGTCCCCC
CGCGGCTCTC GGCCAAGTTG GGGCCCAAT GACCCACGGC GTAGGTCACG
CAATTTGGGT AAGGTCATCG ATACCCTAAC GTGTGGCCTC GCCGACCTCT
TTGGGTACAT CCCTGTTGTC GGCGGACCGC TTGGCGGTGT CGCGGCAGCG
CTGGCGCATG GCGTCAGGGC TGTTGAAGAC GGGATTAATT ATGCAACGGG
GAATTTGCCC GGTTGCTCCT TTTCTATCTT CCTCTTAGCT CTTCTCTCAT
GCCTCACTGT ACCTGCTTCA GCTGTCCCCT ATGCTAATAA GTCTGGTATT
TACCATCTTA CCAACGACTG TCCTAATT
```

SEQ ID NO:3

```
MSTNPKPQRQ TKRNTNRXPK DIKFPGGGQI VGGVYLLPRR GPRLGVRAAR
KASERSEPRS KRQRIPKARQ PTGRHWGQPG YPWPLYGNEG CGWAGWLLSP
RGSRPSWGPN DPRRRSRNLG KVIDTLTCGL ADLFGYIPVV GGPLGGVAAA
LAHGVRAVED GINYATGNLP GCSFSIFLLA LLSCLTVPAS AVPYANKSGI
YHLTNDCPN
```

SEQ ID NO:4

```
ATGAGCACGA ATCCTAAACC TCAAAGACAA ACCAAAAGAA ACACCAACCG
TCGCCCTAAG GATATTAAGT TCCCGGGCGG CGGACAGATC GTTGGTGGAG
TTTACTTGGT ACCACGCAGG GGCCCACGAT TGGGTGTGCG TGCGGCGAGG
AAGACTTCCG AGCGATCGGA GCCGCGGAGT AAACGTCAGC GTATTCCAAA
GGCTCGCCAG CCTACGGGCC GGCACTGGGG TCAACCCGGT TACCCATGGC
CCCTCTACGG CAACGAGGGC TGCGGTTGGG CAGGATGGCT CCTGTCCCCC
CGCGGCTCTC GGCCAAGTTG GGGCCCAAT GACCCACGGC GTAGGTCACG
CAATTTGGGT AAGGTCATCG ATACCCTAAC GTGTGGCCTC GCCGACCTCT
TTGGGTACAT CCCTGTCGTC GGCGGACCGC TTGGCGGTGT CGCGGCAGCG
CTGGCGCATG GCGTCAGGGC TGTTGAGGAC GGGA
```

FIGURE 1B

SEQ ID NO:5

MSTNPKPQRQ TKRNTNRRPK DIKFPGGGQI VGGVYLVPRR GPRLGVRAAR
KTSERSEPRS KRQRIPKARQ PTGRHWGQPG YPWPLYGNEG CGWAGWLLSP
RGSRPSWGPN DPRRRSRNLG KVIDTLTCGL ADLFGYIPVV GGPLGGVAAA
LAHGVRAVED G

SEQ ID NO:6

ATGAGCACGA ATCCTAAACC TCAAAGACAA ACCAAAAGAA ACACCAACCG
TCGCCCTAAG GATATTAAGT TCCCGGGCGG CGGACAGATC GTTGGTGGAG
TTTACTTGTT ACCACGCAGG GGCCCACGAT TGGGTGTGCG TGCGGCGAGG
AAGACTTCCG AGCGATCGGA GCCGCGGAGT AAACGTCAGC GTATTCCAAA
GGCTCGCCAG CCTACGGGCC GGCACTGGGG TCAACCCGGT TACCCATGGC
CCCTCTACGG CAACGAGGGC TGCGGTTGGG CAGGATGGCT CCTGTCCCCC
CGCGGCTCTC GGCCAAGTTG GGGCCCAAT GACCCACGGC GTAGGTCACG
CAATTTGGGT AAGGTCATCG ATACCCTAAC GTGTGGCCTC GCCGACCTCT
TTGGGTACAT CCCTGTCGTC GGCGGACCGC TTGGCGGTGT CGCGGCAGCG
CTGGCGCATG GCGTCAGGGC TGTTGAGGAC GGGATTAATT ATGCAACGGG
GAATTTGCCC GGTTGCTCCT TTTCTATCTT CCTCTTAGCT CTTCTCTCAT
GCCTCACTGT ACCTGCTTCA GCTGTCCCCT ATGCTAATAA GTCTGGTATT
TACCATCTTA CCAACGACTG TCCTAATT

SEQ ID NO:7

MSTNPKPQRQ TKRNTNRRPK DIKFPGGGQI VGGVYLLPRR GPRLGVRAAR
KTSERSEPRS KRQRIPKARQ PTGRHWGQPG YPWPLYGNEG CGWAGWLLSP
RGSRPSWGPN DPRRRSRNLG KVIDTLTCGL ADLFGYIPVV GGPLGGVAAA
LAHGVRAVED GINYATGNLP GCSFSIFLLA LLSCLTVPAS AVPYANKSGI
YHLTNDCPN

FIGURE 1C

SEQ ID NO:8

```
8267      8276         8286         8296         8306         8316
 |         |            |            |            |            |
CGTTACCGAA AGAGACATTC GTACCGAGGA GTCCATTTAC CAATCATGCC
8317      8326         8336         8346         8356         8366
 |         |            |            |            |            |
AGCTCGACCC GGTTGCCCGG AAAGCAATTA CATCGCTTAC CGAGAGGCTG
8367      8376         8386         8396         8406         8416
 |         |            |            |            |            |
TATGTGGGAG GCCCTATGTT CAACTCTAGG GGCGAGCCCT GCGGTTACCG
8417      8426         8436         8446         8456         8466
 |         |            |            |            |            |
CAGGTGCCGC GCTAGTGGGG TCCTACCCAC CAGCATGGGT AACACCATCA
8467      8476         8486         8496         8506         8516
 |         |            |            |            |            |
CATGCTACCT CAAGGCTACA GCCGCATGCC GAGCAGCCGG ACCCATGGAC
8517      8526         8536         8546         8556         8566
 |         |            |            |            |            |
CTTGACATGC TCGTGTGTGG GGACGACTTG GTGGTCATCT CGGAGAGCGC
8567      8576         8586
 |         |            |
GGGTACGGCT GATGATGCAG CTGC
```

SEQ ID NO:9

```
2647      2656         2666         2676         2686         2696
 |         |            |            |            |            |
VTERDIRTEE SIYQSCQLDP VARKAITSLT ERLYVGGPMF NSRGEPCGYR
2697      2706         2716         2726         2736         2746
 |         |            |            |            |            |
RCRASGVLPT SMGNTITCYL KATAACRAAG PMDLDMLVCG DDLVVSRRAR
2747
 |
VRLMMQL
```

FIGURE 1D

```
                    1         10         20         30         40
                    |          |          |          |          |
SEQ ID NO:11  MSTNPKPQRQ TKRNTN RRPK  DIKFPGGGQI VGGVYLLPRR
SEQ ID NO:13  ---------- ------ ----  ---------- ------V---
SEQ ID NO:15  ---------- ------ ----  ---------- ----------
SEQ ID NO:3   ---------- ------ -X--  ---------- ----------
SEQ ID NO:7   ---------- ------ ----  ---------- ----------
SEQ ID NO:5   ---------- ------ ----  ---------- ------V---

41         50         60         70         80
                    |          |          |        ***  ******** |
SEQ ID NO:11  GPRLGVRAAR KTSERSEPRS KRQRIPKARQ PTGRHWGQPG
SEQ ID NO:13  ---------- ---------- ---------- ----------
SEQ ID NO:15  ---------- -A-------- ---------- ----------
SEQ ID NO:3   ---------- -A-------- ---------- ----------
SEQ ID NO:7   ---------- ---------- ---------- ----------
SEQ ID NO:5   ---------- ---------- ---------- ----------

81         90        100        110        120
                    |          |          |          |          |
SEQ ID NO:11  YPWPLYGNEG CGWAGWLLSP RGSRPSWGPN DPRRRSRNLG
SEQ ID NO:13  ---------- ---------- ---------- ----------
SEQ ID NO:15  ---------- ---------- ---------- ----------
SEQ ID NO:3   ---------- ---------- ---------- ----------
SEQ ID NO:7   ---------- ---------- ---------- ----------
SEQ ID NO:5   ---------- ---------- ---------- ----------

121        130        140        150        160
                    |          |          |          |          |
SEQ ID NO:11  KVIDTLTCGL ADLFGYIPVV GGPLGGVAAA LAHGVRAVED
SEQ ID NO:13  ---------- ---------- ---------- ----------
SEQ ID NO:15  ---------- ---------- ---------- ----------
SEQ ID NO:3   ---------- ---------- ---------- ----------
SEQ ID NO:7   ---------- ---------- ---------- ----------
SEQ ID NO:5   ---------- ---------- ---------- ----------

161        170        180        190        200
                    |          |          |          |   ++++++++
SEQ ID NO:11  GINYATGNLP GCSFSIFLLA LLSCLTVPAS A VPYANKSGI
SEQ ID NO:13  ---------- ---------- ---------- - ---------
SEQ ID NO:15  ---------- ---------- ---------- - ---------
SEQ ID NO:3   ---------- ---------- ---------- - ---------
SEQ ID NO:7   ---------- ---------- ---------- - ---------
SEQ ID NO:5   -
```

FIGURE 2A

```
              201        210          220        230         240
              +++         |      ########  ###     ^  ^^^^^^^^^^
SEQ ID NO:11  YHLTNDCPN S SIIYEAEDII MHMPGCVPCV LVGNISRCWV
SEQ ID NO:13  ---------  - ---------- ---------- ----------
SEQ ID NO:15  ---------  - ---------- ---------- ----------
SEQ ID NO:3   ---------
SEQ ID NO:7   ---------
              241        250          260        270         280
              ^^         @@@ @@@@@@@    |          |           |
SEQ ID NO:11  PASPTLAIPN ASVPVRSFRK HVDLLVGAAA LCSAMYVGDL
SEQ ID NO:13  ---------- ---------- ---------- ----------
SEQ ID NO:15  ---------- ---------- ---------- ----------
              281        290          300        310         320
               |          |       SSSSSSS SSS     |           |
SEQ ID NO:11  CGGVFLVGQL ISYRPRQHAT VQDCNCSIYA GHVTGHRMAW
SEQ ID NO:13  ---------- ---------- ---------- ----------
SEQ ID NO:15  ---------- ---------- ---------- ----------
              321        330          340        350         360
               |          ! !!!!!!!!!! !!         |           |
SEQ ID NO:11  DMMMNWSPTV TYLVSSILRI PQILIDIFVG GHWGVIGAVL
SEQ ID NO:13  ---------- ---------- ---------- ----------
SEQ ID NO:15  ---------- ---------- ---------- ----------
              361        370
               |          |
SEQ ID NO:11  FYSMQANWAK VIC
SEQ ID NO:13  ---------- ---
SEQ ID NO:15  ---------- ---
```

FIGURE 2B

```
                         323        332        342        352        362
                          |          |          |          |          |
SEQ ID NO:10  GTGCACCATG AGCACGAATC CTAAACCTCA AAGACAAACC
SEQ ID NO:12  ---------- ---------- ---------- ----------
SEQ ID NO:14  ---------- ---------- ---------- ----------
SEQ ID NO:2              ---        ---------- ---------- ----------
SEQ ID NO:4              ---        ---------- ---------- ----------
SEQ ID NO:6              ---        ---------- ---------- ----------
                         363        372        382        392        402
                          |          |          |          |          |
SEQ ID NO:10  AAAAGAAACA CCAACCGTCG CCCTAAGGAT ATTAAGTTCC
SEQ ID NO:12  ---------- ----|----- ---------- ----------
SEQ ID NO:14  ---------- ----|----- ---------- ----------
SEQ ID NO:2   ---------- ----|--TN  ---------- ----------
SEQ ID NO:4   ---------- ----|----- ---------- ----------
SEQ ID NO:6   ---------- ----|----- ---------- ----------
                         403        412        422        432        442
                          |          |          |          |          |
SEQ ID NO:10  CGGGCGGCGG ACAGATCGTT GGTGGAGTTT ACTTGTTACC
SEQ ID NO:12  ---------- ---------- ---------- -----G----
SEQ ID NO:14  ---------- ---------- ---------- ----------
SEQ ID NO:2   ---------- ---------- ---------- ----------
SEQ ID NO:4   ---------- ---------- ---------- -----G----
SEQ ID NO:6   ---------- ---------- ---------- ----------
                         443        452        462        472        482
                          |          |          |          |          |
SEQ ID NO:10  ACGCAGGGGC CCACGATTGG GTGTGCGTGC GGCGAGGAAG
SEQ ID NO:12  ---------- ---------- ---------- ----------
SEQ ID NO:14  ---------- ---------- ---------- ----------
SEQ ID NO:2   ---------- ---------- ---------- ----------
SEQ ID NO:4   ---------- ---------- ---------- ----------
SEQ ID NO:6   ---------- ---------- ---------- ----------
                         483        492        502        512        522
                          |          |          |          |          |
SEQ ID NO:10  ACTTCCGAGC GATCGGAGCC GCGGAGTAAA CGTCAGCGTA
SEQ ID NO:12  ---------- ---------- ---------- ----------
SEQ ID NO:14  G--------- ---------- ---------- ----------
SEQ ID NO:2   G--------- ---------- ---------- ----------
SEQ ID NO:4   ---------- ---------- ---------- ----------
SEQ ID NO:6   ---------- ---------- ---------- ----------
```

FIGURE 4A

```
                   523        532         542         552         562
                    |          |           |           |           |
SEQ ID NO:10   TTCCAAAGGC TCGCCAGCCT ACGGGCCGGC ACTGGGGTCA
SEQ ID NO:12   ---------- ---------- ---------- ----------
SEQ ID NO:14   ---------- ---------- ---------- -T--------
SEQ ID NO:2    ---------- ---------- ---------- -T--------
SEQ ID NO:4    ---------- ---------- ---------- ----------
SEQ ID NO:6    ---------- ---------- ---------- ----------

563        572         582         592         602
                    |          |           |           |           |
SEQ ID NO:10   ACCCGGTTAC CCATGGCCCC TCTACGGCAA CGAGGGCTGC
SEQ ID NO:12   ---------- ---------- ---------- ----------
SEQ ID NO:14   ---------- ---------- ---------- ----------
SEQ ID NO:2    ---------- ---------- ---------- ----------
SEQ ID NO:4    ---------- ---------- ---------- ----------
SEQ ID NO:6    ---------- ---------- ---------- ----------

603        612         622         632         642
                    |          |           |           |           |
SEQ ID NO:10   GGTTGGGCAG GATGGCTCCT GTCCCCCCGC GGCTCTCGGC
SEQ ID NO:12   ---------- ---------- ---------- ----------
SEQ ID NO:14   ---------- ---------- ---------- ----------
SEQ ID NO:2    ---------- ---------- ---------- ----------
SEQ ID NO:4    ---------- ---------- ---------- ----------
SEQ ID NO:6    ---------- ---------- ---------- ----------

643        652         662         672         682
                    |          |           |           |           |
SEQ ID NO:10   CAAGTTGGGG CCCCAATGAC CCACGGCGTA GGTCACGCAA
SEQ ID NO:12   ---------- ---------- ---------- ----------
SEQ ID NO:14   ---------- ---------- ---------- ----------
SEQ ID NO:2    ---------- ---------- ---------- ----------
SEQ ID NO:4    ---------- ---------- ---------- ----------
SEQ ID NO:6    ---------- ---------- ---------- ----------

683        692         702         712         722
                    |          |           |           |           |
SEQ ID NO:10   TTTGGGTAAG GTCATCGATA CCCTAACGTG TGGCCTCGCC
SEQ ID NO:12   ---------- ---------- ---------- ----------
SEQ ID NO:14   ---------- ---------- ---------- ----------
SEQ ID NO:2    ---------- ---------- ---------- ----------
SEQ ID NO:4    ---------- ---------- ---------- ----------
SEQ ID NO:6    ---------- ---------- ---------- ----------
```

FIGURE 4B

```
                 723        732        742        752        762
                  |          |          |          |          |
SEQ ID NO:10  GACCTCTTTG GGTACATCCC TGTCGTCGGC GGACCGCTTG
SEQ ID NO:12  ---------- ---------- ---------- ----------
SEQ ID NO:14  ---------- ---------- ---T------ ----------
SEQ ID NO:2   ---------- ---------- ---T------ ----------
SEQ ID NO:4   ---------- ---------- ---------- ----------
SEQ ID NO:6   ---------- ---------- ---------- ----------

763        772        782        792        802
                  |          |          |          |          |
SEQ ID NO:10  GCGGTGTCGC GGCAGCGCTG GCGCATGGCG TCAGGGCTGT
SEQ ID NO:12  ---------- ---------- ---------- ----------
SEQ ID NO:14  ---------- ---------- ---------- ----------
SEQ ID NO:2   ---------- ---------- ---------- ----------
SEQ ID NO:4   ---------- ---------- ---------- ----------
SEQ ID NO:6   ---------- ---------- ---------- ----------

803        812        822        832        842
                  |          |          |          |          |
SEQ ID NO:10  TGAGGACGGG ATTAATTATG CAACGGGGAA TTTGCCCGGT
SEQ ID NO:12  ---------- ---------- ---------- ----------
SEQ ID NO:14  ---A------ ---------- ---------- ----------
SEQ ID NO:2   ---A------ ---------- ---------- ----------
SEQ ID NO:4   ---------- -
SEQ ID NO:6   ---------- ---------- ---------- ----------

843        852        862        872        882
                  |          |          |          |          |
SEQ ID NO:10  TGCTCCTTTT CTATCTTCCT CTTAGCTCTT CTCTCATGCC
SEQ ID NO:12  ---------- ---------- ---------- ----------
SEQ ID NO:14  ---------- ---------- ---------- ----------
SEQ ID NO:2   ---------- ---------- ---------- ----------
SEQ ID NO:6   ---------- ---------- ---------- ----------

883        892        902        912        922
                  |          |          |          |          |
SEQ ID NO:10  TCACTGTACC TGCTTCAGCT GTCCCTATG CTAATAAGTC
SEQ ID NO:12  ---------- ---------- ---------- ----------
SEQ ID NO:14  ---------- ---------- ---------- ----------
SEQ ID NO:2   ---------- ---------- ---------- ----------
SEQ ID NO:6   ---------- ---------- ---------- ----------
```

FIGURE 4C

```
              923       932        942        952         962
               |         |          |          |           |
SEQ ID NO:10  TGGTATTTAC CATCTTACCA ACGACTGTCC TAATTCCAGC
SEQ ID NO:12  ---------- ---------- -------C-- ----------
SEQ ID NO:14  ---------- ---------- ---------- ----------
SEQ ID NO:2   ---------- ---------- ---------- ----------
SEQ ID NO:6   ---------- ---------- ---------- ----------

963       972        982        992        1002
               |         |          |          |           |
SEQ ID NO:10  ATCATTTATG AAGCCGAGGA CATCATCATG CACATGCCCG
SEQ ID NO:12  ---------- ---------- ---------- ----------
SEQ ID NO:14  ---------- ---------- ---------- ----------

1003      1012       1022       1032        1042
               |         |          |          |           |
SEQ ID NO:10  GTTGTGTTCC GTGCGTGTTG GTTGGCAACA TCTCTCGATG
SEQ ID NO:12  ---------- ---------- ---------- ----------
SEQ ID NO:14  ---------- ---------- ---------- ----------

1043      1052       1062       1072        1082
               |         |          |          |           |
SEQ ID NO:10  CTGGGTCCCT GCCTCCCCCA CCTTGGCCAT TCCTAACGCG
SEQ ID NO:12  ---------- ---------- ---------- ----------
SEQ ID NO:14  ---------- ---------- ---------- ----------

1083      1092       1102       1112        1122
               |         |          |          |           |
SEQ ID NO:10  AGCGTCCCGG TGCGGAGCTT CCGCAAGCAT GTGGATCTTC
SEQ ID NO:12  ---------- ---------- ---------- ----------
SEQ ID NO:14  ---------- ---------- ---------- ----------

1123      1132       1142       1152        1162
               |         |          |          |           |
SEQ ID NO:10  TCGTCGGGGC TGCTGCGCTT TGCTCGGCCA TGTACGTGGG
SEQ ID NO:12  ---------- ---------- ---------- ----------
SEQ ID NO:14  ---------- ---------- ---------- ----------

1163      1172       1182       1192        1202
               |         |          |          |           |
SEQ ID NO:10  TGATCTTTGC GGTGGTGTCT TCTTGGTCGG TCAACTGATT
SEQ ID NO:12  ---------- -----C---- ---------- ----------
SEQ ID NO:14  ---------- ---------- ---------- ----------
```

FIGURE 4D

```
              1203       1212       1222       1232       1242
                |          |          |          |          |
SEQ ID NO:10  AGTTATCGGC CGCGACAGCA CGCTACTGTG CAAGATTGCA
SEQ ID NO:12  ---------- ---------- ---------- ----------
SEQ ID NO:14  ---------- ---------- ---------- ----------
              1243       1252       1262       1272       1282
                |          |          |          |          |
SEQ ID NO:10  ACTGCTCCAT CTACGCGGGC CATGTTACTG GTCATCGTAT
SEQ ID NO:12  ---------- ---------- ---------- ----------
SEQ ID NO:14  ---------- ---------- ---------- ----------
              1283       1292       1302       1312       1322
                |          |          |          |          |
SEQ ID NO:10  GGCGTGGGAC ATGATGATGA ATTGGTCGCC GACTGTAACG
SEQ ID NO:12  ---------- ---------- ---------- ----------
SEQ ID NO:14  ---------- ---------- ---------- ----------
              1323       1332       1342       1352       1362
                |          |          |          |          |
SEQ ID NO:10  TACCTTGTGT CCAGCATTCT CAGGATACCC CAGATCTTAA
SEQ ID NO:12  ---------- ---------- ---------- ----------
SEQ ID NO:14  ---------- ---------- ---------- ----------
              1363       1372       1382       1392       1402
                |          |          |          |          |
SEQ ID NO:10  TTGACATCTT TGTTGGTGGC CACTGGGGAG TCATAGGAGC
SEQ ID NO:12  ---------- ---------- ---------- ----------
SEQ ID NO:14  ---------- ---------- ---------- ----------
              1403       1412       1422       1432       1442
                |          |          |          |          |
SEQ ID NO:10  TGTCTTGTTT TACTCCATGC AGGCCAACTG GGCCAAGGTG
SEQ ID NO:12  ---------- ---------- ---------- ----------
SEQ ID NO:14  ---------- ---------- ---------- ----------
              1443
                |
SEQ ID NO:10  ATCTGT
SEQ ID NO:12  ------
SEQ ID NO:14  ------
```

FIGURE 4E

SEQUENCE LISTING

<160> NUMBER OF SEQ ID NOS: 63

<210> SEQ ID NO 1
<211> LENGTH: 299
<212> TYPE: DNA
<213> ORGANISM: hepatitis C virus

<400> SEQUENCE: 1
ccctgtgagg aactactgtc ttcacgcaga aagcgtctag ccatggcgtt agtatgagtg    60
tcgtgcagcc tccaggaccc ccctcccgg gagagccata gtggtctgcg aaccggtga    120
gtacaccgga attgccagga agaccgggtc ctttcttgga ttaacccgct ctatgcctgg   180
tcatttgggc gtgccccgc gagactgcta gccgagtagt gttgggtcgc gaaaggcctt   240
gtggtactgc ctgatagggt gcttgcgagt gccccgggag gtctcgtaga ccgtgcacc    299

<210> SEQ ID NO 2
<211> LENGTH: 628
<212> TYPE: DNA
<213> ORGANISM: Hepatitis C virus
<220> FEATURE:
<221> NAME/KEY: misc_feature
<222> LOCATION: (53)..(53)
<223> OTHER INFORMATION: n is any nucleotide

<400> SEQUENCE: 2
atgagcacga atcctaaacc tcaaagacaa accaaaagaa acaccaaccg ttnccctaag    60
gatattaagt tcccgggcgg cggacagatc gttggtggag tttacttgtt accacgcagg   120
ggcccacgat tgggtgtgcg tgcggcgagg aaggcttccg agcgatcgga gccgcggagt   180
aaacgtcagc gtattccaaa ggctcgccag cctacgggcc ggcattgggg tcaacccggt   240
tacccatggc ccctctacgg caacgagggc tgcggttggg caggatggct cctgtccccc   300
cgcggctctc ggccaagttg gggccccaat gacccacggc gtaggtcacg caatttgggt   360
aaggtcatcg ataccctaac gtgtggcctc gccgacctct ttgggtacat ccctgttgtc   420
ggcggaccgc ttggcggtgt cgcggcagcg ctggcgcatg gcgtcagggc tgttgaagac   480
gggattaatt atgcaacggg gaatttgccc ggttgctcct tttctatctt cctcttagct   540
cttctctcat gcctcactgt acctgcttca gctgtcccct atgctaataa gtctggtatt   600
taccatctta ccaacgactg tcctaatt                                     628

<210> SEQ ID NO 3
<211> LENGTH: 209
<212> TYPE: PRT
<213> ORGANISM: Hepatitis C virus
<220> FEATURE:
<221> NAME/KEY: MISC_FEATURE
<222> LOCATION: (18)..(18)
<223> OTHER INFORMATION: Xaa is any amino acid

<400> SEQUENCE: 3

Met Ser Thr Asn Pro Lys Pro Gln Arg Gln Thr Lys Arg Asn Thr Asn
1               5                   10                  15

Arg Xaa Pro Lys Asp Ile Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Ala Arg Lys Ala Ser Glu Arg Ser Glu Pro Arg Ser Lys Arg Gln Arg
    50                  55                  60

-continued

```
Ile Pro Lys Ala Arg Gln Pro Thr Gly Arg His Trp Gly Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Leu Ala Asp Leu Phe Gly Tyr Ile Pro Val Val Gly Gly Pro Leu
    130                 135                 140

Gly Gly Val Ala Ala Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Pro Tyr Ala Asn Lys Ser Gly Ile Tyr His Leu Thr Asn Asp Cys Pro
        195                 200                 205

Asn

<210> SEQ ID NO 4
<211> LENGTH: 484
<212> TYPE: DNA
<213> ORGANISM: Hepatitis C virus

<400> SEQUENCE: 4
atgagcacga atcctaaacc tcaaagacaa accaaaagaa acaccaaccg tcgccctaag      60
gatattaagt tcccgggcgg cggacagatc gttggtggag tttacttggt accacgcagg    120
ggcccacgat tgggtgtgcg tgcggcgagg aagacttccg agcgatcgga gccgcggagt    180
aaacgtcagc gtattccaaa ggctcgccag cctacgggcc ggcactgggg tcaacccggt    240
tacccatggc ccctctacgg caacgagggc tgcggttggg caggatggct cctgtccccc    300
cgcggctctc ggccaagttg gggccccaat gacccacggc gtaggtcacg caatttgggt    360
aaggtcatcg ataccctaac gtgtggcctc gccgacctct ttgggtacat ccctgtcgtc    420
ggcggaccgc ttggcggtgt cgcggcagcg ctggcgcatg gcgtcagggc tgttgaggac    480
ggga                                                                484

<210> SEQ ID NO 5
<211> LENGTH: 161
<212> TYPE: PRT
<213> ORGANISM: Hepatitis C virus

<400> SEQUENCE: 5

Met Ser Thr Asn Pro Lys Pro Gln Arg Gln Thr Lys Arg Asn Thr Asn
  1               5                  10                  15

Arg Arg Pro Lys Asp Ile Lys Phe Pro Gly Gly Gly Gln Ile Val Gly
                 20                  25                  30

Gly Val Tyr Leu Val Pro Arg Arg Gly Pro Arg Leu Gly Val Arg Ala
             35                  40                  45

Ala Arg Lys Thr Ser Glu Arg Ser Glu Pro Arg Ser Lys Arg Gln Arg
         50                  55                  60

Ile Pro Lys Ala Arg Gln Pro Thr Gly Arg His Trp Gly Gln Pro Gly
 65                  70                  75                  80
```

```
Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Leu Ala Asp Leu Phe Gly Tyr Ile Pro Val Val Gly Gly Pro Leu
    130                 135                 140

Gly Gly Val Ala Ala Ala Leu Ala His Gly Val Arg Ala Val Glu Asp
145                 150                 155                 160

Gly

<210> SEQ ID NO 6
<211> LENGTH: 628
<212> TYPE: DNA
<213> ORGANISM: Hepatitis C virus

<400> SEQUENCE: 6
atgagcacga atcctaaacc tcaaagacaa accaaaagaa acaccaaccg tcgccctaag     60
gatattaagt tcccgggcgg cggacagatc gttggtggag tttacttgtt accacgcagg   120
ggcccacgat tgggtgtgcg tgcggcgagg aagacttccg agcgatcgga gccgcggagt   180
aaacgtcagc gtattccaaa ggctcgccag cctacgggcc ggcactgggg tcaacccggt   240
tacccatggc ccctctacgg caacgagggc tgcggttggg caggatggct cctgtccccc   300
cgcggctctc ggccaagttg gggccccaat gacccacggc gtaggtcacg caatttgggt   360
aaggtcatcg ataccctaac gtgtggcctc gccgacctct ttgggtacat ccctgtcgtc   420
ggcggaccgc ttggcggtgt cgcggcagcg ctggcgcatg gcgtcagggc tgttgaggac   480
gggattaatt atgcaacggg gaatttgccc ggttgctcct tttctatctt cctcttagct   540
cttctctcat gcctcactgt acctgcttca gctgtcccct atgctaataa gtctggtatt   600
taccatctta ccaacgactg tcctaatt                                       628

<210> SEQ ID NO 7
<211> LENGTH: 209
<212> TYPE: PRT
<213> ORGANISM: Hepatitis C virus

<400> SEQUENCE: 7

Met Ser Thr Asn Pro Lys Pro Gln Arg Gln Thr Lys Arg Asn Thr Asn
1               5                   10                  15

Arg Arg Pro Lys Asp Ile Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Ala Arg Lys Thr Ser Glu Arg Ser Glu Pro Arg Ser Lys Arg Gln Arg
    50                  55                  60

Ile Pro Lys Ala Arg Gln Pro Thr Gly Arg His Trp Gly Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125
```

Gly Leu Ala Asp Leu Phe Gly Tyr Ile Pro Val Val Gly Gly Pro Leu
            130                 135                 140

Gly Gly Val Ala Ala Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Pro Tyr Ala Asn Lys Ser Gly Ile Tyr His Leu Thr Asn Asp Cys Pro
        195                 200                 205

Asn

<210> SEQ ID NO 8
<211> LENGTH: 324
<212> TYPE: DNA
<213> ORGANISM: Hepatitis C virus

<400> SEQUENCE: 8
cgttaccgaa agagacattc gtaccgagga gtccatttac caatcatgcc agctcgaccc      60
ggttgcccgg aaagcaatta catcgcttac cgagaggctg tatgtgggag gccctatgtt     120
caactctagg ggcgagccct gcggttaccg caggtgccgc gctagtgggg tcctacccac     180
cagcatgggt aacaccatca catgctacct caaggctaca gccgcatgcc gagcagccgg     240
acccatggac cttgacatgc tcgtgtgtgg ggacgacttg gtggtcatct cggagagcgc     300
gggtacggct gatgatgcag ctgc                                            324

<210> SEQ ID NO 9
<211> LENGTH: 107
<212> TYPE: PRT
<213> ORGANISM: Hepatitis C virus

<400> SEQUENCE: 9

Val Thr Glu Arg Asp Ile Arg Thr Glu Glu Ser Ile Tyr Gln Ser Cys
1               5                   10                  15

Gln Leu Asp Pro Val Ala Arg Lys Ala Ile Thr Ser Leu Thr Glu Arg
            20                  25                  30

Leu Tyr Val Gly Gly Pro Met Phe Asn Ser Arg Gly Glu Pro Cys Gly
        35                  40                  45

Tyr Arg Arg Cys Arg Ala Ser Gly Val Leu Pro Thr Ser Met Gly Asn
50                  55                  60

Thr Ile Thr Cys Tyr Leu Lys Ala Thr Ala Ala Cys Arg Ala Ala Gly
65                  70                  75                  80

Pro Met Asp Leu Asp Met Leu Val Cys Gly Asp Asp Leu Val Val Ser
            85                  90                  95

Arg Arg Ala Arg Val Arg Leu Met Met Gln Leu
            100                 105

<210> SEQ ID NO 10
<211> LENGTH: 1126
<212> TYPE: DNA
<213> ORGANISM: hepatitis C virus

<400> SEQUENCE: 10
gtgcaccatg agcacgaatc ctaaacctca agacaaaacc aaaagaaaca ccaaccgtcg      60
ccctaaggat attaagttcc cgggcggcgg acagatcgtt ggtggagttt acttgttacc     120
acgcaggggc ccacgattgg gtgtgcgtgc ggcgaggaag acttccgagc gatcggagcc     180

-continued

```
gcggagtaaa cgtcagcgta ttccaaaggc tcgccagcct acgggccggc actggggtca      240
acccggttac ccatggcccc tctacggcaa cgagggctgc ggttgggcag gatggctcct      300
gtccccccgc ggctctcggc caagttgggg ccccaatgac ccacggcgta ggtcacgcaa      360
tttgggtaag gtcatcgata ccctaacgtg tggcctcgcc gacctctttg ggtacatccc      420
tgtcgtcggc ggaccgcttg gcggtgtcgc ggcagcgctg gcgcatggcg tcagggctgt      480
tgaggacggg attaattatg caacggggaa tttgcccggt tgctcctttt ctatcttcct      540
cttagctctt ctctcatgcc tcactgtacc tgcttcagct gtcccctatg ctaataagtc      600
tggtatttac catcttacca acgactgtcc taattccagc atcatttatg aagccgagga      660
catcatcatg cacatgcccg ttgtgttcc gtgcgtgttg gttggcaaca tctctcgatg       720
ctgggtccct gcctccccca ccttggccat tcctaacgcg agcgtcccgg tgcggagctt      780
ccgcaagcat gtggatcttc tcgtcggggc tgctgcgctt tgctcggcca tgtacgtggg      840
tgatctttgc ggtggtgtct tcttggtcgg tcaactgatt agttatcggc cgcgacagca      900
cgctactgtg caagattgca actgctccat ctacgcgggc catgttactg gtcatcgtat      960
ggcgtgggac atgatgatga attggtcgcc gactgtaacg taccttgtgt ccagcattct     1020
caggataccc cagatcttaa ttgacatctt tgttggtggc cactggggag tcataggagc     1080
tgtcttgttt tactccatgc aggccaactg ggccaaggtg atctgt                    1126
```

<210> SEQ ID NO 11
<211> LENGTH: 373
<212> TYPE: PRT
<213> ORGANISM: hepatitis C virus

<400> SEQUENCE: 11

```
Met Ser Thr Asn Pro Lys Pro Gln Arg Gln Thr Lys Arg Asn Thr Asn
1               5                   10                  15

Arg Arg Pro Lys Asp Ile Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Ala Arg Lys Thr Ser Glu Arg Ser Glu Pro Arg Ser Lys Arg Gln Arg
        50                  55                  60

Ile Pro Lys Ala Arg Gln Pro Thr Gly Arg His Trp Gly Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
            115                 120                 125

Gly Leu Ala Asp Leu Phe Gly Tyr Ile Pro Val Val Gly Gly Pro Leu
        130                 135                 140

Gly Gly Val Ala Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
                180                 185                 190

Pro Tyr Ala Asn Lys Ser Gly Ile Tyr His Leu Thr Asn Asp Cys Pro
            195                 200                 205
```

```
Asn Ser Ser Ile Ile Tyr Glu Ala Glu Asp Ile Met His Met Pro
    210                 215                 220

Gly Cys Val Pro Cys Val Leu Val Gly Asn Ile Ser Arg Cys Trp Val
225                 230                 235                 240

Pro Ala Ser Pro Thr Leu Ala Ile Pro Asn Ala Ser Val Pro Val Arg
                245                 250                 255

Ser Phe Arg Lys His Val Asp Leu Leu Val Gly Ala Ala Ala Leu Cys
            260                 265                 270

Ser Ala Met Tyr Val Gly Asp Leu Cys Gly Val Phe Leu Val Gly
        275                 280                 285

Gln Leu Ile Ser Tyr Arg Pro Arg Gln His Ala Thr Val Gln Asp Cys
    290                 295                 300

Asn Cys Ser Ile Tyr Ala Gly His Val Thr Gly His Arg Met Ala Trp
305                 310                 315                 320

Asp Met Met Met Asn Trp Ser Pro Thr Val Thr Tyr Leu Val Ser Ser
                325                 330                 335

Ile Leu Arg Ile Pro Gln Ile Leu Ile Asp Ile Phe Val Gly Gly His
            340                 345                 350

Trp Gly Val Ile Gly Ala Val Leu Phe Tyr Ser Met Gln Ala Asn Trp
        355                 360                 365

Ala Lys Val Ile Cys
    370

<210> SEQ ID NO 12
<211> LENGTH: 1126
<212> TYPE: DNA
<213> ORGANISM: hepatitis C virus

<400> SEQUENCE: 12
gtgcaccatg agcacgaatc ctaaacctca agacaaaacc aaaagaaaca ccaaccgtcg     60
ccctaaggat attaagttcc cgggcggcgg acagatcgtt ggtggagttt acttggtacc    120
acgcaggggc ccacgattgg gtgtgcgtgc ggcgaggaag acttccgagc gatcggagcc    180
gcggagtaaa cgtcagcgta ttccaaaggc tcgccagcct acgggccggc actggggtca    240
acccggttac ccatggcccc tctacggcaa cgagggctgc ggttgggcag atggctcct    300 gtcccccgc ggctctcggc caagttgggg ccccaatgac ccacgcgta ggtcacgcaa    360 tttgggtaag gtcatcgata ccctaacgtg tggcctcgcc gacctctttg ggtacatccc    420
tgtcgtcggc ggaccgcttg gcggtgtcgc ggcagcgctg gcgcatggcg tcagggctgt    480
tgaggacggg attaattatg caacggggaa tttgcccggt tgctcctttt ctatcttcct    540
cttagctctt ctctcatgcc tcactgtacc tgcttcagct gtcccctatg ctaataagtc    600
tggtatttac catcttacca acgactgccc taattccagc atcatttatg aagccgagga    660
catcatcatg cacatgcccg gttgtgttcc gtgcgtgttg gttggcaaca tctctcgatg    720
ctgggtccct gcctccccca ccttggccat tcctaacgcg agcgtcccgg tgcggagctt    780
ccgcaagcat gtggatcttc tcgtcggggc tgctgcgctt gctcggcca tgtacgtggg    840 tgatctttgc ggtggcgtct tcttggtcgg tcaactgatt agttatcggc cgcgacagca    900
cgctactgtg caagattgca actgctccat ctacgcgggc catgttactg gtcatcgtat    960
ggcgtgggac atgatgatga attggtcgcc gactgtaacg taccttgtgt ccagcattct   1020
caggataccc cagatcttaa ttgacatctt tgttggtggc cactggggag tcataggagc   1080
tgtcttgttt tactccatgc aggccaactg ggccaaggtg atctgt                  1126
```

<210> SEQ ID NO 13
<211> LENGTH: 373
<212> TYPE: PRT
<213> ORGANISM: hepatitis C virus

<400> SEQUENCE: 13

```
Met Ser Thr Asn Pro Lys Pro Gln Arg Gln Thr Lys Arg Asn Thr Asn
1               5                   10                  15

Arg Arg Pro Lys Asp Ile Lys Phe Pro Gly Gly Gln Ile Val Gly
            20                  25                  30

Gly Val Tyr Leu Val Pro Arg Arg Gly Pro Arg Leu Gly Val Arg Ala
        35                  40                  45

Ala Arg Lys Thr Ser Glu Arg Ser Glu Pro Arg Ser Lys Arg Gln Arg
        50                  55                  60

Ile Pro Lys Ala Arg Gln Pro Thr Gly Arg His Trp Gly Gln Pro Gly
65              70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Leu Ala Asp Leu Phe Gly Tyr Ile Pro Val Val Gly Gly Pro Leu
130                 135                 140

Gly Gly Val Ala Ala Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Pro Tyr Ala Asn Lys Ser Gly Ile Tyr His Leu Thr Asn Asp Cys Pro
        195                 200                 205

Asn Ser Ser Ile Ile Tyr Glu Ala Glu Asp Ile Ile Met His Met Pro
    210                 215                 220

Gly Cys Val Pro Cys Val Leu Val Gly Asn Ile Ser Arg Cys Trp Val
225                 230                 235                 240

Pro Ala Ser Pro Thr Leu Ala Ile Pro Asn Ala Ser Val Pro Val Arg
                245                 250                 255

Ser Phe Arg Lys His Val Asp Leu Leu Val Gly Ala Ala Leu Cys
            260                 265                 270

Ser Ala Met Tyr Val Gly Asp Leu Cys Gly Gly Val Phe Leu Val Gly
        275                 280                 285

Gln Leu Ile Ser Tyr Arg Pro Arg Gln His Ala Thr Val Gln Asp Cys
    290                 295                 300

Asn Cys Ser Ile Tyr Ala Gly His Val Thr Gly His Arg Met Ala Trp
305                 310                 315                 320

Asp Met Met Met Asn Trp Ser Pro Thr Val Thr Tyr Leu Val Ser Ser
                325                 330                 335

Ile Leu Arg Ile Pro Gln Ile Leu Ile Asp Ile Phe Val Gly Gly His
            340                 345                 350

Trp Gly Val Ile Gly Ala Val Leu Phe Tyr Ser Met Gln Ala Asn Trp
        355                 360                 365

Ala Lys Val Ile Cys
```

<210> SEQ ID NO 14
<211> LENGTH: 1126
<212> TYPE: DNA
<213> ORGANISM: hepatitis C virus

<400> SEQUENCE: 14

```
gtgcaccatg agcacgaatc ctaaacctca agacaaacc aaaagaaaca ccaaccgtcg    60
ccctaaggat attaagttcc cgggcggcgg acagatcgtt ggtggagttt acttgttacc   120
acgcaggggc ccacgattgg gtgtgcgtgc ggcgaggaag gcttccgagc gatcggagcc   180
gcggagtaaa cgtcagcgta ttccaaaggc tcgccagcct acgggccggc attggggtca   240
acccggttac ccatggcccc tctacggcaa cgagggctgc ggttgggcag gatggctcct   300
gtccccccgc ggctctcggc caagttgggg ccccaatgac ccacggcgta ggtcacgcaa   360
tttgggtaag gtcatcgata ccctaacgtg tggcctcgcc gacctctttg gtacatccc    420
tgttgtcggc ggaccgcttg gcggtgtcgc ggcagcgctg gcgcatggcg tcagggctgt   480
tgaagacggg attaattatg caacggggaa tttgcccggt tgctcctttt ctatcttcct   540
cttagctctt ctctcatgcc tcactgtacc tgcttcagct gtccctatg ctaataagtc    600
tggtatttac catcttacca acgactgtcc taattccagc atcatttatg aagccgagga   660
catcatcatg cacatgcccg ttgtgttcc gtgcgtgttg gttggcaaca tctctcgatg    720
ctgggtccct gcctccccca ccttggccat tcctaacgcg agcgtcccgg tgcggagctt   780
ccgcaagcat gtggatcttc tcgtcgggc tgctgcgctt tgctcggcca gtacgtggg    840
tgatctttgc ggtggtgtct tcttggtcgg tcaactgatt agttatcggc cgcgacagca   900
cgctactgtg caagattgca actgctccat ctacgcgggc catgttactg gtcatcgtat   960
ggcgtgggac atgatgatga attggtcgcc gactgtaacg taccttgtgt ccagcattct  1020
caggataccc cagatcttaa ttgacatctt tgttggtggc cactggggag tcataggagc  1080
tgtcttgttt tactccatgc aggccaactg ggccaaggtg atctgt                 1126
```

<210> SEQ ID NO 15
<211> LENGTH: 373
<212> TYPE: PRT
<213> ORGANISM: hepatitis C virus

<400> SEQUENCE: 15

```
Met Ser Thr Asn Pro Lys Pro Gln Arg Gln Thr Lys Arg Asn Thr Asn
1               5                   10                  15

Arg Arg Pro Lys Asp Ile Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Ala Arg Lys Ala Ser Glu Arg Ser Glu Pro Arg Ser Lys Arg Gln Arg
        50                  55                  60

Ile Pro Lys Ala Arg Gln Pro Thr Gly Arg His Trp Gly Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125
```

Gly Leu Ala Asp Leu Phe Gly Tyr Ile Pro Val Val Gly Gly Pro Leu
    130                 135                 140

Gly Gly Val Ala Ala Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Pro Tyr Ala Asn Lys Ser Gly Ile Tyr His Leu Thr Asn Asp Cys Pro
        195                 200                 205

Asn Ser Ser Ile Ile Tyr Glu Ala Glu Asp Ile Ile Met His Met Pro
210                 215                 220

Gly Cys Val Pro Cys Val Leu Val Gly Asn Ile Ser Arg Cys Trp Val
225                 230                 235                 240

Pro Ala Ser Pro Thr Leu Ala Ile Pro Asn Ala Ser Val Pro Val Arg
                245                 250                 255

Ser Phe Arg Lys His Val Asp Leu Leu Val Gly Ala Ala Ala Leu Cys
            260                 265                 270

Ser Ala Met Tyr Val Gly Asp Leu Cys Gly Gly Val Phe Leu Val Gly
        275                 280                 285

Gln Leu Ile Ser Tyr Arg Pro Arg Gln His Ala Thr Val Gln Asp Cys
    290                 295                 300

Asn Cys Ser Ile Tyr Ala Gly His Val Thr Gly His Arg Met Ala Trp
305                 310                 315                 320

Asp Met Met Met Asn Trp Ser Pro Thr Val Thr Tyr Leu Val Ser Ser
                325                 330                 335

Ile Leu Arg Ile Pro Gln Ile Leu Ile Asp Ile Phe Val Gly Gly His
            340                 345                 350

Trp Gly Val Ile Gly Ala Val Leu Phe Tyr Ser Met Gln Ala Asn Trp
        355                 360                 365

Ala Lys Val Ile Cys
    370

<210> SEQ ID NO 16
<211> LENGTH: 27
<212> TYPE: DNA
<213> ORGANISM: Artificial Sequence
<220> FEATURE:
<221> NAME/KEY: misc_feature
<223> OTHER INFORMATION: HCPr 29

<400> SEQUENCE: 16
gctcatgytg cacggtctac gagacct                                27

<210> SEQ ID NO 17
<211> LENGTH: 26
<212> TYPE: DNA
<213> ORGANISM: Artificial Sequence
<220> FEATURE:
<221> NAME/KEY: misc_feature
<223> OTHER INFORMATION: HCPr 52

<400> SEQUENCE: 17
atgttgggta aggtcatcga taccct                                 26

<210> SEQ ID NO 18
<211> LENGTH: 27
<212> TYPE: DNA

```
<213> ORGANISM: Artificial Sequence
<220> FEATURE:
<221> NAME/KEY: misc_feature
<223> OTHER INFORMATION: HCPr 54

<400> SEQUENCE: 18
ctattaccag ttcatcatca tatccca                                              27

<210> SEQ ID NO 19
<211> LENGTH: 26
<212> TYPE: DNA
<213> ORGANISM: Artificial Sequence
<220> FEATURE:
<221> NAME/KEY: misc_feature
<223> OTHER INFORMATION: HCPr 95

<400> SEQUENCE: 19
tctagccatg gcgttagtwk gagtgt                                               26

<210> SEQ ID NO 20
<211> LENGTH: 26
<212> TYPE: DNA
<213> ORGANISM: Artificial Sequence
<220> FEATURE:
<221> NAME/KEY: misc_feature
<223> OTHER INFORMATION: HCPr 96

<400> SEQUENCE: 20
cactcgcaag caccctatca ggcagt                                               26

<210> SEQ ID NO 21
<211> LENGTH: 27
<212> TYPE: DNA
<213> ORGANISM: Artificial Sequence
<220> FEATURE:
<221> NAME/KEY: misc_feature
<223> OTHER INFORMATION: HCPr 98

<400> SEQUENCE: 21
ccctgtgagg aactsctgtc ttcacgc                                              27

<210> SEQ ID NO 22
<211> LENGTH: 21
<212> TYPE: DNA
<213> ORGANISM: Artificial Sequence
<220> FEATURE:
<221> NAME/KEY: misc_feature
<223> OTHER INFORMATION: HCPr 292

<400> SEQUENCE: 22
ccctatgggc ttctcgtatg a                                                    21

<210> SEQ ID NO 23
<211> LENGTH: 23
<212> TYPE: DNA
<213> ORGANISM: Artificial Sequence
<220> FEATURE:
<221> NAME/KEY: misc_feature
<223> OTHER INFORMATION: HCPr 293

<400> SEQUENCE: 23
tatgacaccc gctgctttga ctc                                                  23

<210> SEQ ID NO 24
<211> LENGTH: 21
<212> TYPE: DNA
<213> ORGANISM: Artificial Sequence
```

```
<220> FEATURE:
<221> NAME/KEY: misc_feature
<223> OTHER INFORMATION: HCPr 294

<400> SEQUENCE: 24
cctggtcata gcctccgtga a                                              21

<210> SEQ ID NO 25
<211> LENGTH: 20
<212> TYPE: DNA
<213> ORGANISM: Artificial Sequence
<220> FEATURE:
<221> NAME/KEY: misc_feature
<223> OTHER INFORMATION: HCPr 295

<400> SEQUENCE: 25
ggggccgagt acctggtcat                                                20

<210> SEQ ID NO 26
<211> LENGTH: 23
<212> TYPE: DNA
<213> ORGANISM: Artificial Sequence
<220> FEATURE:
<221> NAME/KEY: misc_feature
<223> OTHER INFORMATION: HCPr 634

<400> SEQUENCE: 26
ctctcttgck tgactgtgcc cgc                                            23

<210> SEQ ID NO 27
<211> LENGTH: 25
<212> TYPE: DNA
<213> ORGANISM: Artificial Sequence
<220> FEATURE:
<221> NAME/KEY: misc_feature
<223> OTHER INFORMATION: HCPr 635

<400> SEQUENCE: 27
cgcgtcgacg ccggcaaata gcagc                                          25

<210> SEQ ID NO 28
<211> LENGTH: 23
<212> TYPE: DNA
<213> ORGANISM: Artificial Sequence
<220> FEATURE:
<221> NAME/KEY: misc_feature
<223> OTHER INFORMATION: HCPr 636

<400> SEQUENCE: 28
gcktgactgt gcccgcttcw gcc                                            23

<210> SEQ ID NO 29
<211> LENGTH: 26
<212> TYPE: DNA
<213> ORGANISM: Artificial Sequence
<220> FEATURE:
<221> NAME/KEY: misc_feature
<223> OTHER INFORMATION: HCPr 637

<400> SEQUENCE: 29
tcgacgccgg caaakagcaw cagcac                                         26

<210> SEQ ID NO 30
<211> LENGTH: 23
<212> TYPE: DNA
<213> ORGANISM: Artificial Sequence
<220> FEATURE:
```

```
<221> NAME/KEY: misc_feature
<223> OTHER INFORMATION: HCPr 638

<400> SEQUENCE: 30
ctgtcktgkt tgaccwtccc agc                                        23

<210> SEQ ID NO 31
<211> LENGTH: 25
<212> TYPE: DNA
<213> ORGANISM: Artificial Sequence
<220> FEATURE:
<221> NAME/KEY: misc_feature
<223> OTHER INFORMATION: HCPr 639

<400> SEQUENCE: 31
cccgtcaacg ccggcwaaga gtawc                                      25

<210> SEQ ID NO 32
<211> LENGTH: 23
<212> TYPE: DNA
<213> ORGANISM: Artificial Sequence
<220> FEATURE:
<221> NAME/KEY: misc_feature
<223> OTHER INFORMATION: HCPr 640

<400> SEQUENCE: 32
gtktgaccak cccagcttcc gct                                        23

<210> SEQ ID NO 33
<211> LENGTH: 26
<212> TYPE: DNA
<213> ORGANISM: Artificial Sequence
<220> FEATURE:
<221> NAME/KEY: misc_feature
<223> OTHER INFORMATION: HCPr 641

<400> SEQUENCE: 33
tcaacgccgg cwaawagtaw cwkcac                                     26

<210> SEQ ID NO 34
<211> LENGTH: 24
<212> TYPE: DNA
<213> ORGANISM: Artificial Sequence
<220> FEATURE:
<221> NAME/KEY: misc_feature
<223> OTHER INFORMATION: HCPr 666

<400> SEQUENCE: 34
actgcctgat agggtgcttg cgag                                       24

<210> SEQ ID NO 35
<211> LENGTH: 20
<212> TYPE: DNA
<213> ORGANISM: Artificial Sequence
<220> FEATURE:
<221> NAME/KEY: misc_feature
<223> OTHER INFORMATION: HCPr 667

<400> SEQUENCE: 35
cccgggaggt ctcgtagacc                                            20

<210> SEQ ID NO 36
<211> LENGTH: 580
<212> TYPE: DNA
<213> ORGANISM: hepatitis C virus

<400> SEQUENCE: 36
```

```
cgtcgccta aggatattaa gttcccgggc ggcggacaga tcgttggtgg agtttacttg    60
ttaccacgca ggggcccacg attgggtgtg cgtgcggcga ggaagacttc cgagcgatcg   120
gagccgcgga gtaaacgtca gcgtattcca aaggctcgcc agcctacggg ccggcactgg   180
ggtcaacccg gttacccatg gccctctac ggcaacgagg gctgcggttg ggcaggatgg    240
ctcctgtccc cccgcggctc tcggccaagt tggggcccca atgacccacg gcgtaggtca   300
cgcaatttgg gtaaggtcat cgataccta acgtgtggcc tcgccgacct ctttgggtac    360
atccctgtcg tcggcggacc gcttggcggt gtcgcggcag cgctggcgca tggcgtcagg   420
gctgttgagg acgggattaa ttatgcaacg gggaatttgc ccggttgctc cttttctatc   480
ttcctcttag ctcttctctc atgcctcact gtacctgctt cagctgtccc ctatgctaat   540
aagtctggta tttaccatct taccaacgac tgtcctaatt                         580
```

<210> SEQ ID NO 37
<211> LENGTH: 580
<212> TYPE: DNA
<213> ORGANISM: hepatitis C virus

<400> SEQUENCE: 37

```
cgtcgccta aggatattaa gttcccgggc ggcggacaga tcgttggtgg agtttacttg    60
gtaccacgca ggggcccacg attgggtgtg cgtgcggcga ggaagacttc cgagcgatcg   120
gagccgcgga gtaaacgtca gcgtattcca aaggctcgcc agcctacggg ccggcactgg   180
ggtcaacccg gttacccatg gccctctac ggcaacgagg gctgcggttg ggcaggatgg    240
ctcctgtccc cccgcggctc tcggccaagt tggggcccca atgacccacg gcgtaggtca   300
cgcaatttgg gtaaggtcat cgataccta acgtgtggcc tcgccgacct ctttgggtac    360
atccctgtcg tcggcggacc gcttggcggt gtcgcggcag cgctggcgca tggcgtcagg   420
gctgttgagg acgggattaa ttatgcaacg gggaatttgc ccggttgctc cttttctatc   480
ttcctcttag ctcttctctc atgcctcact gtacctgctt cagctgtccc ctatgctaat   540
aagtctggta tttaccatct taccaacgac tgccctaatt                         580
```

<210> SEQ ID NO 38
<211> LENGTH: 580
<212> TYPE: DNA
<213> ORGANISM: hepatitis C virus

<400> SEQUENCE: 38

```
cgtcgccta aggatattaa gttcccgggc ggcggacaga tcgttggtgg agtttacttg    60
ttaccacgca ggggcccacg attgggtgtg cgtgcggcga ggaaggcttc cgagcgatcg   120
gagccgcgga gtaaacgtca gcgtattcca aaggctcgcc agcctacggg ccggcattgg   180
ggtcaacccg gttacccatg gccctctac ggcaacgagg gctgcggttg ggcaggatgg    240
ctcctgtccc cccgcggctc tcggccaagt tggggcccca atgacccacg gcgtaggtca   300
cgcaatttgg gtaaggtcat cgataccta acgtgtggcc tcgccgacct ctttgggtac    360
atccctgttg tcggcggacc gcttggcggt gtcgcggcag cgctggcgca tggcgtcagg   420
gctgttgaag acgggattaa ttatgcaacg gggaatttgc ccggttgctc cttttctatc   480
ttcctcttag ctcttctctc atgcctcact gtacctgctt cagctgtccc ctatgctaat   540
aagtctggta tttaccatct taccaacgac tgtcctaatt                         580
```

<210> SEQ ID NO 39

```
<211> LENGTH: 573
<212> TYPE: DNA
<213> ORGANISM: hepatitis C virus

<400> SEQUENCE: 39
atgagcacga atcctaaacc tcaaagacaa accaaaagaa acaccaaccg tcgccctaag      60
gatattaagt tcccgggcgg cggacagatc gttggtggag tttacttgtt accacgcagg    120
ggcccacgat tgggtgtgcg tgcggcgagg aagacttccg agcgatcgga gccgcggagt    180
aaacgtcagc gtattccaaa ggctcgccag cctacgggcc ggcactgggg tcaacccggt    240
tacccatggc ccctctacgg caacgagggc tgcggttggg caggatggct cctgtccccc    300
cgcggctctc ggccaagttg gggccccaat gacccacggc gtaggtcacg caatttgggt    360
aaggtcatcg atacccctaac gtgtggcctc gccgacctct tgggtacat ccctgtcgtc    420
ggcggaccgc ttggcggtgt cgcggcagcg ctggcgcatg gcgtcagggc tgttgaggac    480
gggattaatt atgcaacggg gaatttgccc ggttgctcct tttctatctt cctcttagct    540
cttctctcat gcctcactgt acctgcttca gct                                  573

<210> SEQ ID NO 40
<211> LENGTH: 573
<212> TYPE: DNA
<213> ORGANISM: hepatitis C virus

<400> SEQUENCE: 40
atgagcacga atcctaaacc tcaaagacaa accaaaagaa acaccaaccg tcgccctaag      60
gatattaagt tcccgggcgg cggacagatc gttggtggag tttacttggt accacgcagg    120
ggcccacgat tgggtgtgcg tgcggcgagg aagacttccg agcgatcgga gccgcggagt    180
aaacgtcagc gtattccaaa ggctcgccag cctacgggcc ggcactgggg tcaacccggt    240
tacccatggc ccctctacgg caacgagggc tgcggttggg caggatggct cctgtccccc    300
cgcggctctc ggccaagttg gggccccaat gacccacggc gtaggtcacg caatttgggt    360
aaggtcatcg atacccctaac gtgtggcctc gccgacctct tgggtacat ccctgtcgtc    420
ggcggaccgc ttggcggtgt cgcggcagcg ctggcgcatg gcgtcagggc tgttgaggac    480
gggattaatt atgcaacggg gaatttgccc ggttgctcct tttctatctt cctcttagct    540
cttctctcat gcctcactgt acctgcttca gct                                  573

<210> SEQ ID NO 41
<211> LENGTH: 573
<212> TYPE: DNA
<213> ORGANISM: hepatitis C virus

<400> SEQUENCE: 41
atgagcacga atcctaaacc tcaaagacaa accaaaagaa acaccaaccg tcgccctaag      60
gatattaagt tcccgggcgg cggacagatc gttggtggag tttacttgtt accacgcagg    120
ggcccacgat tgggtgtgcg tgcggcgagg aaggcttccg agcgatcgga gccgcggagt    180
aaacgtcagc gtattccaaa ggctcgccag cctacgggcc ggcattgggg tcaacccggt    240
tacccatggc ccctctacgg caacgagggc tgcggttggg caggatggct cctgtccccc    300
cgcggctctc ggccaagttg gggccccaat gacccacggc gtaggtcacg caatttgggt    360
aaggtcatcg atacccctaac gtgtggcctc gccgacctct tgggtacat ccctgttgtc    420
ggcggaccgc ttggcggtgt cgcggcagcg ctggcgcatg gcgtcagggc tgttgaagac    480
gggattaatt atgcaacggg gaatttgccc ggttgctcct tttctatctt cctcttagct    540
```

```
cttctctcat gcctcactgt acctgcttca gct                              573
```

```
<210> SEQ ID NO 42
<211> LENGTH: 546
<212> TYPE: DNA
<213> ORGANISM: hepatitis C virus

<400> SEQUENCE: 42
gtcccctatg ctaataagtc tggtatttac catcttacca acgactgtcc taattccagc    60
atcatttatg aagccgagga catcatcatg cacatgcccg ttgtgttcc gtgcgtgttg    120
gttggcaaca tctctcgatg ctgggtccct gcctccccca ccttggccat tcctaacgcg   180
agcgtcccgg tgcggagctt ccgcaagcat gtggatcttc tcgtcgggc tgctgcgctt    240
tgctcggcca tgtacgtggg tgatctttgc ggtggtgtct tcttggtcgg tcaactgatt    300
agttatcggc cgcgacagca cgctactgtg caagattgca actgctccat ctacgcgggc   360
catgttactg gtcatcgtat ggcgtgggac atgatgatga attggtcgcc gactgtaacg   420
taccttgtgt ccagcattct caggataccc cagatcttaa ttgacatctt tgttggtggc   480
cactggggag tcataggagc tgtcttgttt tactccatgc aggccaactg ggccaaggtg   540
atctgt                                                              546
```

```
<210> SEQ ID NO 43
<211> LENGTH: 33
<212> TYPE: DNA
<213> ORGANISM: hepatitis C virus

<400> SEQUENCE: 43
gctcgccagc ctacgggccg gcactggggt caa                                33
```

```
<210> SEQ ID NO 44
<211> LENGTH: 36
<212> TYPE: DNA
<213> ORGANISM: hepatitis C virus

<400> SEQUENCE: 44 gtccctatg ctaataagtc tggtatttac catctt                              36
```

```
<210> SEQ ID NO 45
<211> LENGTH: 33
<212> TYPE: DNA
<213> ORGANISM: hepatitis C virus

<400> SEQUENCE: 45
atttatgaag ccgaggacat catcatgcac atg                                33
```

```
<210> SEQ ID NO 46
<211> LENGTH: 39
<212> TYPE: DNA
<213> ORGANISM: hepatitis C virus

<400> SEQUENCE: 46
gtgttggttg gcaacatctc tcgatgctgg gtccctgcc                          39
```

```
<210> SEQ ID NO 47
<211> LENGTH: 30
<212> TYPE: DNA
<213> ORGANISM: hepatitis C virus

<400> SEQUENCE: 47
```

```
attcctaacg cgagcgtccc ggtgcggagc                                         30
```

<210> SEQ ID NO 48
<211> LENGTH: 30
<212> TYPE: DNA
<213> ORGANISM: hepatitis C virus

<400> SEQUENCE: 48

```
cggccgcgac agcacgctac tgtgcaagat                                         30
```

<210> SEQ ID NO 49
<211> LENGTH: 39
<212> TYPE: DNA
<213> ORGANISM: hepatitis C virus

<400> SEQUENCE: 49

```
gtaacgtacc ttgtgtccag cattctcagg ataccccag                               39
```

<210> SEQ ID NO 50
<211> LENGTH: 193
<212> TYPE: PRT
<213> ORGANISM: hepatitis C virus

<400> SEQUENCE: 50

Arg Arg Pro Lys Asp Ile Lys Phe Pro Gly Gly Gln Ile Val Gly
1               5                   10                  15

Gly Val Tyr Leu Leu Pro Arg Arg Gly Pro Arg Leu Gly Val Arg Ala
            20                  25                  30

Ala Arg Lys Thr Ser Glu Arg Ser Glu Pro Arg Ser Lys Arg Gln Arg
        35                  40                  45

Ile Pro Lys Ala Arg Gln Pro Thr Gly Arg His Trp Gly Gln Pro Gly
    50                  55                  60

Tyr Pro Trp Pro Leu Tyr Gly Asn Glu Gly Cys Gly Trp Ala Gly Trp
65                  70                  75                  80

Leu Leu Ser Pro Arg Gly Ser Arg Pro Ser Trp Gly Pro Asn Asp Pro
                85                  90                  95

Arg Arg Arg Ser Arg Asn Leu Gly Lys Val Ile Asp Thr Leu Thr Cys
            100                 105                 110

Gly Leu Ala Asp Leu Phe Gly Tyr Ile Pro Val Val Gly Gly Pro Leu
        115                 120                 125

Gly Gly Val Ala Ala Ala Leu Ala His Gly Val Arg Ala Val Glu Asp
    130                 135                 140

Gly Ile Asn Tyr Ala Thr Gly Asn Leu Pro Gly Cys Ser Phe Ser Ile
145                 150                 155                 160

Phe Leu Leu Ala Leu Leu Ser Cys Leu Thr Val Pro Ala Ser Ala Val
                165                 170                 175

Pro Tyr Ala Asn Lys Ser Gly Ile Tyr His Leu Thr Asn Asp Cys Pro
            180                 185                 190

Asn

<210> SEQ ID NO 51
<211> LENGTH: 193
<212> TYPE: PRT
<213> ORGANISM: hepatitis C virus

<400> SEQUENCE: 51

Arg Arg Pro Lys Asp Ile Lys Phe Pro Gly Gly Gln Ile Val Gly
1               5                   10                  15

-continued

```
Gly Val Tyr Leu Val Pro Arg Arg Gly Pro Arg Leu Gly Val Arg Ala
             20                  25                  30

Ala Arg Lys Thr Ser Glu Arg Ser Glu Pro Arg Ser Lys Arg Gln Arg
         35                  40                  45

Ile Pro Lys Ala Arg Gln Pro Thr Gly Arg His Trp Gly Gln Pro Gly
 50                  55                  60

Tyr Pro Trp Pro Leu Tyr Gly Asn Glu Gly Cys Gly Trp Ala Gly Trp
 65                  70                  75                  80

Leu Leu Ser Pro Arg Gly Ser Arg Pro Ser Trp Gly Pro Asn Asp Pro
             85                  90                  95

Arg Arg Arg Ser Arg Asn Leu Gly Lys Val Ile Asp Thr Leu Thr Cys
        100                 105                 110

Gly Leu Ala Asp Leu Phe Gly Tyr Ile Pro Val Val Gly Gly Pro Leu
        115                 120                 125

Gly Gly Val Ala Ala Ala Leu Ala His Gly Val Arg Ala Val Glu Asp
130                 135                 140

Gly Ile Asn Tyr Ala Thr Gly Asn Leu Pro Gly Cys Ser Phe Ser Ile
145                 150                 155                 160

Phe Leu Leu Ala Leu Leu Ser Cys Leu Thr Val Pro Ala Ser Ala Val
                165                 170                 175

Pro Tyr Ala Asn Lys Ser Gly Ile Tyr His Leu Thr Asn Asp Cys Pro
            180                 185                 190

Asn

<210> SEQ ID NO 52
<211> LENGTH: 193
<212> TYPE: PRT
<213> ORGANISM: hepatitis C virus

<400> SEQUENCE: 52

Arg Arg Pro Lys Asp Ile Lys Phe Pro Gly Gly Gly Gln Ile Val Gly
 1               5                  10                  15

Gly Val Tyr Leu Leu Pro Arg Arg Gly Pro Arg Leu Gly Val Arg Ala
             20                  25                  30

Ala Arg Lys Ala Ser Glu Arg Ser Glu Pro Arg Ser Lys Arg Gln Arg
         35                  40                  45

Ile Pro Lys Ala Arg Gln Pro Thr Gly Arg His Trp Gly Gln Pro Gly
 50                  55                  60

Tyr Pro Trp Pro Leu Tyr Gly Asn Glu Gly Cys Gly Trp Ala Gly Trp
 65                  70                  75                  80

Leu Leu Ser Pro Arg Gly Ser Arg Pro Ser Trp Gly Pro Asn Asp Pro
             85                  90                  95

Arg Arg Arg Ser Arg Asn Leu Gly Lys Val Ile Asp Thr Leu Thr Cys
        100                 105                 110

Gly Leu Ala Asp Leu Phe Gly Tyr Ile Pro Val Val Gly Gly Pro Leu
        115                 120                 125

Gly Gly Val Ala Ala Ala Leu Ala His Gly Val Arg Ala Val Glu Asp
130                 135                 140

Gly Ile Asn Tyr Ala Thr Gly Asn Leu Pro Gly Cys Ser Phe Ser Ile
145                 150                 155                 160

Phe Leu Leu Ala Leu Leu Ser Cys Leu Thr Val Pro Ala Ser Ala Val
                165                 170                 175

Pro Tyr Ala Asn Lys Ser Gly Ile Tyr His Leu Thr Asn Asp Cys Pro
            180                 185                 190
```

Asn

<210> SEQ ID NO 53
<211> LENGTH: 191
<212> TYPE: PRT
<213> ORGANISM: hepatitis C virus

<400> SEQUENCE: 53

```
Met Ser Thr Asn Pro Lys Pro Gln Arg Gln Thr Lys Arg Asn Thr Asn
1               5                   10                  15

Arg Arg Pro Lys Asp Ile Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Ala Arg Lys Thr Ser Glu Arg Ser Glu Pro Arg Ser Lys Arg Gln Arg
    50                  55                  60

Ile Pro Lys Ala Arg Gln Pro Thr Gly Arg His Trp Gly Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Leu Ala Asp Leu Phe Gly Tyr Ile Pro Val Val Gly Gly Pro Leu
    130                 135                 140

Gly Gly Val Ala Ala Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190
```

<210> SEQ ID NO 54
<211> LENGTH: 191
<212> TYPE: PRT
<213> ORGANISM: hepatitis C virus

<400> SEQUENCE: 54

```
Met Ser Thr Asn Pro Lys Pro Gln Arg Gln Thr Lys Arg Asn Thr Asn
1               5                   10                  15

Arg Arg Pro Lys Asp Ile Lys Phe Pro Gly Gly Gly Gln Ile Val Gly
            20                  25                  30

Gly Val Tyr Leu Val Pro Arg Arg Gly Pro Arg Leu Gly Val Arg Ala
        35                  40                  45

Ala Arg Lys Thr Ser Glu Arg Ser Glu Pro Arg Ser Lys Arg Gln Arg
    50                  55                  60

Ile Pro Lys Ala Arg Gln Pro Thr Gly Arg His Trp Gly Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Leu Ala Asp Leu Phe Gly Tyr Ile Pro Val Val Gly Gly Pro Leu
```

```
            130                 135                 140
Gly Gly Val Ala Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

<210> SEQ ID NO 55
<211> LENGTH: 191
<212> TYPE: PRT
<213> ORGANISM: hepatitis C virus

<400> SEQUENCE: 55

Met Ser Thr Asn Pro Lys Pro Gln Arg Gln Thr Lys Arg Asn Thr Asn
1               5                   10                  15

Arg Arg Pro Lys Asp Ile Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Ala Arg Lys Ala Ser Glu Arg Ser Glu Pro Arg Ser Lys Arg Gln Arg
    50                  55                  60

Ile Pro Lys Ala Arg Gln Pro Thr Gly Arg His Trp Gly Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Leu Ala Asp Leu Phe Gly Tyr Ile Pro Val Val Gly Gly Pro Leu
    130                 135                 140

Gly Gly Val Ala Ala Leu Ala His Gly Val Arg Ala Val Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

<210> SEQ ID NO 56
<211> LENGTH: 182
<212> TYPE: PRT
<213> ORGANISM: hepatitis C virus

<400> SEQUENCE: 56

Val Pro Tyr Ala Asn Lys Ser Gly Ile Tyr His Leu Thr Asn Asp Cys
1               5                   10                  15

Pro Asn Ser Ser Ile Ile Tyr Glu Ala Glu Asp Ile Ile Met His Met
            20                  25                  30

Pro Gly Cys Val Pro Cys Val Leu Val Gly Asn Ile Ser Arg Cys Trp
        35                  40                  45

Val Pro Ala Ser Pro Thr Leu Ala Ile Pro Asn Ala Ser Val Pro Val
    50                  55                  60

Arg Ser Phe Arg Lys His Val Asp Leu Leu Val Gly Ala Ala Ala Leu
65                  70                  75                  80

Cys Ser Ala Met Tyr Val Gly Asp Leu Cys Gly Gly Val Phe Leu Val
```

```
                    85                  90                  95
Gly Gln Leu Ile Ser Tyr Arg Pro Arg Gln His Ala Thr Val Gln Asp
                100                 105                 110
Cys Asn Cys Ser Ile Tyr Ala Gly His Val Thr Gly His Arg Met Ala
            115                 120                 125
Trp Asp Met Met Asn Trp Ser Pro Thr Val Thr Tyr Leu Val Ser
    130                 135                 140
Ser Ile Leu Arg Ile Pro Gln Ile Leu Ile Asp Ile Phe Val Gly Gly
145                 150                 155                 160
His Trp Gly Val Ile Gly Ala Val Leu Phe Tyr Ser Met Gln Ala Asn
                165                 170                 175
Trp Ala Lys Val Ile Cys
            180

<210> SEQ ID NO 57
<211> LENGTH: 11
<212> TYPE: PRT
<213> ORGANISM: hepatitis C virus

<400> SEQUENCE: 57

Ala Arg Gln Pro Thr Gly Arg His Trp Gly Gln
1               5                   10

<210> SEQ ID NO 58
<211> LENGTH: 12
<212> TYPE: PRT
<213> ORGANISM: hepatitis C virus

<400> SEQUENCE: 58

Val Pro Tyr Ala Asn Lys Ser Gly Ile Tyr His Leu
1               5                   10

<210> SEQ ID NO 59
<211> LENGTH: 11
<212> TYPE: PRT
<213> ORGANISM: hepatitis C virus

<400> SEQUENCE: 59

Ile Tyr Glu Ala Glu Asp Ile Ile Met His Met
1               5                   10

<210> SEQ ID NO 60
<211> LENGTH: 13
<212> TYPE: PRT
<213> ORGANISM: hepatitis C virus

<400> SEQUENCE: 60

Val Leu Val Gly Asn Ile Ser Arg Cys Trp Val Pro Ala
1               5                   10

<210> SEQ ID NO 61
<211> LENGTH: 10
<212> TYPE: PRT
<213> ORGANISM: hepatitis C virus

<400> SEQUENCE: 61

Ile Pro Asn Ala Ser Val Pro Val Arg Ser
1               5                   10

<210> SEQ ID NO 62
<211> LENGTH: 10
<212> TYPE: PRT
```

```
-continued

<213> ORGANISM: hepatitis C virus

<400> SEQUENCE: 62

Arg Pro Arg Gln His Ala Thr Val Gln Asp
1               5                   10

<210> SEQ ID NO 63
<211> LENGTH: 13
<212> TYPE: PRT
<213> ORGANISM: hepatitis C virus

<400> SEQUENCE: 63

Val Thr Tyr Leu Val Ser Ser Ile Leu Arg Ile Pro Gln
1               5                   10
```

HEPATITIS C VIRUS GENOTYPE, AND ITS USE AS PROPHYLACTIC, THERAPEUTIC AND DIAGNOSTIC AGENT

The present application claims benefit of U.S. Provisional Application No. 60/345,642 filed Jan. 8, 2002 and EP 01120969.9 filed Aug. 31, 2001, the entire contents of each of which is incorporated herein by reference.

FIELD OF THE INVENTION

The invention relates to sequences of a new hepatitis C virus (HCV) genotype and its use as prophylactic, therapeutic and diagnostic agent. More specifically, the present invention relates to genomic nucleotide sequences and amino acid sequences corresponding to the non-coding and coding region of this new HCV-type genome.

More particularly, the present invention provides new HCV sequences from until now unknown HCV types and/or subtypes. In particular, the present invention provides new type-specific sequences of the 5' non-coding region (NCR), the Core, the E1 and the NS5 regions of the new HCV type. These new HCV sequences are useful to diagnose the presence of HCV genotypes or serotypes in a biological sample. Moreover, the availability of these new type-specific sequences can increase the overall sensitivity of HCV detection and should also prove to be useful for prophylactic and therapeutic purposes. The current invention thus relates to new HCV sequences, processes for preparing them, and their use for diagnosis, prophylaxis and therapy.

BACKGROUND OF THE INVENTION

Hepatitis C viruses (HCV) have been found to be the major cause of non-A, non-B hepatitis. The sequences of cDNA clones covering the complete genome of several prototype isolates have been determined and include complete prototype genomes of the HCV genotypes 1a (e.g., GenBank accession number AF009606), 1b (e.g., GenBank accession number AB016785), 1c (e.g., GenBank accession number D14853), 2a (e.g., GenBank accession number AB047639), 2b (e.g., GenBank accession number AB030907), 2c (e.g., GenBank accession number D50409) 2k (e.g., GenBank accession number AB031663), 3a (e.g., GenBank accession number AF046866), 3b (e.g., GenBank accession number D49374), 4a (e.g., GenBank accession number Y11604), 5a (e.g., GenBank accession number AF064490), 6a (e.g., GenBank accession number Y12083), 6b (e.g., GenBank accession number D84262), 7b (e.g., GenBank accession number D84263), 8b (e.g., GenBank accession number D84264), 9a (e.g., GenBank accession number D84265), 10a (e.g., GenBank accession number D63821) and 11a (e.g., GenBank accession number D63822). The first complete HCV genomes ever characterized were later classified as HCV genotypes 1a (HCV-1; Choo et al. 1991), 1b (HCV-J; Kato et al. 1990), 2a (HC-J6; Okamoto et al. 1991) and 2b (HC-J8; Okamoto et al. 1992). Comparison of these isolates shows that the variability in nucleotide sequences can be used to distinguish at least 2 different genotypes, type 1 (HCV-1 and HCV-J) and type 2 (HC-J6 and HC-J8), with an average homology of about 68%. Within each type, at least two subtypes exist (e.g. type 1 represented by type 1a HCV-1 and type 1b HCV-J), having an average homology of about 79%. HCV genomes belonging to the same subtype show average homologies of more than 90% (Okamoto et al. 1992). However, the partial nucleotide sequence of the NS5 region of the HCV-T isolates showed at most 67% homology with the previously published sequences, indicating the existence of yet another HCV type (Mori et al. 1992). Parts of the 5' untranslated region (UR, UTR or non-coding region, NCR), core, NS3, and NS5 regions of this type 3 have been published, further establishing the similar evolutionary distances between the 3 major genotypes and their subtypes (Chan et al. 1992). Type 4 was subsequently discovered (Stuyver et al. 1993b; Simmonds et al., 1993a; Bukh et al., 1993; Stuyver et al., 1994a) followed by type 5 (Stuyver et al. 1993b; Simmonds et al. 1993c; Bukh et al. 1993; Stuyver et al. 1994b) and type 6 HCV groups (Bukh et al. 1993; Simmonds et al. 1993c). An overview of the different HCV genotype classification systems used in the past and (part of) the current nomenclature system is given in Table 3. The nomenclature system proposed by the inventors of the present application (Arabic number for major type followed by lower-case Roman letter for each subtype) has now been accepted by scientists worldwide (Simmonds et al. 1994). At the moment, 11 genotypes of HCV are known, which can be classified into 6 Clades. Thus, HCV genotypes 1, 2, 4, and 5 are identified as clades 1, 2, 4 and 5, respectively; HCV genotypes 3 and 10 belong to clade 3; and HCV genotypes 6, 7, 8, 9 and 11 are members of clade 6 (Robertson et al. 1998; see also FIG. 3 of the present invention). The current classification system is based on a threefold hierarchy as will be described in detail furtheron. Basically, the classification system distinguishes, based on percentage of mutual homologies between sequences, between:

HCV isolates belonging to different types;
HCV isolates belonging to the same type but to a different subtype; and
HCV isolates belonging to the same subtype (Maertens and Stuyver 1997).

Nucleic acid and amino acid sequences of HCV genotypes 1 to 11 have been disclosed not only in public databases but also in, e.g., International Patent Publications WO94/12670, WO94/25601, and WO96/13590.

SUMMARY OF THE INVENTION

In one aspect, the current invention relates to a clade 6 HCV genotype comprising an HCV polynucleic acid distinguishable from the HCV polynucleic acids of clade 6 HCV genotypes 6–9 and 11.

In another aspect, the invention more particularly relates to isolated polynucleic acids unique to the HCV genotype according to the invention, or a fragment thereof unique to the HCV genotype according to the invention, or the complement of said polynucleic acid or said fragment. Such isolated polynucleic acids comprise 5'UTR, Core, E1 and NS5B polynucleic acids such as defined by any of SEQ ID NOs:1, 2, 4, 6, 8, 10, 12, 14, 36–47, or 49, as well as homologues thereof. Other polynucleic acids of the invention comprise those nucleic acids encoding Core, E1 and NS5B proteins such as defined by any of SEQ ID NOs:3, 5, 7, 9, 11, 13, 15, 50–61, or 63, as well as homologues thereof.

The invention furthermore covers oligonucleotides consisting of or comprising at least 8 contiguous nucleotides taken from and unique to a HCV polynucleic acid according to the invention. Such oligonucleotides can function for instance as primers capable of specifically amplifying a HCV polynucleic acid according to the invention, as probes capable of specifically hybridizing to a HCV polynucleic acid according to the invention, as oligonucleotides capable of specifically detecting a HCV polynucleic acid according to the invention, or as oligonucleotides capable of determining the genotype of a HCV polynucleic acid according to the invention.

In yet another aspect of the invention, recombinant vectors comprising a HCV polynucleic acid according to the invention are covered. Such vectors can be expression vectors. Host cells comprising a polynucleic acid of the invention or transformed with a recombinant vector of the invention are also covered.

A further aspect of the invention relates to isolated polypeptides unique to the HCV genotype according to the invention, or a fragment thereof unique to the HCV genotype according to the invention. Such polypeptides include those polypeptides as defined by any of SEQ ID NOs:3, 5, 7, 9, 11, 13, 15, 50–61, or 63, as well as homologues thereto. Other polypeptides included are those encoded by, e.g., of SEQ ID NOs:1, 2, 4, 6, 8, 10, 12, 14, 36–47, or 49, and homologues thereof. Methods for producing said polypeptides as well as antibodies to said polypeptides are also embraced by the invention.

Pharmaceutical compositions comprising nucleic acids, polypeptides or antibodies of the invention form another aspect. Such compositions are useful in methods of preventing or treating HCV infection.

Other aspects of the invention include methods and diagnostic kits for detecting the presence of a HCV virus in a biological sample, determining the presence of the genotype of a HCV virus present in a biological sample, determining the presence of HCV antigens or antibodies to HCV in a biological sample, or typing of HCV. Such methods and kits generally rely on an amplification, hybridization, or sequencing reaction for detecting nucleic acids of the invention; or on immunological reaction for detecting polypeptides, antigens or antibodies of the invention.

FIGURE LEGENDS

FIG. 1A is depicting SEQ ID NO:1. SEQ ID NO:1 is the nucleotide sequence of the 5' NCR-region of the HCV isolate obtained from serum sample IG57272 (299 nucleotides). The nucleotide unique to the new HCV type of the invention is black-shadowed box. The positive nucleotide numbering indicated is consistent with the nucleotide numbering used by Kato et al. (1990), i.e. the adenine of the ATG start codon of the HCV polyprotein has nucleotide number 330. The negative nucleotide numbering indicated is consistent with the internationally accepted proposal for HCV nucleotide numbering. Herein, the adenine of the ATG/AUG start codon of the HCV polyprotein has nucleotide number +1 whereas the nucleotide immediately adjacent and upstream of said adenine of the ATG/AUG start codon has nucleotide number −1.

FIG. 1B is depicting SEQ ID NOs:2, 3 and 4. SEQ ID NO:2 is the nucleotide sequence of clone 28454 containing the Core/E1-region of the HCV isolate obtained from serum sample IG57272 (628 nucleotides). SEQ ID NO:3 is the translation of SEQ ID NO:2, the amino acid sequence of clone 28454 containing the Core/E1-region (complete Core and partial E1) of the HCV isolate obtained from serum sample IG57272 (209 amino acids). SEQ ID NO:4 is the nucleotide sequence of clone 28452 containing the partial Core-region of the HCV isolate obtained from serum sample IG57272 (484 nucleotides).

FIG. 1C is depicting SEQ ID NOs:5, 6 and 7. SEQ ID NO:5 is the translation of SEQ ID NO:4, the amino acid sequence of clone 28452 containing the partial Core-region of the HCV isolate obtained from serum sample IG57272 (161 amino acids). SEQ ID NO:6 is the nucleotide sequence of clone 28451 containing the Core/E1-region (complete Core and partial E1) of the HCV isolate obtained from serum sample IG57272 (628 nucleotides). SEQ ID NO:7 is the translation of SEQ ID NO:6, the amino acid sequence of clone 28451 containing the Core/E1-region (complete Core and partial E1) of the HCV isolate obtained from serum sample IG57272 (209 amino acids).

FIG. 1D is depicting SEQ ID NOs:8 and 9. SEQ ID NO:8 is the nucleotide sequence of the NS5B-region of the HCV isolate obtained from serum sample IG57272 (324 nucleotides). SEQ ID NO:9 is the translation of SEQ ID NO:8, the amino acid sequence of the NS5B-region of the HCV isolate obtained from serum sample IG57272 (107 amino acids). The nucleotide numbering indicated for SEQ ID NO:8 is consistent with the nucleotide numbering used by Kato et al. (1990), i.e. the adenine of the ATG start codon of the HCV polyprotein has nucleotide number 330. The amino acid numbering indicated for SEQ ID NO:9 is consistent with the amino acid numbering used by Kato et al. (1990), i.e. the methionine corresponding to the start codon ATG (wherein the adenine has nucleotide number 330) is amino acid number 1 of the HCV polyprotein.

FIGS. 2A and 2B show the alignment of SEQ ID NOs:11, 13, 15, 3, 7 and 5, i.e. the amino acid sequences of the Core/E1 (SEQ ID NOs:11, 13 and 15; all 373 amino acids and SEQ ID NOs:3 and 7; both 209 amino acids, see FIGS. 1B and 1C) and partial Core (SEQ ID NO:5; 161 amino acids, see FIG. 1C) regions of the HCV isolate obtained from serum sample IG57272. The amino acid numbering indicated is consistent with the amino acid numbering used by Kato et al. (1990), i.e. the methionine corresponding to the start codon ATG (wherein the adenine has nucleotide number 330) is amino acid number 1 of the HCV polyprotein. The vertical line between amino acids 191 and 192 indicates the border between the Core and E1 protein. The "Core/E1" region spanning amino acids 17 to 209 (SEQ ID NOs:50, 51 and 52) is indicated between rounded brackets. The amino acids of the V-core region (SEQ ID NO:57) are marked with a '*', those of the V1-region (SEQ ID NO:58) with a '+', those of the V2 region (SEQ ID NO:59) with a '#', those of the V3 region (SEQ ID NO:60) with a '^', those of the V4 region (SEQ ID NO:61) with a '@', those of the V5 region (SEQ ID NO:62) with a '§', and those of the V6 region (SEQ ID NO:63) with a '!'.

Figure 3B:
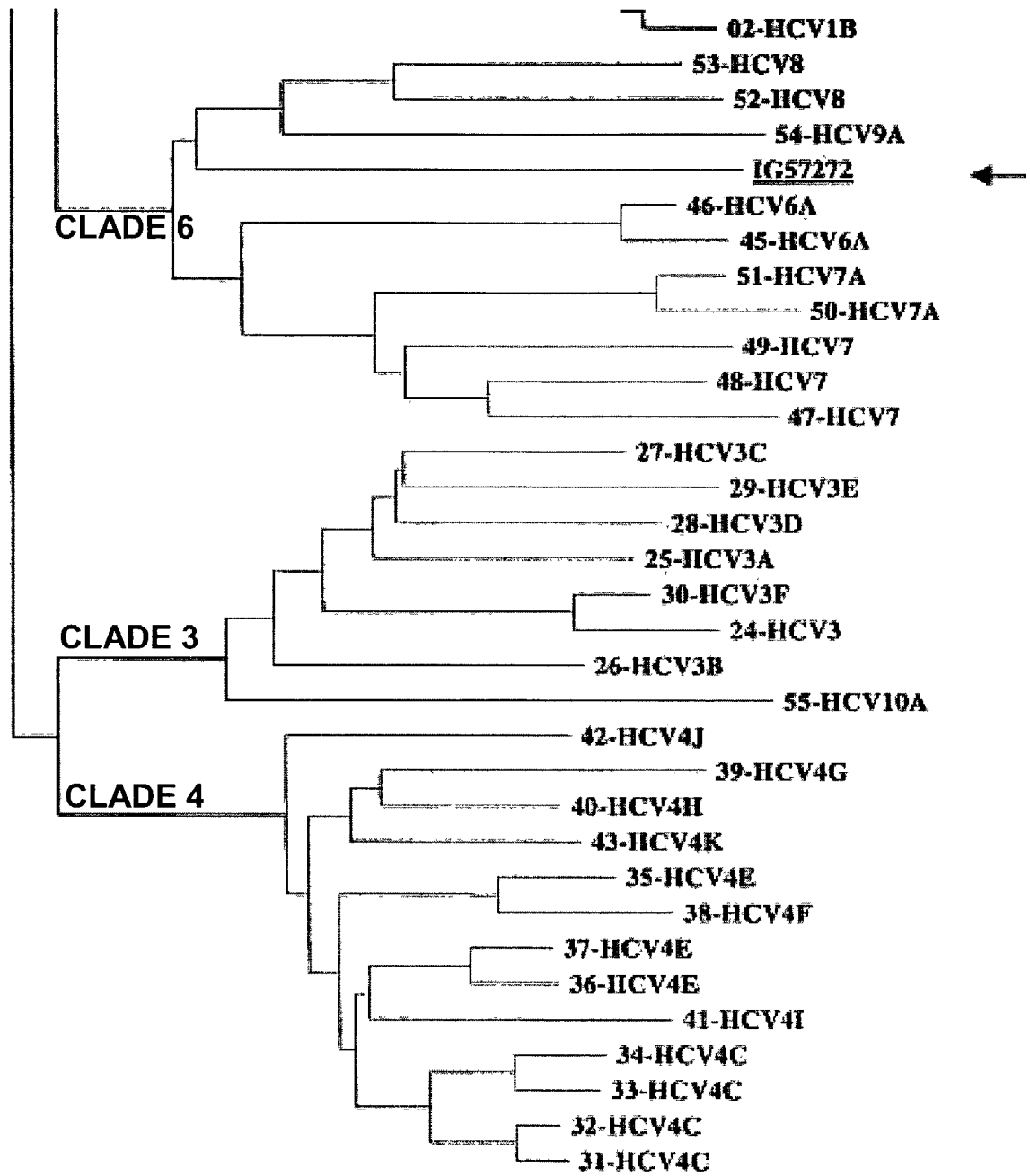

FIGS. 3A and 3B show the phylogenetic tree of NS5B nucleotide sequences of known HCV genotypes (e.g. "18-HCV2C" is a HCV genotype 2c isolate) and of the NS5B nucleotide sequence of the HCV isolate obtained from serum sample IG57272 (underlined and indicated with a left-pointing arrow). Note that the tree has been divided, the bottom two branches of FIG. 3A are repeated as the top two branches of FIG. 3B. The main branches of the phylogenetic tree unifying the HCV genotypes of the different HCV clades (clades 1–6) are indicated.

FIGS. 4A to 4E show the alignment of SEQ ID NOs:10, 12, 14, 2, 4 and 6, i.e. the nucleotide sequences of the Core/E1 (SEQ ID NOs:10, 12 and 14; all 1126 nucleotides) and Core (SEQ ID NOs:2, 4 and 6; see also FIGS. 1B and 1C) regions of the HCV isolate obtained from serum sample IG57272. The HCPr667 and HCPr637 primer sequences (see Example 2) have been removed from SEQ ID NOs:10, 12 and 14. The nucleotide numbering indicated is consistent with the nucleotide numbering used by Kato et al. (1990), i.e. the adenine of the ATG start codon of the HCV polyprotein has nucleotide number 330. Between brackets (FIGS. 4A and 4D) are indicated the Core/E1 regions consisting of nucleotides 378–957 (SEQ ID NOs:36, 37 and 38) of the HCV genome of the current invention (nucleotide numbering consistent with Kato et al. 1990), this region is useful for phylogenetic analysis and phylogenetic classification of HCV genomes.

DETAILED DESCRIPTION OF THE INVENTION

During work leading to the present invention, the LiPA system INNO-LiPA HCV II (see Stuyver et al., 1993b) was used to determine the genotype of HCV viruses present in the sera of HCV-infected patients. A sample from a patient (the HCV species contained therein furtheron referred to as isolate IG57272) was withheld for further analysis because of its aberrant reactivity with the INNO-LiPA HCV II strip. Sequencing results, however, indicated the discovery of a new HCV genotype. Nucleotide sequences in the 5' NCR, Core, Core/E1 and NS5B regions which have not yet been reported before, were analyzed in the frame of the invention. Genomic sequences of this new HCV type are reported for the first time in the present invention.

The present invention thus relates to HCV polynucleic acids, in particular to isolated HCV polynucleic acids, having nucleotide sequences unique to a heretofore unidentified HCV type and thus having nucleotide sequences sufficiently different from prototype polynucleic acid sequences of known HCV types 1, 2, 3, 4, 5, 6, 7, 8, 9, 10, 11 and 12 or any subtype of any thereof (including HCV subtypes 1a, 1b, 1c, 1d, 1e, 1f, 1g, 2a, 2b, 2c, 2d, 2e, 2f, 2g, 2h, 2i, 2k, 2l, 3a, 3b, 3c, 3d, 3e, 3f, 3g, 4a, 4b, 4c, 4d, 4e, 4f, 4g, 4h, 4i, 4j, 4k, 4l, 4m, 5a, 6a, 6b, 7a, 7b, 7c, 7d, 8a, 8b, 8c, 8d, 9a, 9b, 9c, 10a and 11a) to allow classification of the HCV polynucleic acids of the invention, and thus the hepatitis C virus comprising said polynucleic acids, as belonging to a new HCV genotype. Classification of the HCV polynucleic acids of the invention as belonging to a new HCV genotype was established by comparison of a part of the NS5 gene nucleotide sequence, more specifically the nucleotide sequence of the NS5B region, determined for the new HCV type isolated in the present invention, with the corresponding NS5B region sequences of known HCV types or subtypes such as listed above. With "NS5B region" is meant the region of the HCV genome spanning nucleotide positions 8261 to 8600, or more specifically nucleotide positions 8267 to 8590, wherein the nucleotide numbering is consistent with the nucleotide numbering as used by Kato et al. (1990). More particularly, in the HCV genome nucleotide numbering used by Kato et al. (1990), as well as in the present invention, the adenine residue "A" of the ATG start codon encoding the N-terminal methionine of the HCV polyprotein has nucleotide number 330 (see FIG. 2 in Kato et al. 1990). The prototype NS5B nucleotide sequence of the new HCV genotype of the invention is represented by SEQ ID NO:8 and the amino acid sequence derived thereof by SEQ ID NO:9 (FIG. 1D).

Said adenine residue is designated as position 330 at the nucleic acid (HCV genome) level, and said N-terminal methionine is designated as position 1 at the amino acid (HCV polyprotein) level, in the present invention and according to Kato et al. (1990). The term "HCV polyprotein" refers to the HCV protein comprising all of the individual HCV proteins arising from proteolytic processing of the HCV polyprotein precursor. Said individual HCV proteins comprise, listed from the N-terminus to the C-terminus of the HCV polyprotein: Core, E1, E2, p7, NS2, NS3, NS4A, NS4B, NS5A and NS5B. In the HCV-J isolate (Kato et al., 1990), the adenine residue at position 330 (Kato et al., 1990) is the first residue of the ATG codon that initiates the long HCV polyprotein of 3010 amino acids in HCV-J and other type 1b isolates, and of 3011 amino acids in HCV-1 and other type 1a isolates, and of 3033 amino acids in type 2 isolates HC-J6 and HC-J8 (Okamoto et al., 1992). As type 1a isolates contain 1 extra amino acid in the NS5A region, coding sequences of type 1a and 1b have identical numbering in the Core, E1, NS3, and NS4 region, but will differ in the NS5B region as indicated in Table 1. Type 2 isolates have 4 extra amino acids in the E2 region, and 17 or 18 extra amino acids in the NS5 region compared to type 1 isolates, and will differ in numbering from type 1 isolates in the NS3/4 region and NS5b regions as indicated in Table 1. Similar insertions compared with type 1 (but of a different size) can also be observed in type 3a sequences which affect the numbering of type 3a amino acids accordingly. Other insertions or deletions may be readily observed in type 1, 2, 3, 4, 5, 6, 7, 8, 9, 10 and 11 sequences after alignment with known HCV sequences. Genotype-specific genome and polyprotein variations are described for a number of HCV genotypes, including HCV genotypes 1a, 1b, 1c, 2a, 2b, 3a, 3b, 4a, 5a, 6a, 6b, 9a, 10a and 11a, on page 198 and in Table 13.3 of Maertens and Stuyver (1997).

The term "coding region" generally corresponds to a part of a nucleic or polynucleic acid which is encoding a protein, for HCV in particular, the coding region is the region of the HCV genome that encodes the HCV polyprotein. A complete HCV genome is comprising the HCV polyprotein-encoding coding region as well as a 5'-untranslated region and a 3'-untranslated region.

In particular, the new HCV genotype of the present invention is phylogenetically different and clearly distinct from but phylogenetically clustering with, i.e. mostly related to, known HCV genotypes 6, 7, 8, 9 and 11 (FIG. 3). As such, the HCV genotype of the invention is belonging to HCV clade 6 as defined in Robertson et al. (1998). As is obvious from Example 4 and FIG. 3, the HCV genotype of the present invention is phylogenetically sufficiently distinct from the known HCV genotypes of HCV clade 6, hence its classification as a new genotype.

Other isolated HCV polynucleic acids of the current invention include other parts of the new prototype HCV genome. Said parts include nucleic acid sequences covering all or part of the 5' untranslated or nontranslated region (5'UTR, 5'NCR, 5'UR or 5'NR), such as represented by SEQ ID NO:1 or parts thereof (see FIG. 1A); and all or part of the Core and/or Core/E1 and/or E1 region, such as represented by SEQ ID NOs: 2, 4, 6, 10, 12, 14, and 36–49 or parts thereof. The prototype sequences of the new HCV type provided in the description of the present invention enable the man skilled in the art to clone the complete new prototype HCV genome by using common techniques, such as, for example, described in Sambrook et al. 1989. More particularly, commonly known techniques such as gene-walking or isolation of overlapping cDNA clones can be used to obtain a full-length new type HCV genome sequence according to the present invention.

Thus, in one aspect the invention comprises an isolated HCV polynucleic acid of a clade 6 HCV virus of a genotype different from clade 6 HCV genotypes 6–9 and 11, said polynucleic acid characterized in that it is comprising a nucleic acid sequence chosen from any of:

a nucleic acid sequence defined by any of SEQ ID NOs:1, 2, 4, 6, 8, 10, 12, 14, 36–47, or 49;

a 5'UTR nucleic acid sequence comprising, relative to the start codon of the HCV polyprotein coding sequence, an adenine nucleotide at position −159;

a Core nucleic acid sequence at least 85% identical to any of SEQ ID NOs:39–41;

an E1 nucleic acid sequence at least 71% identical to SEQ ID NO:42;

a Core/E1 nucleic acid sequence at least 78% identical to any of SEQ ID NOs:10, 12, 14;

a Core/E1 nucleic acid sequence at least 84% identical to any of SEQ ID NOs:36–38;

an NS5B nucleic acid sequence at least 75% identical to SEQ ID NO:8;

a nucleic acid sequence encoding a HCV polyprotein fragment defined by any of SEQ ID NOs:3, 5, 7, 9, 11, 13, 15, 50–61, or 63;

a nucleic acid sequence encoding a Core protein fragment at least 92% identical to any of SEQ ID NOs:53–55;

a nucleic acid sequence encoding an E1 protein fragment at least 79% identical to SEQ ID NO:56;

a nucleic acid sequence encoding a Core/E1 protein fragment at least 85% identical to any of SEQ ID NOs:11, 13, 15;

a nucleic acid sequence encoding a Core/E1 protein fragment at least 91% identical to any of SEQ ID NOs:50–52;

a nucleic acid sequence encoding an NS5B protein fragment at least 87% identical to SEQ ID NO:9;

a fragment of any of these nucleic acid sequences which is unique to said HCV genotype; or the complement of any of these nucleic acid sequences or of a fragment of any of these nucleic acid sequences which is unique to said HCV genotype.

More specific thereto, the isolated HCV polynucleic acids of the invention can be RNA, DNA, cDNA or a synthetic polynucleic acid.

Another aspect of the invention concerns oligonucleotides comprising or consisting of at least 8 contiguous nucleotides taken from and unique to an isolated HCV polynucleic acid according to the invention. In one embodiment, said oligonucleotide according to the invention is a primer capable of specifically amplifying a HCV polynucleic acid according to the invention. In another embodiment, said oligonucleotide according to the invention is a probe capable of specifically hybridizing to a HCV polynucleic acid according to the invention. In a further embodiment, said oligonucleotide according to the invention is capable of specifically detecting a HCV polynucleic acid according to the invention. In yet another embodiment, said oligonucleotide according to the invention is capable of determining the genotype of a HCV polynucleic acid according the invention. More specifically, the oligonucleotides of the invention can comprise, besides deoxyribonucleic acid monomers, either one or more of a modified nucleotide base, a labeled nucleotide, a modified polynucleotide backbone, a peptide nucleic acid monomer, a locked nucleic acid monomer, and/or a ribonucleic acid monomer.

Said HCV types and subtypes are being classified as in Table 3 by comparison of a part of the NS5 gene nucleotide sequence spanning positions 8261 to 8600, more particularly spanning positions 8267 to 8590, with said amino acid numbering being shown in Table 1, and with said polynucleic acid containing at least one nucleotide differing from said known HCV nucleotide sequences, or the complement thereof. The sequence of known HCV isolates may be found in any nucleotide sequence database known in the art (such as for instance the EMBL or GenBank database; see, e.g., Background of the invention).

The present invention thus also relates to a polynucleic acid having a nucleotide sequence which is unique to the new HCV type according to the invention, with said HCV type being classified as defined herein.

It is to be noted that the nucleotide(s) difference in the polynucleic acids of the invention may result in an amino acid difference in the corresponding amino acid sequences encoded by said polynucleic acids. A composition according to the present invention may contain only polynucleic acid sequences or polynucleic acid sequences mixed with any excipient known in the art for diagnosis, prophylaxis or therapy.

According to a preferred embodiment, the present invention relates to a polynucleic acid encoding an HCV polyprotein comprising in its amino acid sequence at least one unique amino acid residues. With a notation being composed of a letter representing the amino acid residue by its one-letter code, and a number representing the amino acid numbering according to Kato et al. (1980), as shown in Table 1, or a part of said polynucleic acid which is unique to the new HCV type according to the invention as defined in Table 5, and which contains at least one nucleotide differing from known HCV nucleotide sequences, or the complement thereof.

Each of the above-mentioned residues can be found in FIGS. 1, 2 and 4, showing the new nucleic acid and new amino acid sequences of the present invention.

The term "genotype" as used in the present invention refers to both types and/or subtypes.

The term "HCV type" corresponds to a group of HCV isolates of which:

the complete genome nucleic acid sequences show more than 73%, preferably more than 74% mutual homology; or of which the NS5 regions between nucleotide positions 8261 and 8600, or more specifically the regions spanning nucleotides 8267 to 8590, show more than 75.4% mutual homology at the nucleic acid level; or of which the complete HCV polyproteins show more than 78% mutual homology at the amino acid level; or of which the NS5 regions between amino acids at positions 2645 and 2757, or more specifically the regions spanning amino acids 2647 to 2753, show more than 80% mutual homology at the amino acid level;

wherein the nucleotide numbering and amino acid numbering indicated are consistent with the nucleotide numbering and amino acid numbering used by Kato et al. (1990), i.e. the methionine corresponding to the start codon ATG (wherein the adenine has nucleotide number 330) is amino acid number 1 of the HCV polyprotein (see FIG. 2 in Kato et al., 1990).

The term "HCV subtype" corresponds to a group of HCV isolates of which:

the complete genomes or polyproteins show a mutual homology of more than 90%, e.g. 90 to 99% (90%, 91%, 92%, 93%, 94%, 95%, 96%, 97%, 98%, 99%) at the nucleic acid level or of more than 90%, e.g. 95% or 96% (or 90%, 91%, 92%, 93%, 94%, 97%, 98%, 99%) at the amino acid level, respectively; or of which the NS5 regions between nucleotide positions 8261 and 8600, or more specifically the regions spanning nucleotides 8267 to 8590, show a mutual homology of more than 90% at the nucleic acid level;

wherein the nucleotide numbering indicated is consistent with the nucleotide numbering used by Kato et al. (1990), i.e., the adenine residue "A" of the ATG start codon of the HCV polyprotein has nucleotide number 330 (see FIG. 2 in Kato et al. 1990).

distances of less than 0.38, usually of less than 0.37, and more usually of less than 0.364, and isolates belonging to the same subtype show nucleotide distances of less than 0.17, usually of less than 0.16, and more usually of less than 0.15, more usually less than 0.135, more usually less

TABLE 1

Comparison of the HCV nucleotide and amino acid numbering system used in the present invention (*) with the numbering used for other prototype isolates. For example, 8352/8564 indicates the region designated by the numbering from nucleotide 8352 to nucleotide 8564 as described by Kato et al. (1990).

|  | Region | Positions described in the present invention* | Positions described for HCV-J (Kato et al., 1990) | Positions described for HCV-1 (Choo et al., 1991) | Positions described for HC-J6, HC-J8 (Okamoto et al., 1992) |
|---|---|---|---|---|---|
| Nucleotides | NS5B | 8352/8564 | 8352/8564 | 8026/8238 | 8433/8645 |
|  |  | 8261/8600 | 8261/8600 | 7935/8274 | 8342/8681 |
|  |  | 8267/8590 | 8267/8590 | 7941/8264 | 8348/8671 |
|  |  | coding region of present invention | 330/9359 | 1/9033 | 342/9439 |
| Amino Acids | NS5B | 2675/2745 | 2675/2745 | 2676/2746 | 2698/2768 |
|  |  | 2645/2757 | 2645/2757 | 2646/2758 | 2668/2780 |
|  |  | 2647/2753 | 2647/2753 | 2648/2754 | 2670/2776 |

HCV isolates belonging to different types of HCV exhibit mutual homologies, over the complete genome, of less than 74%, preferably less than 73%, at the nucleic acid level and less than 78% at the amino acid level.

HCV isolates belonging to the same HCV type but to different HCV subtypes preferably show homologies of more than 74%, more specifically about 76% to 82% (more particularly of about 77% to 80%) at the nucleic acid level and of more than 78%, more specifically 85–86% at the amino acid level.

More preferably the definition of HCV types is concluded from the classification of HCV isolates according to their nucleotide distances calculated as detailed below:

(1) based on phylogenetic analysis of nucleic acid sequences in the NS5B region between nucleotides 7935 and 8274 (Choo et al., 1991) or 8261 and 8600 (Kato et al., 1990) or 8342 and 8681 (Okamoto et al., 1991), isolates belonging to the same HCV type show nucleotide distances of less than 0.34, usually less than 0.33, and more usually of less than 0.32, and isolates belonging to the same subtype show nucleotide distances of less than 0.135, usually of less than 0.13, and more usually of less than 0.125, usually ranging between 0.0003 and 0.1151, and consequently isolates belonging to the same type but different subtypes show nucleotide distances ranging from 0.135 to 0.34, usually ranging from 0.1384 to 0.2977, and more usually ranging from 0.15 to 0.32, and isolates belonging to different HCV types show nucleotide distances greater than 0.34, usually greater that 0.35, and more usually of greater than 0.358, more usually ranging from 0.3581 to 0.6670.

(2) based on phylogenetic analysis of nucleic acid sequences in the core/E1 region between nucleotides 378 and 957, isolates belonging to the same HCV type show nucleotide than 0.134, and consequently isolates belonging to the same type but different subtypes show nucleotide distances ranging from 0.15 to 0.38, usually ranging from 0.16 to 0.37, and more usually ranging from 0.17 to 0.36, more usually ranging from 0.133 to 0.379, and isolates belonging to different HCV types show nucleotide distances greater than 0.34, 0.35, 0.36, usually more than 0.365, and more usually of greater than 0.37, In a comparative phylogenetic analysis of available sequences, ranges of molecular evolutionary distances for different regions of the genome were calculated, based on 19,781 pairwise comparisons by means of the DNADIST program of the phylogenic inference package PHYLIP version 3.5 c (Felsenstein, 1993). The results are shown in Table 2 and indicate that although the majority of distances obtained in each region fit with classification of a certain isolate, only the ranges obtained in the 340 bp NS5B-region are non-overlapping and therefore conclusive. However, as was performed in the present invention, it is preferable to obtain sequence information from at least 2 regions before final classification of a given isolate.

Designation of a number to the different types of HCV and HCV nomenclature is based on chronological discovery of the different types. The numbering system used in the present invention might still fluctuate according to international conventions or guidelines. For example, "type 12" might be changed into "type 7" or "type 9". Also the arbitrarily chosen border distances between types and subtypes and isolates may still be subject to change according to international guidelines or conventions. Therefore types 7a, 8a, 8b, 9a may for example be designated 6b, 6c, 6d, and 6d in the future; and type 10a which shows relatedness with genotype 3 may be denoted 3g instead of 10a.

TABLE 2

Figures created by the PHYLIP program DNADIST are expressed as minimum to maximum (average ± standard deviation). Phylogenetic distances for isolates belonging to the same subtype ('isolates'), to different subtypes of the same type ('subtypes'), and to different types ('types') are given.

| Region | Core/E1 579 bp | E1 384 bp | NS5B 340 bp | NS5B 222 bp |
|---|---|---|---|---|
| Isolates* | 0.0017 – 0.1347 (0.0750 ± 0.0245) | 0.0026 – 0.2031 (0.0969 ± 0.0289) | 0.0003 – 0.1151 (0.0637 ± 0.0229) | 0.000 – 0.1323 (0.0607 ± 0.0205) |
| Subtypes* | 0.1330 – 0.3794 (0.2786 ± 0.0363) | 0.1645 – 0.4869 (0.3761 ± 0.0433) | 0.1384 – 0.2977 (0.2219 ± 0.0341) | 0.117 – 0.3538 (0.2391 ± 0.0399) |
| Types* | 0.3479 – 0.6306 (0.4703 ± 0.0525) | 0.4309 – 0.9561 (0.6308 ± 0.0928) | 0.3581 – 0.6670 (0.4994 ± 0.0495) | 0.3457 – 0.7471 (0.5295 ± 0.0627) |

It is to be understood that extremely variable regions such as the E1, E2 and NS4 regions will exhibit lower homologies than the average homology of the complete genome of the polyprotein.

Using these criteria, HCV isolates can be classified into at least 11 types. Several subtypes can clearly be distinguished in types 1, 2, 3, 4 and 7: 1a, 1b, 1c, 1d, 1e, 1f, 1g, 2a, 2b, 2c, 2d, 2e, 2f, 2g, 2h, 2i, 2k, 2l, 3a, 3b, 3c, 3d, 3f, 3g, 4a, 4b, 4c, 4d, 4e, 4f, 4g, 4h, 4i, 4j, 4k, 4l, 4m, 7a, 7c, and 7d based on homologies of the 5' NCR and coding regions. An overview of most of the reported isolates and their proposed classification according to the typing system of the present invention as well as other proposed classifications is presented in Table 3.

The term "polynucleic acid" refers to a single-stranded or double-stranded nucleic acid sequence which may contain at least 5 contiguous nucleotides (e.g. at least 6, 7, 8, 9, 10, 11, 12, 13, 14, 15, 16, 17, 18, 19, 20, 21, 22, 23, 24, 25, 30, 35, 40, 45, 50, 60, 70, 75, 80, 85, 90, 95, 100 or more contiguous nucleotides). A polynucleic acid which is up till about 100 nucleotides in length is often also referred to as an oligonucleotide. A polynucleic acid may consist of deoxyribonucleotides or ribonucleotides, nucleotide analogues or modified nucleotides, or may have been adapted for therapeutic purposes. A polynucleic acid may also comprise a double stranded cDNA clone which can be used for cloning purposes, or for in vivo therapy, or prophylaxis.

The oligonucleotides according to the present invention, used as primers or probes may also contain or consist of nucleotide analogous such as phosphorothioates (Matsukura et al., 1987), alkylphosphoriates (Miller et al., 1979) or peptide nucleic acids (Nielsen et al., 1991, 1993) or may contain intercalating agents (Asseline et al., 1984).

As most other variations or modifications introduced into the original DNA sequences of the invention these variations will necessitate adaptations with respect to the conditions under which the oligonucleotide should be used to obtain the required specificity and sensitivity. However, the eventual results will be essentially the same as those obtained with the unmodified oligonucleotides. The introduction of these modifications may be advantageous in order to positively influence characteristics such as hybridization kinetics, reversibility of the hybrid-formation, biological stability of the oligonucleotide molecules, etc.

The polynucleic acids of the invention may be comprised in a composition of any kind. Said composition may be for diagnostic, therapeutic or prophylactic use.

The term "complement" refers to a nucleotide sequence which is complementary to an indicated sequence and which is able to hybridize to the indicated sequences.

The composition of the invention can comprise many combinations. By way of example, the composition of the invention can comprise:

two (or more) nucleic acids from the same region or, two nucleic acids (or more), respectively from different regions, for the same isolate or for different isolates, or nucleic acids from the same regions and from at least two different regions (for the same isolate or for different isolates).

The expression "sequence which is unique to a HCV type of the present invention" refers to a sequence which is not shared by any other type or subtype of HCV, and can thus be used to uniquely detect a HCV type according to the present invention. Sequence variability is demonstrated in the present invention between clones of the newly found HCV type of the invention (see FIGS. 2 and 4). Similarly, sequence variability between the newly identified HCV type of the invention with the known HCV types and subtypes, e.g. HCV types 1–12 sequences can be determined by the man skilled in the art using common techniques, such as described in examples 3 and 4, without undue burden or inventivity. It is therefore from these regions of sequence variability in particular that type- or subtypes-specific polynucleic acids, oligonucleotides, polypeptides and peptides may be obtained. The term type- or subtype-specific refers to the fact that a sequence is unique to that particular HCV type or subtype involved.

The expression "nucleotides corresponding to" refers to nucleotides which are homologous or complementary to an indicated nucleotide sequence or region within a specific HCV sequence.

TABLE 3

Overview of several known HCV types and subtypes classified according to the different authors. (Okamoto et al. 1992; Mori et al. 1992; Cha et al. 1992; Nakao et al. 1991)

HCV CLASSIFICATION

| | OKAMOTO | MORI | CHA | NAKAO | PROTOTYPE |
|---|---|---|---|---|---|
| 1a | I | I | Pt | GI | HCV-1, HCV-H, HC-J1 |
| 1b | II | II | KI | GII | HCV-J, HCV-BK, HCV-T, HC-JK1, HC-J4, HCV-CHINA |
| 1c | | | | | HC-G9 |
| 2a | III | III | K2a | GIII | HC-J6 |
| 2b | IV | IV | K2b | GIII | HC-J8 |
| 2c | | | | | S83, ARG6, ARG8, I10, T983 |
| 2d | | | | | NE92 |
| 3a | V | V | K3 | GIV | BR36, BR56, HD10, N2L1, BR33, Ta, E-b1 |
| 3b | | VI | K3 | GIV | HCV-TR, Tb, NE137 |
| 3c | | | | | NE48 |
| 3d | | | | | NE274 |
| 3e | | | | | NE145 |
| 3f | | | | | NE125 |
| 4a | | | | | Z4, GB809-4 |
| 4b | | | | | Z1 |
| 4c | | | | | GB116, GB358, GB215, Z6, Z7 |
| 4d | | | | | DK13 |
| 4e | | | | | GB809-2, CAM600, CAM736 |
| 4f | | | | | CAM622, CAM627 |
| 4g | | | | | GB549 |
| 4h | | | | | GB438 |
| 4i | | | | | CAR4/1205 |
| 4j | | | | | CAR1/905 |
| 5a | | | | GV | SA3, SA4, SA1, SA7, SA11, BE95 |
| 6a | | | | | HK1, HK2, HK3, HK4, VN11 |

A "HCV polynucleic acid" or, in particular, an "isolated HCV polynucleic acid" is meant to comprise single-stranded polynucleic acids, double-stranded polynucleic acids or triplex-forming polynucleic acids obtained directly from a sample or obtained after duplication, multiplication or amplification. "Obtained" is, in the present context, meant to include isolation and/or purification and/or amplification of said polynucleic acids from a biological sample. The "sample" may be any biological material taken either directly from an infected human being (or animal), or after culturing (enrichment). Biological material may be e.g. expectorations of any kind, broncheolavages, blood, skin tissue, biopsies, sperm, lymphocyte blood culture material, colonies, liquid cultures, faecal samples, urine etc. Biological material may also be artificially infected cell cultures or the liquid phase thereof. The term "biological sample" generally refers to any biological sample (tissue or fluid) containing HCV nucleic acid sequences and refers more particularly to blood serum or plasma samples. "Duplication, multiplication or amplification" is meant to include any nucleic acid amplification method producing a nucleic acid including, said amplification methods also including sequencing. Thus, any sequencing technique producing a nucleic acid molecule comprising part or all of the HCV nucleic acids according to the present invention is to be understood to be comprised in the term "duplication, multiplication or amplification".

In particular, a "polynucleic acid" generally may contain at least, or up to, 5 contiguous nucleotides (e.g., at least, or up to, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 or more contiguous nucleotides). A polynucleic acid which is up to about 200 nucleotides in length is often also referred to as an oligonucleotide.

The present invention clearly relates to any method for preparing a polynucleic acid according to the present invention, resulting in a synthetic polynucleic acid.

The term "synthetic polynucleic acid" as referred to herein is meant to be a single-stranded polynucleic acid, double-stranded polynucleic acid or triplex-forming polynucleic acid. Polynucleic acids can be made in vitro by means of a nucleotide sequence amplification method. If such an amplified polynucleic acid is double-stranded, conversion to a single-stranded molecule can be achieved by a suitable exonuclease given that the desired single-stranded polynucleic acid is protected against said exonuclease activity. Alternatively, polynucleic acid are derived from recombinant plasmids containing inserts including the corresponding polynucleotide sequences, if need be by cleaving the latter out from the cloned plasmids upon using the adequate nucleases and recovering them, e.g. by fractionation according to molecular weight. Alternatively, polynucleic acids may be isolated fragments of naturally occurring or cloned DNA or RNA or cDNA. Another means of making a synthetic polynucleic acid in vitro is comprised within any method of nucleic acid sequencing. Products of a sequencing reaction are thus clearly covered by the term "synthetic polynucleic acid". The polynucleic acids according to the present invention can also be synthesized chemically, for instance by applying the conventional phospho-diester (Agarwal et al. 1976) or -triester (Hsiung et al. 1979) chemistry or phosphoramidite chemistry (Beaucage et al. 1981). The polynucleic acids may be synthesized automatically on commercial instruments sold by a variety of manufacturers.

"Nucleotide sequence (DNA or RNA) amplification" is meant to include all methods resulting in multiplication of the number of target nucleotide sequence copies. Nucleotide sequence amplification methods include the polymerase chain reaction (PCR; DNA amplification), strand displacement amplification (SDA; DNA amplification), transcription-based based amplification system (TAS; RNA amplification), self-sustained sequence replication (3SR; RNA amplification), nucleic acid sequence-based amplification (NASBA; RNA amplification), transcription-mediated amplification (TMA; RNA amplification), Qbeta-replicase-mediated amplification and run-off transcription. During amplification, the amplified products can be conveniently labeled either using labeled primers or by incorporating labeled nucleotides. Labels may be isotopic ($^{32}P$, $^{35}S$ etc.) or non-isotopic (biotin, digoxigenin, etc.).

The most widely spread nucleotide sequence amplification technique is PCR. Basically, two primers, a sense and an antisense are annealed to a denatured DNA substrate and extended by a thermostable DNA polymerase. The latter allows rapid and repeated thermal cycling (denaturing/annealing/extension in three-step PCR; denaturing/annealing+extension in two-step PCR). The target DNA is exponentially amplified. The amplification reaction is repeated between 20 and 70 times, advantageously between 25 and 45 times. Many methods rely on PCR including AFLP (amplified fragment length polymorphism), IRS-PCR (interspersed repetitive sequence PCR), iPCR (inverse PCR), RAPD (rapid amplification of polymorphic DNA), RT-PCR (reverse transcription PCR) and real-time PCR. Some of the latter methods are explained in more detail infra. RT-PCR can be performed with a single thermostable enzyme having both reverse transcriptase and DNA polymerase activity (Myers et al., 1991). Alternatively, a single tube-reaction with two enzymes (reverse transcriptase and thermostable DNA polymerase) is possible (Cusi et al., 1994).

SDA is, contrary to PCR, an isothermal DNA replication method. Sense and antisense primers used in this method have a 5'-terminal overhang comprising a restriction enzyme recognition site. Both primers are extended by the Klenow polymerase in the presence of an alpha-S-dNTP. The resulting hemiphosphorothiolated dsDNA is subsequently nicked in the unmodified strand (ss-nick) by the restriction enzyme. This enables the Klenow polymerase to extend the resulting primer fragments thereby displacing the downstream non-template strand (Walker et al., 1992).

In TAS, a first sense primer comprising at its 5' end a promoter recognized by a DNA-dependent RNA polymerase (such as bacteriophage T7, T3 or SP6 RNA polymerase) and a second antisense primer complementary to the 3' end of the RNA to be amplified are used to prime reverse transcription. After denaturation and reannealing of the primers another round of reverse transcription can take place and the ssDNA strands formed in the first RT reaction either used as a substrate for RT or anneal, in both cases forming a dsDNA comprising the intact DNA-dependent RNA polymerase promoter. Formation of said intact promoter allows transcription and synthesis of multiple copies of the original target RNA (Kwoh et al., 1989).

3SR is based on a similar principle as TAS but both primers now carry the same DNA-dependent RNA polymerase promoter. Furthermore, after RT, the RNA/DNA hybrid is converted into ssDNA by means of RNAseH. Denaturation is thus not longer required which also alleviates the need to add fresh reverse transcriptase enzyme after each round of denaturation. 3SR thus is an isothermal variant of TAS (Gingeras et al., 1990).

NASBA is a hybrid between TAS and 3SR using a single primer including the DNA-dependent RNA polymerase promoter and using RNAseH (Kievits et al., 1991).

TMA is similar to NASBA but has ribosomal RNA as template. Detection of the amplified rRNA sequences is achieved by chemiluminescence detection of amplicons with an acridium ester-labeled DNA probe in the hybridization protection assay (HPA) (Stary et al., 1998).

Qbeta-replicase-mediated amplification is based on the capability of the RNA-directed RNA polymerase of phage Qbeta to isothermally amplify RNA in vitro. RNAs heterologous to the Qbeta phage can be amplified by coupling them to cognate RQ RNAs (Lizardi et al., 1988).

Run-off transcription is a method commonly used in e.g. the preparation of riboprobes or RNA probes. The DNA of interest is placed behind the promoter recognized by a DNA-dependent RNA polymerase (e.g. T3, T7, SP6 RNA polymerase), e.g. by cloning in a suitable vector. The DNA of interest is furthermore digested with a restriction enzyme at a suitable site such that the desired riboprobe can be synthesized by the RNA polymerase. When said RNA polymerase reaches the digested end of the DNA, it runs off the substrate and is available for a new round of RNA synthesis.

The terms "polynucleotide", "polynucleic acid", "nucleic acid sequence", "nucleotide sequence", "nucleic acid molecule", "oligonucleotide", "probe" or "primer", when used herein refer to nucleotides, either ribonucleotides, deoxyribonucleotides, peptide nucleotides or locked nucleotides, or a combination thereof, in a polymeric form of any length or any shape (e.g. branched DNA). Said terms furthermore include double-stranded (ds) and single-stranded (ss) polynucleotides as well as triple-stranded polynucleotides. Said terms also include known nucleotide modifications such as methylation, cyclization and 'caps' and substitution of one or more of the naturally occurring nucleotides with an analog such as inosine or with nonamplifiable monomers such as HEG (hexethylene glycol). Ribonucleotides are denoted as NTPs, deoxyribonucleotides as dNTPs and dideoxyribonucleotides as ddNTPs. Nucleotides can generally be labeled radioactively, chemiluminescently, fluorescently, phosphorescently or with infrared dyes or with a surface-enhanced Raman label or plasmon resonant particle (PRP).

Modifications of nucleotides include any modification of the polynucleotide backbone and/or nucleotide base and addition of any atom of molecule to the polynucleotide backbone and/or nucleotide base. With "nucleotide base" is meant the pyrimidine or purine part of a nucleotide. With "backbone" is meant the structure forming a polynucleotide and to which the nucleotide bases are attached; generally said backbone comprises a sugar moiety (e.g., ribose or deoxy-ribose) and phosphate. Yet another modification is the presence of intercalating agents in a nucleic acid molecule.

Further modifications of polynucleotides include hapten- or protein-labeling. Haptens include e.g. biotin and digoxigenin whereas proteins include enzymes such as soybean or horseradish peroxidase, beta-galactosidase, luciferase, alkaline phosphatase, glutathione S-transferase or dihydrofolate reductase or may constitute heterologous epitopes such as (histidine)$_6$-tag, protein A, maltose-binding protein, epitopes such as Tag•100, c-myc, FLAG®, HA, protein C or VSV; or lacZ, CMP (calmodulin-binding peptide). Other proteins include histones, single-strand binding protein (ssB) and native and engineered fluorescent proteins such as green-, red-, blue-, yellow-, cyan-fluorescent proteins. Crosslinking moieties can also be incorporated such as coumarins, furocoumarins or benzodipyrones, or derivates of any thereof.

Said terms "polynucleotide", "polynucleic acid", "nucleic acid sequence", "nucleotide sequence", "nucleic acid molecule", "oligonucleotide", "probe" or "primer" also encompass peptide nucleic acids (PNAs), a DNA analogue in which the backbone is a pseudopeptide consisting of N-(2-aminoethyl)-glycine units rather than a sugar. PNAs mimic the behavior of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors. PNA probes can generally be shorter than DNA probes and are generally from 6 to 20 bases in length and more optimally from 12 to 18 bases in length (Nielsen, 2001). Said terms further encompass locked nucleic acids (LNAs) which are RNA derivatives in which the ribose ring is constrained by a methylene linkage between the 2'-oxygen and the 4'-carbon. LNAs display unprecedented binding affinity towards DNA or RNA target sequences. LNA nucleotides can be oligomerized and can be incorporated in chimeric or mix-meric LNA/DNA or LNA/RNA molecules. LNAs seem to be nontoxic for cultured cells. (Orum et al., 2001; Wahlestedt et al., 2000). In general, chimeras or mix-mers of any of DNA, RNA, PNA and LNA are considered as well as any of these wherein thymine is replaced by uracil.

The present invention relates particularly to a polynucleic acid as defined herein having a sequence selected from any of SEQ ID NOs:1, 2, 4, 6, 8, 10, 12, 14, or 36–49 or a part of said polynucleic acid which is unique to any of the HCV subtypes or types as defined in Table 5, and which contains at least one nucleotide differing from known HCV polynucleic acids, or the complement thereof.

The present invention relates more particularly to a polynucleic acid of the new HCV according to the invention and as defined herein, which codes for the 5' NCR, the Core/E1, or the NS5B region or a part thereof.

More particularly, the present invention relates to a polynucleic acid as defined herein which is a cDNA sequence.

Also included within the present invention are sequence variants of the polynucleic acids as selected from any of the nucleotide sequences as given in any of the above given SEQ ID numbers with said sequence variants containing either deletion and/or insertions of one or more nucleotides, especially insertions or deletions of 1 or more codons, mainly at the extremities of oligonucleotides (either 3' or 5'), or substitutions of some non-essential nucleotides (i.e. nucleotides not essential to discriminate between different genotypes of HCV) by others (including modified nucleotides an/or inosine), for example, a type 1 or 2 sequence might be modified into a type 7 sequence by replacing some nucleotides of the type 1 or 2 sequence with type-specific nucleotides of type 7.

Particularly preferred variant polynucleic acids of the present invention include also sequences which hybridize under stringent conditions with any of the polynucleic acid sequences of the present invention. Particularly, sequences which show a high degree of homology (similarity) to any of the polynucleic acids of the invention as described herein are preferred. Even more particularly, sequences which are at least 80%, 81%, 82%, 83%, 84%, 85%, 86%, 87%, 88%, 89%, 90%, 91%, 92%, 93%, 94%, 95% or more homologous to said polynucleic acid sequences of the invention are contemplated. Preferably said sequences will have less than 20%, 15%, 10%, or 5% variation compared to the original nucleotides of said polynucleic acid sequence.

More specifically, with a sequence being more than nn % homologous or identical to a given reference sequence is meant that said sequence is more than nn %, (nn+0.5)%, (nn+1)%, (nn+1,5)% to 99% homologous or identical, respectively, to said given reference sequence. Thus, if nn=80, than said sequence is at least 80%, 80.5%, 81%, 81.5%, 82%, 83%, 84%, 85%, 86%, 87%, 88%, 89%, 90%, 91%, 92%, 93%, 94%, 95%, 96%, 97%, 98%, or at least 99% homologous or identical, respectively, to said given reference sequence. In another example, wherein nn=87, said sequence is at least 87%, 87.5%, 88%, 88.5%, 89%, 90%, 91%, 92%, 93%, 94%, 95%, 96%, 97%, 98%, or at least 99% homologous or identical, respectively, to said given reference sequence. With "reference sequence" is meant herein the sequence (nucleic acid or amino acid) to which another sequence is compared, e.g. for the sake of making sequence alignment or determining % homologies or identities. For the new HCV polynucleic acid and amino acid sequences according to the invention, Table 6 is giving an overview of said sequences as well as the percentages identity homologous HCV polynucleic acids and amino acids need to have to fall within the scope of the invention. Thus, if a given HCV sequence is at least nn % identical as indicated in Table 6 to a reference prototype HCV sequence according to the invention (see definition of nn % identity above), then said given HCV sequence falls within the scope of the invention. Likewise, Tables 7 and 8 give an overview of some fragments of the HCV polynucleic acid sequences (E1 and NS5B, respectively) according to the invention as well as the percentages identity homologous HCV polynucleic acid fragments need to have to fall within the scope of the invention. As will be obvious from Tables 7 and 8, some fragments comprise regions which are more conserved among HCV isolates of different genotypes. This is reflected in the higher required % identity a given HCV nucleic acid fragment needs to have with a fragment as indicated in Tables 7 and 8 to fall within the scope of the invention.

Polynucleic acid sequences according to the present invention which are homologous to the sequences as represented by SEQ ID NOs:1, 2, 4, 6, 8, 10, 12, 14, or 36–49, can be characterized and isolated according to any of the techniques known in the art, such as amplification by means of sequence-specific primers, hybridization with sequence-specific probes under more or less stringent conditions, serological screening methods or via the LiPA typing system.

Other preferred variant polynucleic acids of the present invention include sequences which are redundant as a result of the degeneracy of the genetic code compared to any of the above-given polynucleic acids of the. present invention. These variant polynucleic acid sequences will thus encode the same amino acid sequence as the polynucleic acids they are derived from.

Also included within the scope of the present invention are 5' non-coding region sequences which can be readily obtained from the new HCV type isolates described herein, such as, for example represented by SEQ ID NO:1. Such sequences may contain type or subtype-specific motifs which can be employed for type and/or subtype-specific hybridization assays, e.g. such as described by Stuyver et al. (1993).

In particular, SEQ ID NO:1 is comprising in its nucleotide sequence the nucleotide residue adenine at position 171 ("A171") of the 5'UTR, with the number representing the nucleotide numbering as shown in FIG. 1A. Nucleotide A171 is specific for the 5'UTR of the new HCV genotype according to the present invention. Nucleotide A171 may alternatively be assigned the number −159 wherein this nucleotide number is relative to the first adenine of the AUG/ATG start codon of the HCV polyprotein, i.e., said first adenine of the start codon then has nucleotide number +1 whereas the nucleotide immediately adjacent and upstream of said first adenine has nucleotide number −1. Polynucleic acid sequences of the genomes indicated herein from regions not yet depicted in the present examples, figures and sequence listing can be obtained by any of the techniques known in the art, such as amplification techniques using suitable primers from the sequences of these new genomes given in FIGS. 1 and 4 of the present invention.

The present invention also relates to an oligonucleotide primer comprising part of a polynucleic acid as defined herein, with said primer being able to act as a primer for specifically amplifying the nucleic acid of a certain HCV isolate belonging to the new HCV genotype according to the invention from which the primer is derived.

The term "primer" refers to a single stranded DNA oligonucleotide sequence capable of acting as a point of initiation for synthesis of a primer extension product which is complementary to the nucleic acid strand to be copied. The length and the sequence of the primer must be such that it allows priming of the synthesis of an extension product. Preferably, the primer is about 5–50 nucleotides. Specific length and sequence will be dependent on the complexity of the required DNA or RNA targets, as well as on the conditions of primer use such as temperature and ionic strength. Thus, a primer can be, e.g., 5, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45 or 50 nucleotides in length.

The fact that amplification primers do not have to match exactly with corresponding template sequence to warrant proper amplification is amply documented in the literature (Kwok et al., 1990).

The present invention also relates to an oligonucleotide probe comprising part of a polynucleic acid as defined herein, with said probe being able to act as a hybridization probe for specific detection and/or classification into types and/or subtypes of an HCV nucleic acid containing said nucleotide sequence, with said probe being optionally labeled or attached to a solid substrate.

The term "probe" refers to single stranded sequence-specific oligonucleotides which have a sequence which is complementary to the target sequence of the HCV genotype(s) to be detected. Preferably, these probes are about 5 to 50 nucleotides long, more preferably from about 10 to 25 nucleotides. Thus, a probe can be, e.g., 5, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45 or 50 nucleotides in length.

Primers and probes as described above may furthermore comprise modified nucleotide bases and/or a modified polynucleotide backbone and/or peptide nucleic acids and/or locked nucleic acids and/or labeled nucleotides and/or nucleotides carrying a hapten or protein, all as described above.

Furthermore, an oligonucleotide according to the present invention may further comprise a modification for attaching said oligonucleotide to a solid support.

Said modification may for instance be an amine-, thiol-, 3-'propanolamine or Acrydite-modification of the oligonucleotide or may comprise the addition of a homopolymeric tail (e.g. an oligo(dT)-tail added enzymatically via a terminal transferase enzyme or added synthetically) to the oligonucleotide. If said homopolymeric tail is positioned at the 3'-terminus of the oligonucleotide or if any other 3'-terminal modification preventing enzymatic extension is incorporated in the oligonucleotide, the priming capacity of the oligonucleotide can be decreased or abolished. Other modifications are described in e.g. (Beaucage, 2001).

The term "solid support" can refer to any substrate to which an oligonucleotide probe can be coupled, provided that it retains its hybridization characteristics and provided that the background level of hybridization remains low. Usually the solid substrate will a microsphere (bead), a nitrocellulose or nylon membrane, a glass slide or fused silica (quartz) slide (the latter known as nucleic acid arrays or microarrays or as nucleic acid chips), a gold film, a polypyrrole film, an optical fiber or in e.g. a polyacrylamide gel or a microplate well. Prior to application to the solid support or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin or haptens.

The present invention also relates to a diagnostic kit for use in determining the genotype of HCV, said kit comprising a primer as defined herein.

The present invention also relates to a diagnostic kit for use in determining the genotype of HCV, said kit comprising a probe as defined herein.

The present invention also relates to a diagnostic kit as defined herein, wherein said probe(s) is(are) attached to a solid substrate.

The present invention also relates to a diagnostic kit as defined herein, wherein a range of said probes is attached to specific locations on a solid substrate.

The present invention also relates to a diagnostic kit as defined herein, wherein said solid support is a membrane strip and said probes are coupled to the membrane in the form of parallel lines.

The present invention relates furthermore to method for the detection of nucleic acids of the new HCV type of the invention.

A large number of assays capable of detecting nucleotide sequences and nucleotide sequence polymorphisms is currently available. These assays can identify specific mutations, single nucleotide polymorphisms (SNPs), genotype-specific nucleotides or the like. Some of these assays are based on physical methods whereas others use enzymatic approaches.

With "physical detection methods" is meant in the present context methods of nucleotied sequence polymorphism detection that require one or more physical processes for detection although not excluding the enzymatic process of prior PCR amplification of the target DNA sequence comprising one or more nucleotide sequence polymorphisms. Said physical processes include electrophoresis, chromatography, spectrometry, optical signal sensing and spectroscopy.

Physical nucleotide sequence polymorphism detection assays include electrophoretic methods such as SSCP, CDCE, CDGE, DGGE, TGGE, DGCE, nonisocratic CZE, TDGS, CSGE, MADGE and DSCA; chromatographic methods include DHPLC. Physical nucleotide sequence polymorphism detection assays may be effective for identification of known or new mutations and may require confirmation by direct DNA sequencing.

Single stranded conformation polymorphism (SSCP) is based on differences in mobility due to changes in sequence-dependent secondary and ternary structures of single stranded DNA. Critical for SSCP are the experimental conditions comprising gel temperature and gel composition. SSCP is a well-established and widely used assay reliable for DNA fragments having a size of or below 200 basepairs (bp). SSCP assays can be run in a gel or capillary electrophoresis format and can be combined with fluorescence-based detection of the ssDNAs (Kristensen et al., 2001; Nishimura et al., 2000; Bosserhoff et al., 1999; Iwahana et al., 1996; Bosserhoff et al., 1999; Bosserhoff et al., 1999; Bosserhoff et al., 1999).

Constant denaturant capillary electrophoresis (CDCE) and constant denaturant gel electrophoresis (CDGE) are both based on differences in electrophoretic mobility between homo- and heteroduplex DNA molecules. Said differences in mobility depend on the differences in melting characteristics of said DNA duplexes. The melting of target DNA duplexes in CDCE and CDGE is implemented by using a zone of constant temperature and constant denaturant composition in the gel or capillary. CDCE and CDGE can be combined with fluorescence detection of the DNA molecules. CDCE can also be applied in the enrichment of rare mutants. The target DNA duplexes in CDCE and CDGE are typically 80 to 200 bp long (Khrapko et al., 2001; Kristensen et al., 2001; Li-Sucholeiki et al., 2000; Khrapko et al., 1997; Khrapko et al., 1994; Khrapko et al., 1997; Khrapko et al., 1994). In denaturing gradient gel electrophoresis (DGGE), melting of the target duplex DNA molecules is achieved by a low to high denaturant gradient in the polyacrylamide gel. In temperature gradient gel electrophoresis, said melting is achieved by a low to high temperature gradient. In double gradient capillary electrophoresis (DGCE), melting of the target homo- and heteroduplex DNA molecules is achieved by a chemical or thermal gradient and separated homo- and heteroduplex DNA is subsequently recompacted in a colinear second porosity gradient. Capillary zone electrophoresis (CZE) is also known as free-solution capillary electrophoresis (FSCE). Nonisocratic CZE, or thermal gradient capillary electrophoresis (TGCE), wherein a temperature gradient is generated internally in the capillary, can be used to separate target DNA homo- and heteroduplex molecules (Kristensen et al., 2001; Righetti et al., 1997; Kristensen et al., 2001). Two-dimensional gene scanning (TDGS) involves two-dimensional DNA electrophoresis comprising size separation in a first step and DGGE in a second step. TDGS allows detection of nucleotide polymorphisms in a set of target duplex DNAs of different size, e.g. obtained in a multiplex PCR reaction (Vijg et al., 1999). Addition of a GC-clamp (an artificial high-melting domain) to the end of a DNA fragment (incorporated via, e.g., a PCR primer) permits analysis of almost any DNA sequence in denaturing-based electrophoretic methods for detection of nucleotide polymorphisms (Sheffield et al., 1989; Myers et al., 1985). Microplate-array diagonal gel electrophoresis (MADGE) has been adapted to a (thermal) denaturing format and the detection of nucleotide polymorphisms was demonstrated with GC-clamped homo- and heteroduplex target DNAs (Day et al., 1998).

In conformation sensitive gel electrophoresis (CSGE), mildly denaturing conditions induce conformational changes in dsDNA which are different for homo- and heteroduplex target DNA. Hence, homo- and heteroduplex DNAs display a differential mobility during electrophoresis. CSGE can be adapted to allow fluorescence-based detection (Ganguly et al., 1998; Korkko et al., 1998; Ganguly et al., 1998).

Double-strand conformation analysis (DSCA) is a conformation-based mutation detection system wherein a known double-stranded reference DNA, labeled with fluorescein at a single strand (fluorescein-labeled reference or FLR DNA), is hybridized to unknown sample DNA. The difference in electrophoretic mobilities of the fluorescent homo- and heteroduplexes allows identification of nucleotide polymorphisms (Arguello et al., 1998). A similar technique is called HMA (heteroduplex mobility assay) but detection of DNA-duplexes relies on in gel staining of the DNA (Delwart et al., 1993). In HTA (heteroduplex tracking assay), a radiolabeled probe is annealed to a PCR product and the probe-PCR product heteroduplexes are separated by gel electrophoresis. A multiple-site-specific HTA has been described. (Resch et al., 2001; Delwart et al., 1994; Delwart et al., 1994).

Separation of homo- and heteroduplex target DNA molecules by denaturing electrophoresis is described supra. Said separation can also be performed by denaturing liquid chromatography wherein temperature determines sensitivity. Denaturing high-performance liquid chromatography (DHPLC) can moreover be performed in monolithic capillary columns enabling the setting up of an array system. Fluorescence-based detection is possible, as well as on-line coupling to a mass spectrometer. The efficiency of nucleotide polymorphism detection by DHPLC can be increased by adding a GC-clamp to the end of the target DNA fragment (Huber et al., 2001; Narayanaswami et al., 2001; Xiao et al., 2001; Huber et al., 2001).

MALDI-TOF MS (matrix-assisted laser desorption-ionization time-of-flight mass spectrometry) has been successfully used both as a direct DNA sequencing tool for DNA fragments under 100 bp and as a tool for detection of single nucleotide polymorphisms. Hybridization of allele-specific PNA-oligomers (peptide nucleic acid) with single stranded target DNA was proven to be highly compatible with MALDI-TOF MS analysis ((Griffin et al., 2000), and references therein).

With "enzymatic approaches for the generation of products signaling nucleotide sequence polymorphisms" is meant in the present context approaches relying on the activity of one or more enzymes for generation of said signaling products. Enzymes include DNA restriction endonucleases, DNA polymerases, DNA ligases, DNA/RNA structure-specific endonucleases, DNA/RNA flap endonucleases, DNA exonucleases and reverse transcriptases (RTs). Enzymatic approaches usually require a physical process (e.g. as described supra) for detection of the enzymatically produced signal.

Said enzymatic approaches include RFLP, AFLP, ASO-PCR, real-time PCR, LCR or LDR, CFLP, Invader assay, ddF, Bi-ddF, dnF, BESS and DNA minisequencing or sequencing. Some of these enzymatic approaches can be substituted for chemical or physical methodologies as will be discussed.

Restriction fragment length polymorphism (RFLP) is an assay producing a fingerprint of target DNA molecules by using one or more DNA restriction endonucleases. For detection of mutations or simple or single nucleotide polymorphisms, the target DNA is normally amplified via PCR (Schumm et al., 1988). In amplified fragment length polymorphism (AFLP), target DNA molecules are digested with a restriction endonuclease and the obtained fragments are amplified by PCR after ligation of adaptor sequences to said fragments (Vos et al., 1995). More specific enzymatic approaches to detect nucleotide sequence polymorphisms include PCR using allele-specific oligonucleotide (ASO) primers (ASO-PCR) in which the ASOs can discriminate between templates by virtue of their 3' terminal nucleotide.

ASO-PCR can be improved by incorporating an additional deliberate mismatch adjacent to the 3' discriminating base which significantly reduces amplification of the template not comprising the discriminating 3' base of the ASO primer (Cha et al., 1992; Wu et al., 1989).

In real-time PCR, the progress of the PCR reaction can be followed in real-time and detection of mutants or nucleotide sequence polymorphisms is possible via monitoring annealing or melting curves of hybrizing or hybridized, respectively, DNA molecules. A number of real-time PCR setups is known comprising three types. In a first type real-time PCR, the amount of PCR product is determined by measuring fluorescence of a dsDNA staining dye such as SYBR Green I. If performed with ASO primers, this real-type PCR type could be utilized for detection of mutants or nucleotide sequence polymorphisms. The two other types of real-time PCR are based on the principle of fluorescence resonance energy transfer (FRET) between a light emitting label or donor or fluorophore and a label catching the light emitted by the donor, said light catching label known as acceptor or quencher or receptor. The acceptor can be fluorescent or non-fluorescent. If the acceptor also is fluorescent, the transferred energy can be emitted as a fluorescence characterisic of the acceptor. If the acceptor is not fluorescent, i.e. a quencher, then the energy is lost through equilibration with solvent. The acceptor-donor pair can be incorporated in two different oligonucleotides hybridizing adjacent (within 5 basepairs) to each other (hybridization probes) or in a single dual-labeled probe (exonuclease or 'TaqMan' probe and hairpin or 'Molecular Beacons' probe).

Two formats of hybridization probes furthermore exist. In the primer/probe format, the primer is labeled internally, usually with an acceptor dye, and the probe complementary to the primer extension product is 3'-end labeled, usually with a donor fluorophore. If the primer has the ASO-format or if the probe can discriminate between variants, than this real-time PCR-type can be used in detection of mutants or nucleotide sequence polymorphisms. In the probe/probe format, the donor and acceptor dyes are conjugated to the 5' and 3' ends of two different oligonucleotides. The 5' labeled probe is furthermore blocked at its 3' end to avoid extension by the polymerase. Either probe capable of discriminating between variants allows the use of the real-time PCR-type in detection of mutants or nucleotide sequence polymorphisms. A variation to the primer/probe or probe/probe format includes the use of two oligonucleotides (probe or primer), each having a different 'universal' tail. Said universal tails can hybridize to complementary universal probes, one labeled with an acceptor dye, the other one labeled with a donor dye. Both universal probes are brought in each other's proximity via the two universally-tailed oligonucleotides (probe or primer) hybridizing simultaneously to a common target and to said universal probes. Using this method with in conjunction with allele-specific primers (amplification format) or allele-specific probes (hybridization format) enables detection of nucleotide sequence polymorphisms (Beaudet et al., 2001).

Exonuclease or 'TaqMan' robes carry a fluorophore donor and a quencher acceptor, should hybridize in between the forward and reverse PCR primers, should be 100% hybridizing during the PCR primer extension step and should have a blocked 3'end (if not by the donor or the acceptor). During the PCR extension step, the Taq polymerase encountering the hybridized TaqMan probe will destroy said probe due to the polymerase's intrinsic 5'-3' exonuclease activity. Such, the fluorophore is separated from the quencher and increased fluorescence is the result. If said exonuclease probe can discriminate between variants, than it can be applied in real-time PCR-based detection of mutants or nucleotide sequence polymorphisms. The differences between exonuclease and hairpin probes include (i) the extension of the specifically hybridizing probe with complementary 5' and 3' tails (comprising 5 nucleotides or more) capable of forming a hairpin and (ii) the donor and quencher labels are attached to the 5' and 3' ends of the hairpin tails. Hybridization of the hairpin probe to the template results in spatial separation of the donor and quencher labels and, thus, in fluorescence. If hairpin probes can discriminate between variants, than they can be applied in real-time PCR-based detection of mutants or nucleotide sequence polymorphisms. Multiplex real-time PCR in either format, except for the format in which a dsDNA-staining dye is used, is possible using different donor-acceptor pairs and/or using primers or probes with different melting temperatures. (Bernard et al., 2001; Wittwer, 2001; Tyagi et al., 1998; Tyagi et al., 1996).

A hairpin primer comprising a Molecular Beacon-type structure, its loop, however, not binding to the target DNA and further comprising a 3' single stranded extension capable of hybridizing to the target DNA can be used for direct detection of the PCR amplified target DNA. Said amplification can be followed by measuring the increasing fluorescence as the hairpin is present in the amplicon in an open conformation. This hairpin primer-type is known as Sunrise™ primers. Such hairpin primers can also be designed in the allele-specific format and can as well be used to prime rolling circle amplification of circularized padlock primers in conjunction with a second primer capable of priming complementary strand DNA synthesis (Faruqi et al., 2001; Nazarenko et al., 1997; Nazarenko et al., 1997). Rolling circle amplification is explained in more detail infra. Another variation on the same theme is the one wherein the initial PCR cycle is primed with allele-specific primers comprising a 'universal' 5'-tail capable of hybridizing with a 'universal' tailed Sunrise-type probe. These 'universal', tailed hairpin primers are known as Amplifluor™ primers. Starting from the third cycle these Amplifluor primers act in priming DNA synthesis and starting from the fourth cycle synthesis of the strand complementary to the Amplifluor primer-primed ssDNA results in opening of the hairpin and, thus, the appearance of fluorescence (Myakishev et al., 2001).

A further modification of the hairpin primers described supra comprises the incorporation in the loop of the hairpin a sequence capable of hybridizing to part of the newly amplified target DNA. Amplification of the hairpin of the primer during PCR is prevented by incorporation of a blocking nonamplifiable monomer at the 3' end of the hairpin/5' end of the primer part. Said monomer is e.g. hexethylene glycol (HEG). Fluorescence is emerging after opening of the hairpin due to hybridization of the hairpin loop with the amplified target DNA. This type of hairpin primers is known as scorpion primers (Whitcombe et al., 1999).

Methods involving real-time measurement of the synthesis of a PCR product can also be modified such that said PCR product is measured only once, e.g., after the last PCR cycle. The latter method thus involves 'end-point' measurement of the PCR product.

Ligase chain reaction (LCR) or ligase detection reaction (LDR) uses a thermostable DNA ligase enzyme to ligate two pairs of complementary probes. Only in case of both the 3' end of the upstream probe and the 5' end of the downstream probe (which must be phosphorylated) matching perfectly with the target DNA, will the DNA ligase be capable of ligating said upstream and downstream probes. Thermal cycling of this process allows exponential amplification of the probe adducts. At least the *Thermus thermophilus* (*Tth*) DNA ligase discriminates mismatches at the 3'-side of the nick with greater efficiency than mismatches at the 5'-side of the nick. The fidelity of the *Tth* DNA ligase can be increased by incorporating an additional deliberate mismatch or a universal nucleoside (e.g. 3-nitropyrrole deoxyribonucleotide) at the position 2 bases upstream of the discriminating base. Mutant *Tth* DNA ligase with further increased fidelity (e.g. K294R and K294P variants) have been described. As a template for LCR or LDR, a PCR-amplified DNA target can be used. Multiplexing of LCR/LDR is possible using differently (fluorescently) labeled allele-specific probes and/or allele-specific probes of slightly different lengths. (Khanna et al., 1999; Luo et al., 1996; Barany, 1991).

Variations of LCR have been described by Backman et al. (1991; EP0439182), said variations including the use of at least one modified probe. Variations include GAP-LCR wherein the gap between the upstream and downstream probes is filled by extension of the upstream probe by a DNA polymerase in the absence of the dNTP complementary to the 5'-end-base of the downstream probe. GAP-LCR can involve single or double gaps in 1 or 2 of the probe pairs, respectively. Gaps can also be filled by using additional gap-filling probes.

Another probe modification involves introduction of overhanging modified ends (3' end of the upstream probe or 5' end of the downstream probe) such as a ribonucleotide tail which can be removed by a ribonuclease, or such as an abasic site which can be removed by specialized DNA endonucleases. LCR/LDR probes can also be adopted to the FRET format. As such, PCR and LCR are combined in a two-step thermal cycling sequence and allele-specific dye-labeled oligonucleotide ligation (DOL) is monitored in real time through FRET (Chen et al., 1998).

Rolling circle amplification (RCA) involves a circularizable probe or padlock probe or open circle probe or C-probe (of at least 26 nucleotides) which incorporates at either end primers which, after annealing to a target DNA, can be ligated. Said padlock probe can be modified to a 'GAP-padlock probe' similarly as described for GAP-LCR. Using the 3'-terminal nucleotide as discriminating base, allele-specific circularization of the padlock probe is achieved. Circularized padlock probes are subsequently amplified using a (first) primer driving rolling circle amplification under isothermal or thermally cycling conditions. If a second primer complementary to e.g. the primer initiating RCA is added, then a mixture of hyperbranched DNA and released DNA fragments will be the result. A restriction enzyme site can be incorporated in the backbone loop of the padlock probe to convert the amplicon into monomers which can be detected after e.g. gel electrophoresis. Alternatively, the tandem DNA sequences can be decorated with specific labeled oligonucleotide tags. (Baner et al., 1998; Lizardi et al., 1998; Zhang et al., 1998; Nilsson et al., 1994; Zhang et al., 1998; Baner et al., 1998).

A number of nucleotide sequence polymorphism detection assays are available which are based on the activity of a structure-specific endonucleases.

The first endonuclease-based nucleotide sequence polymorphism detection assay is CFLP or Cleavase Fragment Length Polymorphism. CFLP uses an engineered thermostable structure-specific endonuclease called Cleavase I (Third Wave Technologies Inc., Madison, Wis., USA). The formation of secondary structures recognized by Cleavase I are introduced in a DNA molecule, e.g. an amplicon obtained via PCR, by brief thermal denaturation followed by rapid cooling. It is clear that minor differences in sequence composition, e.g. single or simple nucleotide polymorphisms, between furthermore identical DNA molecules will give rise to different secondary structures. The Cleavase I fragments produced from said variant DNA molecules will thus constitute a different and species-specific DNA fingerprint. CFLP-fingerprinting has been used to perform e.g. genotyping of hepatitis C viruses (HCVs) present in biological samples (Sreevatsan et al., 1998). CFLP was also reported to be more robust and reproducible than e.g. SSCP or DDGE (De Francesco, 1998; Brow et al., 1996; Brow et al., 1996). A similar assay using the bacteriophage resolvase T4 endonuclease VII is known as EMD (enzymatic mutation detection; (Del Tito B J et al., 1998)). Both CFLP and EMD can be used with fluoresently labeled target DNA molecules. Fragments obtained through CFLP or EMD are subsequently resolved by gel or capillary electrophoresis. Other enzymes used in DNA heteroduplex cleavage assays include MutS, MutY and thymine glycosylase (Taylor, 1999). A similar type of assay exists for resolving RNA/DNA and RNA/RNA heteroduplexes. In case of RNA/RNA duplexes, the technique is called NIRCA (non-isotropic RNase cleavage assay) which includes synthesis of RNA from a DNA-dependent RNA polymerase promoter included in a primer previously used to amplify the target DNA by PCR. (Goldrick et al., 1996; Grange et al., 1990; Myers et al., 1985). Improvements to NIRCA have been disclosed by Faudoa et al. (Faudoa et al., 2000). An alternative chemical approach has been described as CCM (chemical cleavage of mismatch). Mismatched thymines and cytosines are chemically modified followed by piperidine-mediated cleavage of the dsDNA. CCM has been modified to be compatible with fluorescent detection and with solid phase capture of the heteroduplexes (Taylor, 1999; Rowley et al., 1995; Rowley et al., 1995).

A second endonuclease-based nucleotide polymorphism detection assay is the Invader™ assay (Third Wave Technologies, Inc., Madison, Wis.) In the Invader™ assay, the DNA structure recognized by a thermostable flap endonuclease (FEN), is formed by an Invader probe that overlaps the signal probe by at least one base. The unpaired single-stranded flap of the signal probe is released during the FEN reaction and can be detected by various methods such as measuring fluorescence after capturing and extending the released signal probe flap with fluorescein-labeled nucleotides (ELISA-format), mass-spectrometry, denaturing gel electrophoresis, etc. The Invader™ assay was reported to detect mutant target in a mixture containing mutant/wild-type targets in a ratio of 1/1000. In order to discriminate between wild-type and variant (mutant or polymorphic; relative to wild-type) targets, Invader and signal probes are designed such that the cleavage site is the site of the variation. The Invader™ assay is independent of PCR and works equally well on DNA and RNA targets. (Lyamichev et al., 1999; Ryan et al., 1999; De Francesco, 1998).

A variation of the Invader™ assay is the Invader™ Squared FRET assay. In addition to the Invader and signal probes, a FRET (fluorescence resonance energy transfer) probe is required. The released signal probe fragment of the initial FEN reaction subsequently serves as an Invader probe invading the stem fragment of the hairpin formed intramolecularly in the FRET probe. This process induces a second FEN reaction during which the fluorophore in the FRET probe is separated from the nearby quenching dye in the FRET probe, resulting in the generation of fluorescence. Both FEN reactions occur at isothermic conditions (near the melting temperature of the probes) which enables a linear signal amplification. Alternatively, the loop of the FRET probe is omitted such that the released signal probe fragment of the initial FEN reaction is invading a partial dsDNA formed by the secondary target and a FRET probe complementary to the second target. The secondary target is optionally modified such that the last five nucleotides on the 3' end are 2'-O-methyl-RNA and such that it comprises a 3'$NH_2$ group. Optionally, an 2'-O-methyl RNA arrestor oligonucleotide which is complementary to the uncleaved primary signal probe is added to sequester the latter. Both options repress nonspecific background signal. The Invader Squared assay is applicable for detecting DNA as well as RNA targets. For detection of RNA targets, however, a modified endonuclease is required. (Eis et al., 2001; Hall et al., 2000; Ledford et al., 2000; Eis et al., 2001; Eis et al., 2001).

Another variation of the Invader™ assay is the Invader™ Squared MALDI-TOF MS assay. In this assay the released signal probe fragment is not measured via a second FEN reaction releasing the fluorophore but via a second FEN reaction releasing biotin-labeled oligonucleotides which are characterized via MALDI-TOF MS (Griffin et al., 1999).

Illustration of the use of the Invader assay applied to PCR amplicons was given by Mein et al. (Mein et al., 2000).

MIDAS (mutation identification DNA analysis system) is based on the annealing of a labeled probe to a target DNA. If a mismatch occurs (usually near the middle of said probe), the resulting heteroduplex can be cleaved at the mismatch site by a thermostable mismatch repair enzyme. The resulting probe fragments are thermodynamically less stable than the full-length probe and dissociate from the target DNA. A variety of probe fragment detection methods can be used. 'TaqMan'-type probes could be used in this system as well. (Bazar et al., 1999).

For analyzing nucleotide sequence polymorphism in RNA target molecules, both ribozymes (hammerhead-, hairpin-, group I intron-, ribonuclease P- or hepatitis delta viral-type ribozymes) or deoxyribozymes ('DNAzymes') can be used. This feature is moreover the basis for the possible use of these enzymes as therapeutics or in gene therapy (Cairns et al., 2000; James et al., 1995).

Dideoxy fingerprinting (ddF) is a hybrid between Sanger dideoxy sequencing and SSCP. The Sanger reaction is performed with one labeled ddNTP and one primer, resulting in a set of nested 5' co-terminal DNA fragments. Said fragments are denatured and analyzed on a non-denaturing gel (i.e. SSCP). Disappearance of a band or appearance of a new band (both relative to the fingerprint of a reference target DNA) is indicative of the responsible underlying mutation. In bidirectional ddF (Bi-ddF), a sense and an antisense primer are used in the Sanger reaction. Bi-ddF can screen larger regions of target DNA for mutations. For DNA targets comprising GC-rich regions, ddF or Bi-ddF can be enhanced by combination with denaturing gel electrophoresis. The latter technique is called denaturing ddF or dnF. (Liu et al., 1998; Liu et al., 1996; Langemeier et al., 1994; Sarkar et al., 1992).

DNA minisequencing is a method based on the annealing of an unlabeled primer to a target DNA molecule and extension of the primer with a single labeled ddNTP. DNA minisequencing can be used for efficient screening of nucleotide sequence polymorphisms if the 3'-end of the primer is located immediately upstream of the polymorphic target nucleotide. The nature of the incorporated ddNTPs can be detected by electrophoresis, by MALDI-TOF, or in an array format in which either the target DNA(s) or the unlabeled primer(s) are immobilized to a solid support. Multiplexing of DNA minisequencing is possible. (Bray et al., 2001; Pastinen et al., 1997; Pastinen et al., 1996). Minisequencing can be combined with electronic detection via an electrode or piezoelectric crystal (Patolsky et al., 2001). Minisequencing can also be adopted to comply with the FRET format. The primer to be extended is labeled with e.g. a donor dye and the incorporated nucleotide is labeled with e.g. an acceptor dye. Fluorescence intensities of the dyes are subsequently determined (Chen et al., 1997). Another variation of minisequencing is GBA (Genetic Bit Analysis). First, a target DNA is amplified by PCR using a regular primer and a phosphorothioate-modified primer or otherwise modified primer resistant to a 5'-3' dsDNA-specific exonuclease. The dsDNA amplicon is subsequently converted into ssDNA by a 5'-3'dsDNA-specific exonuclease. The resulting ssDNA is then captured by an immobilized oligonucleotide of which the 3'-terminal nucleotide is adjacent to the polymorphic site and which is extended with a single nucleotide (Nikiforov et al., 1994). Minisequencing is also possible with RNA as template and using a reverse transcriptase enzyme (Pastinen et al., 2000).

Base excision sequence scanning (BESS) is a technique involving incorporation of dUTP in an amplified target DNA molecule. Said target molecule is subsequently digested in the BESS-T™-Scan reaction (Epicentre Technologies, Madison, Wis., USA) with an enzyme mix comprising uracil-N-glycosylase (UNG) and *E. coli* endonuclease IV. The action of both enzymes result in a cleavage of the DNA at the site of dUTP incorporation. In the BESS-G-Tracker™ reaction (Epicentre Technologies, Madison, Wis., USA), deoxyguanosines are modified followed by enzymatic excision of the modified deoxyguanosines and cleavage of the DNA. Separation by gel electrophoresis of both reaction products results in T and G ladders analogous to those obtained via dideoxysequencing (see infra). Comparison with a reference DNA analyzed the same way allows identification of nucleotide sequences polymorphisms (Hawkins et al., 1999).

Still regarded as the 'gold standard' for determination of nucleotide sequence polymorphisms is direct DNA sequencing. One method of DNA sequencing is the method designed by Maxam and Gilbert (Maxam et al., 1977). The most common and widespread DNA sequencing method is based on the Sanger reaction or dideoxynucleotide chain termination reaction (Sanger et al., 1977). Sequencing primers can be labeled for detection of the terminated chains or internal labeling of the extension product is possible. Another DNA sequencing method is pyrosequencing. Here, the release of pyrophosphate (PPi) due to phosphodiester formation between two nucleotide-triphosphates. Released PPi is measured either via a secondary assay or via labeled phosphate (gamma-Pi or beta-Pi) in PPi wherein each of the four dNTPs carries a different label (see e.g. Williams 2000— WO00/36152; (Ronaghi et al., 1998)).

Cycle sequencing is based on the Sanger reaction but a thermostable polymerase is utilized. Contrary to PCR, a single primer is used in cycle sequencing. Due to the linear amplification of the target DNA, far less template DNA is required for cycle sequencing as compared to classical dideoxysequencing. Furthermore, the need to prepare single-stranded sequencing template is eliminated. ddNTPs can each be labeled with a different fluorescent tag ('dye terminators') allowing analysis of four reactions/dyes in a single gel lane. Alternatively, the label can be incorporated in the primer ('dye primers'). PCR (or RT-PCR) and sequencing can also be coupled in a single reaction, known as CAS (coupled amplification and sequencing), or a modification thereof known as CLIP™ which is run on the Visible Genetics Clipper sequencer which uses MicroCel™ polyacrylamide gel cassettes. CLIP™ Sequencing enables single-tube, simultaneous determination of the nucleotide sequence from both directions of a PCR amplicon using two sequencing primers labeled with a different dye (Cy5 and Cy5.5). (Yager et al., 1999; Ruano et al., 1991).

In the near future, nanopore sequencing might also become available (Meller et al., 2000).

Other DNA sequencing methods include molecular resonance sequencing which uses electrospray ionization (ESI) combined with Fourier transform ion cyclotron resonance (FTICR) mass spectrometry (Smith et al., 1994) and, for smaller DNA fragments, MALDI-TOF MS (cfr. supra). Diagnostic sequencing by combining specific cleavage of DNA followed by mass spectrometric analysis of the fragments has also been described (see e.g. Stanssens and Zabeau 2000—WO00/66771).

Another method of determining nucleotide sequence variations comprises dideoxynucleotide sequencing (Sanger reaction) wherein the regular dNTPs are replaced by modified dNTPs (such as alpha-thio dNTPs) that limit 3' exonuclease sensitivity of the extension product to the 3'-terminal dideoxynucleotide. The dideoxy-terminated ssDNAs are subsequently purified (e.g. via capturing them via a biotinylated sequencing primer) and hybridized to a known reference DNA. A proofreading polymerase, the unlabeled ddNTP of the primary sequencing reaction and the other three (differently) labeled ddNTPs are then added. In case of a 3' mismatch, the polymerase will exchange the unlabeled ddNTP for the correct matching labeled ddNTP. Alternatively, the secondary reaction comprises the proofreading polymerase and the same ddNTP as used in the primary reaction but modified such that it is resistant to 3' exonuclease activity. In perfectly matching primary extension products (relative to the reference DNA), the 3'-terminal ddNTP is replaced by the modified ddNTP whereas in 3' mismatching primary extension products, the 3'-terminal ddNTP is removed but not replaced by the modified ddNTP. The modified ddNTP is subsequently removed and the hybrids are further extended in the presence of regular dNTPs. The latter process is only occurring in case of an original 3' mismatch. Another variant of this method includes addition of regular dNTPs and a proofreading polymerase to the secondary reaction. Primary sequencing products with a mismatch (relative to the reference DNA) immediately 5' adjacent to the ddNTP will not be extended (the 3'-terminal ddNTP will be removed but the modified dNTP 5' adjacent to said ddNTP is resistant to 3' exonuclease activity). In yet another alternative, a Sanger-type reaction is performed in which a modified dNTP resistant to 3' exonuclease activity is used instead of a ddNTP. The resulting products are digested with a 3' exonuclease, the single strands purified and hybridized to a known reference DNA. Polymerase-mediated extension of said single strands will only occur if the modified dNTP is matching with the reference DNA. In all of the four variants mentioned, the banding pattern after separation of the final reaction products is indicative for the position and the nature of a nucleotide sequence polymorphism (Dahlhauser 2000—U.S. Pat. No. 6,150,105).

Yet another DNA sequencing methodology is known as SBH or sequencing-by-hybridization which uses an array of all possible n-nucleotide oligomers (n-mers) to identify n-mers comprised in an unknown DNA sample (Drmanac et al., 1993). Such high-density oligonucleotide arrays are useful for detecting DNA sequence polymorphisms as well, the array eventually becoming a VDA (variant detector array) (Sapoisky et al., 1999; Hacia et al., 1996). Microscope slides can be replaced by optical fibers as solid support for the oligonucleotides (Healey et al., 1997). A variation of the above-described SBH is based on solution hybridization of probes with a known information region or information tags with the target DNA fragments to be sequenced. The information tag can be a DNA bar code (eventually comprising modified bases), a molecular bar code or a nanoparticle bar code and forms the basis for identification and characterization of the hybridized target DNA (Drmanac 2000—WO/0056937).

Said high-density oligonucleotide arrays or DNA chips abolish the need to design a set of oligonucleotides specifically hybridizing under the same conditions to a set of polymorphic nucleotide sequences. The latter approach is applied in conventional reverse blot assays by carefully adjusting length, polarity and position of the mismatched nucleotide(s) in the oligonucleotide probe (Saiki et al., 1989). Conventional reverse blot hybridization assays for genotyping and detection of nucleotide sequence polymorphisms have, however, been successfully commercialized, e.g. in the LiPA (Line Probe Assay) format (Innogenetics, Ghent, Belgium). (Stuyver et al., 1997; Stuyver et al., 1996).

Alternatively, Acrydite™-modified oligonucleotide probes are copolymerized into a polyacrylamide gel. Single-stranded target DNA targets are electrophoresed through said gel and, depending on electrophoresis conditions (temperature and/or denaturant), captured by the oligonucleotides immobilized in a capture gel layer. This method is also applicable for detecting nucleotide sequence polymorphisms (Kenney et al., 1998).

Other hybridization-based methods for detecting nucleotide sequence polymorphisms include the solution phase sandwich hybridization assay in which the target DNA is captured by a target-specific immobilized capture probe and detected via an amplifier or linker probe. Two methods of signal generation have been described. A first one utilizes a branched oligonucleotide hybridizing to the flap of the linker probe not binding to the target DNA. Subsequently a labeled probe is hybridized to the branches of the amplifier probe and the amount of bound label is quantified. In a second method, a (partially) double stranded amplifier probe is hybridized to the flap of the linker probe not binding to the target DNA. The double stranded (part of) said amplifier probe comprises a promoter recognized by a DNA-dependent RNA polymerase. The signal generated is formed by newly transcribed RNA from the amplifier probe, the amount of which is quantified. (see e.g. Urdea 1991—WO91/10746).

Nucleotide sequence polymorphisms can also be detected by DASH (dynamic allele-specific hybridization) analysis which is based on melting curve analysis and measurement of fluorescence while heating. This can be done on PCR products that are e.g. biotin-labeled and captured in microplate wells. Melting curves are established by measuring fluorescence of a ds-DNA-specific intercalating dye (Prince et al., 2001; Howell et al., 1999; Prince et al., 2001). Hybridization of a fluorescently labeled probe to a target DNA can also be measured by means of fluorescence polarization spectroscopy (Murakami et al., 1991).

"FRET" or "fluorescence resonance energy transfer" involves two dyes, a donor and acceptor dye, which are usually different. In such cases, FRET is detected by either fluorescence of the acceptor dye ('sensitized fluorescence') if said acceptor is itself fluorescent, or by quenching of the donor dye fluorescence if said acceptor is a quenching non-fluorescent dye. FRET can be delayed if the donor dye releases its fluorescence over time. This process is termed "TR-FRET" or "time-resolved FRET". Donor and acceptor dyes can also be the same in which case FRET is detected by the resulting fluorescence depolarization (Runnels et al., 1995). Dyes can also be covalently coupled to form a tandem fluorescent dye or tandem dye or tandem conjugate. E.g., a single donor dye is then capable of exciting two acceptor dyes simultaneously, leading to the emission of light of multiple wavelengths. For FRET to work, the donor emission wavelength profile should at least partially overlap with the acceptor absorption wavelength profile.

Commonly used fluorescent dyes include BODIPY FL, Cy3®, Cy3.5®, Cy5®, Cy5.5®, EDANS, FAM, fluorescein, HEX, IAEDANS, JOE, Oregon Green®, (LC)Red640, (LC) Red705, ROX, TAMRA, TET, tetramethylrhodamine and Texas Red®.

Commonly used quencher dyes include BHQ-1™, BHQ-2™, BHQ-3™, DABCYL, metal clusters such as gold nanoparticles (Dubertret et al., 2001) and QSY7™.

Commonly used donor/acceptor pairs include fluorescein/tetramethylrhodamine, fluorescein/fluorescein, fluorescein/QSY7, fluorescein/LC RED640, fluorescein/LC Red705 IAEDANS/fluorescein, EDANS/DABCYL, BODIPY FL/BODIPY FL, FAM/BHQ-1, TET/BHQ-1, JOE/BHQ-1, HEX/BHQ-1, Oregon Green/BHQ-1, TAMRA/BHQ-2, ROX/BHQ-2, Cy3/BHQ-2, Cy3.5/BHQ-2, Texas Red/BHQ-2, Texas Red/BHQ-2, Cy5/BHQ-3 and Cy5.5/BHQ-3.

It will be clear to the skilled artisan that many variations and combinations can be made to the nucleotide sequence and nucleotide sequence polymorphism detection methods described supra. These are hereby incorporated in the present invention.

Based on the above explanation on methods for detecting nucleotide sequences and polymorphisms therein, the following further embodiments are included in the present invention.

The oligonucleotides according to the invention as described supra can be adapted such that they can be used in any of the methods as described above for detection of the HCV nucleotide sequences, or at least one polymorphism or genotype-specific nucleotide therein, according to the invention.

Thus, in an additional embodiment of the present invention, the oligonucleotide according to the invention further comprises a terminal extension and/or a hairpin structure, wherein said extension and/or hairpin structure is incorporated at either end or at both ends of said oligonucleotide. Said terminal extension is useful for, e.g., specifically hybridizing with another nucleic acid molecule (e.g. functioning as capture probe), and/or for facilitating attachment of said oligonucleotide to a solid support, and/or for modification of said tailed oligonucleotide by an enzyme, ribozyme or DNAzyme.

In a further embodiment of the current invention, the oligonucleotide according to the invention is comprised within a padlock probe as described above or within a hairpin structure.

In another embodiment, the oligonucleotide of the present invention has a modification allowing detection and/or capturing of said oligonucleotide. Detection and/or capturing of said oligonucleotide furthermore enables detection and/or capturing of the target nucleic acid hybridized therewith. The interaction between said oligonucleotide and said target nucleic acid may be stabilized by cross-linking both via introduction of a cross-linking modification in said oligonucleotide and/or said target nucleic acid.

In yet another embodiment, the oligonucleotide of the invention comprises a 3'-terminal mismatching nucleotide and, optionally, a 3'-proximal mismatching nucleotide. Said oligonucleotides are particularly useful for performing polymorphism-specific PCR and LCR (or GAP-LCR).

Further comprised in the present invention is a composition comprising at least one oligonucleotide according to the description given above.

It will be clear to the skilled artisan that any of the methods described above for detecting nucleotide sequences and polymorphisms therein, such as HCV genotype-specific nucleotides, can be utilized for methods for detecting the presence of a HCV virus in a biological sample; and/or for determining the genotype, i.e. genotyping, of a HCV virus present in a biological sample.

One aspect of the invention relates to a method for detecting the presence of a HCV virus in a biological sample and/or a method for determining the genotype of a HCV virus present in a biological sample, said methods comprising the step of detecting the presence of a HCV polynucleic acid or fragment thereof according to the invention.

Said methods are based on, e.g., an amplification reaction, a hybridization reaction, a reverse hybridization reaction or a sequencing reaction. In any of these reaction, an oligonucleotide according to the invention can be utilized. Said methods may further include the use of an oligonucleotide according to the invention for detection of a HCV polynucleic acid or fragment thereof of the invention and/or for determining the genotype of the HCV virus present in a biological sample and from which said HCV polynucleic acid or fragment was obtained.

A specific embodiment thereto includes said methods comprising the steps of:
(i) obtaining a target HCV polynucleic acid from a biological sample suspected to contain a HCV polynucleic acid or fragment thereof according to the invention;
(ii) obtaining the nucleic acid sequence of the target HCV polynucleic acid of (i);
(iii) infering, from the nucleic acid sequence obtained in (ii), the presence of a HCV polynucleic acid or fragment thereof according to the invention and, therefrom, the presence of a HCV in said biological sample and/or the genotype of said HCV virus present in said biological sample.

Another specific embodiment thereto includes said methods comprising:
(i) obtaining a target HCV polynucleic acid present in a biological sample and/or obtaining the nucleotide sequence thereof, wherein the biological sample is suspected to contain a HCV virus of the genotype of the invention;
(ii) when appropriate, partial or complete denaturation, or enzymatic modification, of the polynucleic acids obtained in step (i);
(iii) when appropriate, renaturation of the denatured polynucleic acids obtained in step (ii), preferably in the presence of at least one oligonucleotide according to the invention, and, if needed, including the step of enzymatically modifying, including extending, said oligonucleotide;
(iv) when appropriate, detection of a discriminatory signal obtained from analysis of the partially or completely denatured polynucleic acids obtained in step (ii), and/or of the hybrids formed in step (iii), and/or of the enzymatic modifications obtained in step (ii) and/or (iii);

(v) infering, from the discriminatory signal detected in step (iv), and/or from the nucleotide sequence obtained in (i), the presence of said HCV virus in said biological sample and/or the genotype of said HCV virus present in said biological sample.

In yet another specific embodiment thereto, said methods are comprising:
(i) obtaining a target HCV polynucleic acid from a biological sample suspected to contain a HCV polynucleic acid or fragment thereof according to the invention;
(ii) contacting the target HCV polynucleic acid of (i) with an oligonucleotide capable of discriminating at least one genotype-specific nucleotide present in said target HCV polynucleic acid, and said contacting generating a discriminatory signal;
(iii) infering, from the discriminatory signal obtained in (ii), the presence of a HCV polynucleic acid or fragment thereof according to the invention and, therefrom, the presence of a HCV virus in said biological sample and/or the genotype of said HCV present in said biological sample.

In the latter methods, said discriminating in (ii) can be based on hybridization and said discriminatory signal in (iii) then is a hybridization signal.

With "at least one genotype-specific nucleotide/amino acid" is meant a single nucleotide/amino acid or a set of nucleotides/amino acids specific to a nucleic acid/amino acid sequence of the new HCV type according to the invention. The specific nucleotides/amino acids of said set can form a contiguous sequence in or can be dispersed in a limited region of a nucleic acid/amino acid sequence of the new HCV type according to the invention. Generally, said limited region comprising the specific nucleotides/amino acids of said set is limited to the size of an oligonucleotide/oligopeptide as defined herein.

"Specific to a nucleic acid/amino acid sequence of the new HCV type according to the invention" is to be interpreted as "unique to", i.e., not occurring in any other of the known HCV types. The term is referring to individual nucleotides/amino acids as well as to a set of nucleotides/amino acids as outlined above. A region comprising said individual nucleotide/amino acid or a set of such nucleotides/amino acids is to be considered as a region specific to, or unique to, the new HCV type according to the invention.

With an "oligonucleotide capable of discriminating, in a (poly)nucleic acid at least one genotype-specific nucleotide" is meant an oligonucleotide yielding a signal when contacted with a (poly)nucleic acid comprising said at least one genotype-specific nucleotide but not yielding a signal when contacted with a (poly)nucleic acid not comprising said at least one genotype-specific nucleotide. Said signal, also referred to as "discriminatory signal", may be any signal obtainable by using said oligonucleotide in any of the assays capable of detecting nucleotide sequences and nucleotide sequence polymorphisms as described above. Said signals include, e.g., fluorescent signals, (chemi)luminescent signals, radioactive signals, light signals, hybridization signals, mass spectrometric signals, spectrometric signals, chromatographic signals, electric signals, electronic signals, electrophoretic signals, real-time PCR signals, PCR signals, LCR signals, CFLP-assay signals and Invader-assay signals.

With "contacting an oligonucleotide with a (poly)nucleic acid" is generally meant annealing of said oligonucleotide with said (poly)nucleic acid or hybridizing said oligonucleotide with said (poly)nucleic acid. "Contacting an oligonucleotide with a (poly)nucleic acid" does not exclude and can thus further comprise enzymatic modification of said oligonucleotide wherein said modification may occur at the extremities of said oligonucleotide and/or internally in the nucleotide sequence of said oligonucleotide. Examples of enzymatic modifications of oligonucleotides are given in, e.g., the assays capable of detecting nucleotide sequences and nucleotide sequence polymorphisms described herein.

In another embodiment of the invention said methods further comprise, where applicable, aligning and/or comparing the obtained nucleic acid sequence with a set of HCV nucleic acid sequences contained within a database.

With "database" is meant in the present context a collection of nucleic acid or amino acid sequences, more specifically of HCV nucleic acid or amino acid sequences. A database is to be understood to comprise at least one nucleic acid or at least one amino acid sequence. A database can be recorded on a variety of carriers. Such carriers include computer readable carriers.

Comparison of sequences, e.g. determination of percent identity between sequences, and alignment of sequences can be performed using a mathematical algorithm. Determination of percent identity between sequences relies on a previous alignment of sequences. The percentage identity (and similarity) between sequences can be determined by using e.g. the GAP program (part of GCG, Genetics Computer Group, software; now available via Accelrys on http://www.accelrys.com). Alignments between sequences can e.g. be made using the ClustalW algorithm (e.g. part of GCG software or part of VNTI software distributed by InforMax Inc.). An alignment usually is a gapped alignment, i.e. the introduction of gaps in a sequence is allowed in order to optimize the alignment. A detailed statistical theory for gapped alignments has not been developed, and the best gap costs to use with a given substitution matrix are to be determined empirically. These algorithms make use of amino acid substitution matrices to detect similarities among sequences that have diverged (Altschul, 1991). Substitution matrices have also been applied to DNA sequence comparison (States et al., 1991). It will be clear to the one skilled in the art that the efficiency of aligning similar amino acid residues also determines the percentage of identity between sequences. A commonly used substitution matrix is the BLOSUM62 matrix. For particularly long and weak alignments, the BLOSUM45 matrix may be used. For alignment of short sequences, the older PAM (percent accepted mutation)-matrices may be used (e.g. PAM30, PAM70). A good alignment of sequences with a larger evolutionary distance can be to obtained by using a PAM substitution matrix with a greater number (e.g. by using PAM100 instead of PAM40). The number after the BLOSUM matrix (e.g. BLOSUM62) refers to the minimum percent identity of the blocks used to construct the matrix; greater numbers are lesser distances. A database of sequences can be searched against using a nucleic acid or amino acid sequence of interest as 'query sequence'. Algorithms for searching databases are usually based on the BLAST software (Altschul et al., 1990) and comprise: 1) BLASTN, for searching a nucleic acid query sequence against a database of nucleic acid sequences; 2) BLASTP, for searching an amino acid query sequence against a database of amino acid sequences; 3) TBLASTN, for searching a amino acid query sequence against a database of translated nucleic acid sequences (translations in the six possible frames); 3) BLASTX, for searching a translated nucleic acid query sequence (translations in the six possible frames) against a database of amino acid sequences; and 4) TBLASTX, for searching a translated nucleic acid query sequence (translations in the six possible frames) against a database of translated nucleic acid sequences (translations in the six possible frames). For short query sequences, the expect value threshold is preferably set high, e.g. at 1000 for nucleotide sequences and at 20000 for amino acid sequences.

Another aspect of the current invention relates to a diagnostic kit for detecting the presence of a HCV virus in a biological sample and/or for determining the genotype of a HCV virus present in a biological sample, said kit comprising at least a means for detecting the presence of a HCV polynucleic acid according to the invention.

Such diagnostic kits are comprising, e.g. an oligonucleotide according to the invention. Said oligonucleotides may be attached to a solid support. Alternatively, a range of such oligonucleotides are attached or coupled to specific locations on the solid support, e.g., in the form of parallel lines. An exemplary solid support is a membrane.

A specific embodiment thereto includes said diagnostic kit comprising:
(i) a means for obtaining the nucleic acid sequence of a target HCV polynucleic acid from a biological sample suspected to contain a HCV polynucleic acid or fragment thereof according to the invention;
(ii) a means for infering, from the nucleic acid sequence obtained from the target HCV polynucleic acid, the presence of a polynucleic acid unique to a HCV polynucleic acid according to the invention, or the presence of at least one genotype-specific nucleotide therein, and, therefrom, the presence in said biological sample of a HCV and/or the genotype of said HCV.

In another specific embodiment, said diagnostic kit is comprising an oligonucleotide capable of discriminating, in said HCV polynucleic acid, at least one genotype-specific nucleotide.

In yet another embodiment, said diagnostic kit is additionally comprising a means for detecting the discriminatory signal obtained by contacting said HCV polynucleic acid and said oligonucleotide or oligonucleotides.

Furthermore embodied are said diagnostic kits wherein said oligonucleotide or oligonucleotides are attached or immobilized to a solid support.

Another specific embodiment thereto includes said diagnostic kit comprising:
(i) a means for obtaining a target HCV polynucleic acid present in said biological sample and/or obtaining the nucleotide sequence thereof;
(ii) when appropriate, at least one oligonucleotide pair suitable for amplification of a target HCV polynucleic acid according to the invention;
(iii) when appropriate, a means for denaturing nucleic acids;
(iv) when appropriate, at least one oligonucleotide according to the invention;
(v) when appropriate, an enzyme capable of modifying a double stranded or single stranded nucleic acid molecule;
(vi) when appropriate, a hybridization buffer, or components necessary for producing said buffer;
(vii) when appropriate, a wash solution, or components necessary for producing said solution;
(viii) when appropriate, a means for detecting partially or completely denatured polynucleic acids and/or a means for detecting hybrids formed in the preceding hybridization and/or a means for detecting enzymatic modifications of nucleic acids, wherein said means is producing a discriminatory signal;
(ix) when appropriate, a means for attaching an oligonucleotide to a known location on a solid support;
(x) a means for infering from the discriminatory signal detected in (viii), and/or from the nucleotide sequence obtained in (i), the presence of a polynucleic acid unique to a HCV polynucleic acid according to the invention, or the presense of at least one genotype-specific nucleotide therein, and, therefrom, the presence of said HCV virus in said biological sample and/or the genotype of said HCV virus present in said biological sample.

With "a means for infering, from a nucleic acid sequence, the presence of a genotype-specific specific nucleotide" is meant any technique or method to localize and identify in said nucleic acid sequence said genotype-specific nucleotide. Said means can include a method performed manually, or performed computationally, or performed manually and/or computationally. Said means may include aligning and/or comparing an obtained nucleic acid sequence with a set of nucleic acid sequences contained within a database. Said means may furthermore include the result of the method being presented in the form of a report wherein said report can be in paper form, in electronic form or on a computer readable carrier or medium. Said means may furthermore include the searching of (nucleic acid and/or amino acid) sequence databases and/or the creation of (nucleic acid and/or amino acid) sequence alignments, the results of which may or may not be included in said report. Said means may furthermore include a device for detecting a discriminatory signal, or a kit insert or kit chart indicating how to interpret a detected discriminatory signal, or indicating where a specific discriminatory signal should appear, e.g. on a solid carrier carrying multiple oligonucleotides which can be arranged as spots, lines, dots, etc and possibly interpreting said discriminatory signal occurring on a specific location.

A further embodiment covers any of the above methods of the invention characterized further in that said methods are based on determining the nucleic acid sequence.

A further embodiment covers any of the above methods of the invention characterized further in that said methods are based on a hybridization assay.

A further embodiment covers any of the above methods of the invention characterized further in that said methods are based on a reverse hybridization assay.

A further embodiment covers any of the above diagnostic kits of the invention characterized further in that said diagnostic kits are based on determining the nucleic acid sequence.

A further embodiment covers any of the above diagnostic kits of the invention characterized further in that said diagnostic kits are based on a hybridization assay.

A further embodiment covers any of the above diagnostic kits of the invention characterized further in that said diagnostic kits are based on a reverse hybridization assay.

A further embodiment covers any of the above diagnostic kits of the invention characterized further in that said diagnostic kits are based on a line probe assay.

The present invention also relates to a method for the detection of HCV nucleic acids present in a biological sample, comprising:
(i) optionally extracting sample nucleic acid,
(ii) amplifying the nucleic acid with at least one primer as defined herein,
(iii) detecting the amplified nucleic acids.

The present invention also relates to a method for the detection of HCV nucleic acids present in a biological sample, comprising:
(i) optionally extracting sample nucleic acid,
(ii) optionally amplifying the nucleic acid with at least one primer as defined herein, or with a universal HCV primer,
(iii) hybridizing the nucleic acids of the biological sample, optionally under denatured conditions, at appropriate conditions with one or more probes as defined herein, with said probes being preferably attached to a solid substrate,
(iv) optionally washing at appropriate conditions,
(v) detecting the hybrids formed.

The present invention in particular relates to a method for the detection of HCV nucleic acids present in a biological sample, comprising:
(i) optionally extracting sample nucleic acid,
(ii) determining the presence of a HCV type nucleic acid sequence according to the invention by means of a sequencing reaction.

The present invention also relates to a method for detecting the presence of one or more HCV genotypes present in a biological sample, comprising:
(i) optionally extracting sample nucleic acid,
(ii) specifically amplifying the nucleic acid with at least one primer as defined herein,
(iii) detecting said amplified nucleic acids.
(iv) inferring the presence of one or more HCV genotypes present from the observed pattern of amplified products.

The present invention also relates to a method for detecting the presence of one or more HCV genotypes present in a biological sample, comprising:
(i) optionally extracting sample nucleic acid,
(ii) optionally amplifying the nucleic acid with at least one primer as defined herein or with a universal HCV primer,
(iii) hybridizing the nucleic acids of the biological sample, optionally under denatured conditions, at appropriate conditions with one or more probes as defined herein, with said probes being preferably attached to a solid substrate,
(iv) optionally washing at appropriate conditions,
(v) detecting the hybrids formed,
(vi) inferring the presence of one or more HCV genotypes present from the observed hybridization pattern.

The present invention also relates to a method as defined herein, wherein said probes are further characterized as defined herein.

In any of the above methods of the invention, the biological sample is suspected or liable to contain HCV or its nucleic acids.

The present invention also relates to a method as defined herein, wherein said nucleic acids are labeled during or after amplification. Preferably, this technique could be performed in the 5' non-coding (NCR), Core, E1 and/or NS5B region.

The term "nucleic acid" can also be referred to as analyte strand and corresponds to a single- or double-stranded nucleic acid molecule. This analyte strand is preferentially positive- or negative stranded RNA, cDNA or amplified cDNA.

The term "universal HCV primer" refers to oligonucleotide sequences complementary to any of the regions conserved in the HCV genomes of most or all HCV genotypes.

The expression "appropriate hybridization and washing conditions" is to be understood as stringent and are generally known in the art (e.g. Sambrook et al., 1989). However, according to the hybridization solution (SSC, SSPE, etc.), these probes should be hybridized at their appropriate temperature in order to attain sufficient specificity. In order to allow hybridization to occur, the nucleic acid molecules are generally thermally, chemically (e.g. by NaOH) or electrochemically denatured to melt a double strand into two single strands and/or to remove hairpins or other secondary structures from single stranded nucleic acids. The stringency of hybridization is influenced by conditions such as temperature, salt concentration and hybridization buffer composition. High stringency conditions for hybridization include high temperature and/or low salt concentration (salts include NaCl and $Na_3$-citrate) and/or the inclusion of formamide in the hybridization buffer and/or lowering the concentration of compounds such as SDS (detergent) in the hybridization buffer and/or exclusion of compounds such as dextran sulfate or polyethylene glycol (promoting molecular crowding) from the hybridization buffer. Conventional hybridization conditions are described in e.g. Sambrook et al. (Sambrook et al., 1989) but the skilled craftsman will appreciate that numerous different hybridization conditions can be designed in function of the known or the expected homology and/or length of the nucleic acid sequence. Generally, for hybridizations with DNA probes without formamide, a temperature of 68° C., and for hybridization with formamide, 50% (v/v), a temperature of 42° C. is recommended. For hybridizations with oligonucleotides, the optimal conditions (formamide concentration and/or temperature) depend on the length and base composition of the probe and must be determined individually. In general, optimal hybridization for oligonucleotides of about 10 to 50 bases in length occurs approximately 5° C. below the melting temperature for a given duplex. Incubation at temperatures below the optimum may allow mismatched sequences to hybridize and can therefor result in reduced specificity. When using RNA oligonucleotides with formamide (50% v/v) it is recommend to use a hybridization temperature of 68° C. for detection of target RNA and of 50° C. for detection of target DNA. Alternatively, a high SDS hybridization solution can be utilized (Church et al., 1984). The specificity of hybridization can furthermore be ensured through the presence of a crosslinking moiety on the nucleic acid probe (e.g. Huan et al. 2000—WO00/14281). Said crosslinking moiety enables covalent linking of the nucleic acid probe with the target nucleotide sequence and hence allows stringent washing conditions. Such a crosslinking nucleic acid probe can furthermore comprise another label suitable for detection/quantification of the probe hybridized to the target.

The term "labeled" refers to the use of labeled nucleic acids. This may include the use of labeled nucleotides incorporated during the polymerase step of the amplification such as illustrated by Saiki et al. (1988) or Bej et al. (1990) or labeled primers, or by any other method known to the person skilled in the art.

The process of the invention comprises the steps of contacting any of the probes as defined herein, with one of the following elements:
either a biological sample in which the nucleic acids are made available for hybridization,
or the purified nucleic acids contained in the biological sample
or a single copy derived from the purified nucleic acids,
or an amplified copy derived from the purified nucleic acids, with said elements or with said probes being attached to a solid substrate.

The expression "inferring the presence of one or more HCV genotypes present from the observed hybridization pattern" refers to the identification of the presence of HCV genomes in the sample by analyzing the pattern of binding of a panel of oligonucleotide probes. Single probes may provide useful information concerning the presence or absence of HCV genomes in a sample. On the other hand, the variation of the HCV genomes is dispersed in nature, so rarely is any one probe able to identify uniquely a specific HCV genome. Rather, the identity of an HCV genotype may be inferred from the pattern of binding of a panel of oligonucleotide probes, which are specific for (different) segments of the different HCV genomes. Depending on the choice of these oligonucleotide probes, each known HCV genotype will correspond to a specific hybridization pattern upon use of a specific combination of probes. Each HCV genotype will also be able to be discriminated from any other HCV genotype amplified with the same primers depending on the choice of the oligonucleotide probes. Comparison of the generated pattern of positively hybridizing probes for a sample containing one or more unknown HCV sequences to a scheme of expected hybridization patterns, allows one to clearly infer the HCV genotypes present in said sample.

The present invention thus relates to a method as defined herein, wherein one or more hybridization probes are oligonucleotide fragments taken from any of SEQ ID NOs:1, 2, 4, 6, 8, 10, 12, 14, or 36–49 or sequence variants thereof as defined herein.

In order to distinguish the amplified target HCV genomes from each other, the amplified target HCV polynucleic acids are hybridized to a set of sequence-specific DNA probes targeting HCV genotype regions (unique regions) located in the HCV polynucleic acids. Most of these probes target the most type- or subtype-specific regions of HCV genotypes, but some can be caused to hybridize to more than one HCV genotype. According to the hybridization solution (SSC, SSPE, etc.), these probes should be stringently hybridized at their appropriate temperature in order to attain sufficient specificity. However, by slightly modifying the DNA probes, either by adding or deleting one or a few nucleotides at their extremities (either 3' or 5'), or substituting some non-essential nucleotides (i.e. nucleotides not essential to discriminate between types) by others (including modified nucleotides or inosine) these probes or variants thereof can be caused to hybridize specifically at the same hybridization conditions (i.e. the same temperature and the same hybridization solution). Also changing the amount (concentration) of probe used may be beneficial to obtain more specific hybridization results. It should be noted in this context, that probes of the same length, regardless of their GC content, will hybridize specifically at approximately the same temperature in TMAC1 solutions, i.e. tetraalkylammonium salt solutions (Jacobs et al., 1988). Suitable assay methods for purposes of the present invention to detect hybrids formed between the oligonucleotide probes and the nucleic acid sequences in a sample may comprise any of the assay formats known in the art, such as the conventional dot-blot format, sandwich hybridization or reverse hybridization. For example, the detection can be accomplished using a dot blot format, the unlabelled amplified sample being bound to a membrane, the membrane being incorporated with at least one labeled probe under suitable hybridization and wash conditions, and the presence of bound probe being monitored. An alternative and preferred method is a "reverse" dot-blot format, in which the amplified sequence contains a label. In this format, the unlabelled oligonucleotide probes are bound to a solid support and exposed to the labeled sample under appropriate stringent hybridization and subsequent washing conditions. It is to be understood that also any other assay method which relies on the formation of a hybrid between the nucleic acids of the sample and the oligonucleotide probes according to the present invention may be used.

According to an advantageous embodiment, the process of detecting one or more HCV genotypes contained in a biological sample comprises the steps of contacting amplified HCV nucleic acid copies derived from the biological sample, with oligonucleotide probes which have been immobilized as parallel lines on a solid support.

According to this advantageous method, the probes are immobilized in a Line Probe Assay (LiPA) format. This is a reverse hybridization format (Saiki et al., 1988) using membrane strips onto which several oligonucleotide probes (including negative or positive control oligonucleotides) can be conveniently applied as parallel lines. The LiPA is a very rapid and user-friendly hybridization test. Results can be read after 4 hours after the start of the amplification. After amplification during which usually a non-isotopic label is incorporated in the amplified product, and alkaline denaturation, the amplified product is contacted with the probes on the membrane and the hybridization is carried out for about 1 to 1,5 h hybridized polynucleic acid is detected. From the hybridization pattern generated, the HCV type can be deduced either visually, but preferably using dedicated software. The LiPA format is completely compatible with commercially available scanning devices, thus rendering automatic interpretation of the results very reliable. All those advantages make the LiPA format liable for the use of HCV detection in a routine setting. The LiPA format should be particularly advantageous for detecting the presence of different HCV genotypes.

The invention thus also relates to a solid support, preferably a membrane strip, carrying on its surface, one or more probes as defined herein, coupled to the support in the form of parallel lines.

The present invention also relates to a method for detecting and identifying novel HCV genotypes, different from the known HCV genomes, comprising the steps of:
determining to which HCV genotype the nucleotides present in a biological sample belong, according to the process as defined herein,
in the case of observing a sample which does not generate a hybridization pattern compatible with, for example, those defined in Table 3, sequencing the portion of the HCV genome sequence corresponding to the aberrantly hybridizing probe of the new HCV genotype to be determined.

The present invention particularly also relates to a polypeptide having an amino acid sequence encoded by a polynucleic acid as defined herein, or a part thereof which is unique to the new HCV type according to the present invention as defined in Table 5, and which contains at least one amino acid differing from any of the known HCV types or subtypes, or an analog thereof being substantially homologous and biologically equivalent.

Thus, in a further aspect the current invention includes an isolated HCV polypeptide of a clade 6 HCV virus of a genotype different from clade 6 genotypes 6–9 and 11, said polypeptide characterized in that it is comprising an amino acid sequence chosen from any of:
an amino acid sequence defined by any of SEQ ID NOs:3, 5, 7, 9, 11, 13, 15, 50–61, or 63;
a Core amino acid sequence at least 92% identical to any of SEQ ID NOs:53–55;
an E1 amino acid sequence at least 79% identical to SEQ ID NO:56;

a Core/E1 amino acid sequence at least 85% identical to any of SEQ ID NOs:11, 13, 15;

a Core/E1 amino acid sequence at least 91% identical to any of SEQ ID NOs:50–52;

an NS5B amino acid sequence at least 87% identical to SEQ ID NO:9;

a Core amino acid sequence encoded by a nucleic acid sequence at least 85% identical to any of SEQ ID NOs:39–41;

an E1 amino acid sequence encoded by a nucleic acid sequence at least 71% identical to SEQ ID NO:42;

a Core/E1 amino acid sequence encoded by a nucleic acid sequence at least 78% identical to any of SEQ ID NOs:10, 12, 14;

a Core/E1 amino acid sequence encoded by a nucleic acid sequence at least 84% identical to any of SEQ ID NOs:36–38;

an NS5B amino acid sequence encoded by a nucleic acid sequence at least 75% identical to SEQ ID NO:8; or a fragment of any of these amino acid sequences which is unique to said HCV genotype.

More specifically, the polypeptides or fragments thereof according to the invention include recombinant polypeptides, synthetic polypeptides or polypeptides comprising one or more modified or labeled amino acids.

The term 'polypeptide' refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring. The terms "protein", "peptide" or "oligopeptide", when used herein refer to amino acids in a polymeric form of any length. Said terms also include known amino acid modifications such as disulphide bond formation, cysteinylation, oxidation, glutathionylation, methylation, acetylation, farnesylation, biotinylation, stearoylation, formylation, lipoic acid addition, phosphorylation, sulphation, ubiquitination, myristoylation, palmitoylation, geranylgeranylation, cyclization (e.g. pyroglutamic acid formation), oxidation, deamidation, dehydration, glycosylation (e.g. pentoses, hexosamines, N-acetylhexosamies, deoxyhexoses, hexoses, sialic acid etc.) and acylation as well as non-naturally occurring amino acid residues, L-amino acid residues and D-amino acid residues. A number of said amino acid modifications can occur as a result of post-translational modification as will be recognized by the one skilled in the art. Other modifications include the addition of a chemical group to one or more amino acids of a protein, peptide or oligopeptide. Said chemical groups include e.g. biotin. Said chemical groups further include groups introduced on cysteine-thiols resulting either in a reversibly or irreveribly blocked cysteinethiol; examples of cysteine-modifying compounds include N-ethylmaleimide, biotin-N-ethylmaleimide, vinylpyridine, iodoacetic acid, iodoacetamide, ethylenimide, and methyliodide. Furthermore, cysteines can be converted into S-sulfocysteines in a sulfitolysis reaction. Proteins, peptides or oligopeptides can furthermore generally be labeled radioactively, chemiluminescently, fluorescently, phosphorescently, with infrared dyes or with a surface-enhanced Raman label or plasmon resonant particle. By "biologically equivalent" as used throughout the specification and claims, it is meant that the compositions are immunogenically equivalent to the proteins (polypeptides) or peptides of the invention as defined herein.

By "substantially homologous" as used throughout the ensuing specification and claims to describe proteins and peptides, it is meant a degree of homology in the amino acid sequence to the proteins or peptides of the invention. Preferably the degree of homology is in excess of 90%, e.g., in excess of 91%, 92%, 93%, 94%, preferably in excess of 95, e.g., in excess of 96%, 97%, 98%, with a particularly preferred group of proteins being in excess of 99% homologous with the proteins or peptides of the invention.

The term "analog" as used throughout the specification or claims to describe the proteins or peptides of the present invention, includes any protein or peptide having an amino acid residue sequence substantially identical to a sequence specifically shown herein in which one or more residues have been conservatively substituted with a biologically equivalent residue. Examples of conservative substitutions include the substitution of one-polar (hydrophobic) residue such as isoleucine, valine, leucine or methionine for another, the substitution of one polar (hydrophillic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Examples of allowable mutations according to the present invention can be found in Table 4.

The phrase "conservative substitution" also includes the use of a chemically derivatized residue in place of a non-derivatized residue provided that the resulting protein or peptide is biologically equivalent to the protein or peptide of the invention.

"Chemical derivative" refers to a protein or peptide having one or more residues chemically derivatized by reaction of a functional side group. Examples of such derivatized molecules, include but are not limited to, those molecules in which free amino groups have been derivatized to form amine hydrochlorides, p-toluene sulfonyl groups, carbobenzoxy groups, t-butyloxycarbonyl groups, chloracetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those proteins or peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and omithine may be substituted for lysine. The proteins or peptides of the present invention also include any protein or peptide having one or more additions and/or deletions or residues relative to the sequence of a peptide whose sequence is shown herein, so long as the peptide is biologically equivalent to the proteins or peptides of the invention. It is to be noted that, at the level of the amino acid sequence, at least one amino acids difference (with respect to known HCV amino acid sequences) is sufficient to be part of the invention, which means that the polypeptides of the invention correspond to polynucleic acids having at least one nucleotide difference (with known HCV polynucleic acid sequences) involving an amino acid difference in the encoded polyprotein. As the NS4 and the Core regions are known to contain several epitopes, for example characterized in patent application EP-A-0 489 968, and as the E1 protein is expected to be subject to immune attack as part of the viral envelope and expected to contain epitopes, the NS4, Core and E1 epitopes of the new types and subtypes disclosed herein will consistently differ from the epitopes present in previously known genotypes. This is exemplified by the type-specificity of NS4 synthetic peptides as described in Simmonds et al. (1993c) and Stuyver et al. (1993b) and PCT/EP 94/01323 and the type-specificity of recombinant E1 proteins as described in Maertens et al. (1994).

The peptides according to the present invention contain preferably at least 3, preferably 4, 5 contiguous HCV amino acids, 6, 7 preferably however at least 8 contiguous HCV amino acids, at least 10 or at least 15 (for instance at least 9, 10, 11, 12, 13, 14, 15, 16, 17, 19, 20, 21, 22, 23, 24, 25, 26, 27, 28, 29, 30, 31, 32, 33, 34, 35, 40, 45, 50, 55, 60, 65, 70, 75, 80, 85, 90, 95, 100 or more amino acids).

The polypeptides of the invention, and particularly the fragments, can be prepared by classical chemical synthesis. The synthesis can be carried out in homogeneous solution or in solid phase. For instance, the synthesis technique in homogeneous solution which can be used is the one described by Houbenweyl in the book entitled "Methode der organischen chemie" (Method of organic chemistry) edited by E. Wunsh, vol. 15-I et II. THIEME, Stuttgart 1974. The polypeptides of the invention can also be prepared in solid phase according to the methods described by Atherton and Shepard in their book entitled "Solid phase peptide synthesis" (IRL Press, Oxford, 1989). The polypeptides according to this invention can be prepared by means of recombinant DNA techniques as described by Sambrook et al., Molecular Cloning: A Laboratory Manual 2nd edition, New York, Cold Spring Harbor Laboratory, 1989).

Hence, the present invention relates to a polypeptide having an amino acid sequence encoded by a polynucleic acid as defined herein, or a part thereof which is unique to the new HCV type according to the invention, or an analog thereof which is unique to the new HCV type according to the invention, and which is substantially homologous and biologically equivalent.

The present invention relates particularly to a polypeptide as defined herein, comprising in its amino acid sequence at least one unique amino acid residues. With a notation being composed of a letter representing the amino acid residue by its one-letter code, and a number representing the amino acid numbering according to Kato et al., 1990 as shown in Table 1 (see also the numbering in FIGS. 1 and 2), or a part thereof which is unique to at least one of the HCV subtypes or types as defined in Table 5, and which contains at least one amino acid differing from any of the known HCV types or subtypes, or an analog thereof being substantially homologous and biologically equivalent to said polypeptide or part thereof.

TABLE 4

Overview of the amino acid substitutions which could form the basis of analogs (muteins) as defined herein

| Amino acids | Synonymous groups |
|---|---|
| Ser (S) | Ser, Thr, Gly, Asn |
| Arg (R) | Arg, His, Lys, Glu, Gln |

TABLE 4-continued

Overview of the amino acid substitutions which could form the basis of analogs (muteins) as defined herein

| Amino acids | Synonymous groups |
|---|---|
| Leu (L) | Leu; Ile, Met, Phe, Val, Tyr |
| Pro (P) | Pro, Ala, Thr, Gly |
| Thr (T) | Thr, Pro, Ser, Ala, Gly, His, Gln |
| Ala (A) | Ala, Pro, Gly, Thr |
| Val (V) | Val, Met, Ile, Tyr, Phe, Leu, Val |
| Gly (G) | Gly, Ala, Thr, Pro, Ser |
| Ile (I) | Ile, Met, Leu, Phe, Val, Ile, Tyr |
| Phe (F) | Phe, Met, Tyr, Ile, Leu, Trp, Val |
| Tyr (Y) | Tyr, Phe, Trp, Met, Ile, Val, Leu |
| Cys (C) | Cys, Ser, Thr, Met |
| His (H) | His, Gln, Arg, Lys, Glu, Thr |
| Gln (Q) | Gln, Glu, His, Lys, Asn, Thr, Arg |
| Asn (N) | Asn, Asp, Ser, Gln |
| Lys (K) | Lys, Arg, Glu, Gln, His |
| Asp (D) | Asp, Asn, Glu, Gln |
| Glu (E) | Glu, Gln, Asp, Lys, Asn, His, Arg |
| Met (M) | Met, Ile, Leu, Phe, Val |

These unique amino acid residues can be deduced from aligning the new HCV amino acid sequences as given in FIG. 1 to all known HCV sequences. An alignment with the new sequences as represented in SEQ ID NOs:3, 5, 7, 9, 11, 13, 15, 50–63 can be done, for instance. It should be clear that the alignments given in these figures may be completed with all known HCV sequences to illustrate that any of the above-given unique residues is indeed unique for at least one of the new HCV sequences of the present invention. Within the group of unique and new amino acid residues of the present invention, unique residues may be found which are specific for the new HCV type, according to the HCV classification system used in the present invention. In order to obtain these residues, alignments may be performed by the man skilled in the art to deduce the type- and or subtype-specificity of any of the unique residues given herein.

The polypeptides according to this embodiment of the invention may be optionally labeled, or attached to a solid substrate, or coupled to a carrier molecule such as biotin, or mixed with a proper adjuvant all known in the art and according to the intended use (diagnostic, therapeutic or prophylactic).

The present invention also relates to a polypeptide as defined herein, comprising in its amino acid sequence at least one of the sequences represented by SEQ ID NOs:3, 5, 7, 9, 11, 13, 15, or 50–63 as listed herein, or comprising a part thereof which is unique to the new HCV type according to the invention as defined in Table 5, or an analog thereof being substantially homologous and biologically equivalent to said polypeptide or part thereof.

The present invention thus relates also to a polypeptide having an amino acid sequence as represented in any of SEQ ID NOs:3, 5, 7, 9, 11, 13, 15, or 50–63, or a part thereof which is unique to the new HCV type according to the invention, as defined in Table 5, or an analog thereof being substantially homologous and biologically equivalent to said polypeptide or part thereof.

The variable region in the core protein (V-Core) has been shown to be useful for serotyping (Machida et al., 1992). The V-Core sequence of the new HCV type of the present invention shows type-specific features in this region. For example, the man skilled in the art can easily determine in the region spanning amino acids 68 to 78 (V-core region) amino acids unique to the new HCV type according to the invention. The V-Core region of the new HCV type of the current invention thus also is a region unique to the HCV polyprotein as well as the HCV Core protein of the new HCV type of the invention. This V-Core region is defined by SEQ ID NO:57.

Likewise, the E1 protein of the new HCV type of the invention comprises unique variable regions including the V1 region (SEQ ID NO:58; encompassing amino acid positions 191 to 203 of the E1 protein of the new HCV type of the invention), the V2 region (SEQ ID NO:59; encompassing amino acid positions 213 to 223 of the E1 protein of the new HCV type of the invention), the V3 region (SEQ ID NO:60; encompassing amino acid positions 230 to 242 of the E1 protein of the new HCV type of the invention), the V4 region (SEQ ID NO:61; encompassing amino acid positions 248 to 257 of the E1 protein of the new HCV type of the invention), and the V6 region (SEQ ID NO:63; encompassing amino acid positions 330 to 342 of the E1 protein of the new HCV type of the invention). In contrast, the V5 region (SEQ ID NO:62; encompassing amino acid positions 294 to 303 of the E1 protein of the new HCV type of the invention) is not unique to the new HCV type of the invention as it is occurring in a type 5a HCV isolate as described in International Patent Application WO94/25601.

The herein given list of peptides of the new HCV type of the invention as well as parts thereof are particularly useful for treatment and vaccine and diagnostic development.

Also comprised in the present invention is any synthetic peptide (see below) or polypeptide containing in their peptidic chain at least an epitope, such as a lineair epitope, derived from any of the above-defined peptides of the new HCV type of the invention. Also comprised within the present invention is any synthetic peptide or polypeptide comprising in their peptidic chain at least 4, 5, 6, 7, 8, 9, 10, 11, 12 or 13 contiguous amino acids derived from any of the above-defined peptides of the new HCV type of the invention.

As used herein, 'epitope' or 'antigenic determinant' means an amino acid sequence that is immunoreactive. Generally an epitope consists of at least 3 to 4 amino acids, and more usually, consists of at least 5 or 6 amino acids, sometimes the epitope consists of about 7, 8 or 9, or even about 10 amino acids.

The present invention particularly relates to any peptide (see below) or polypeptide contained in any of the amino acid sequences as represented in SEQ ID NOs:3, 5, 7, 9, 11, 13, 15, or 50–63 (see Table 5 and FIGS. 1 and 2, Examples section).

The present invention also relates to a recombinant polypeptide encoded by a polynucleic acid as defined above, or a part thereof which is unique to any of the HCV subtypes or types as defined in Table 5, or an analog thereof being substantially homologous and biologically equivalent to said polypeptide.

The present invention also relates to a recombinant vector comprising a HCV polynucleic acid or a part thereof according to the invention. Such recombinant vector may be an expression vector capable of driving expression of a HCV peptide encoded by the HCV polynucleic acid comprised in said vector. In said expression vector, a HCV polynucleic acid or part thereof according to the invention may be operably linked to prokaryotic, eukaryotic or viral transcription and translation control elements.

In another aspect, the invention comprises a host cell comprising a HCV polynucleic acid or part thereof according to the invention or a host cell transformed with a recombinant vector as described above.

In general said recombinant vector will comprise a vector sequence, an appropriate prokaryotic, eukaryotic or viral promoter sequence followed by the nucleotide sequences as defined above, with said recombinant vector allowing the expression of any one of the polypeptides as defined above in a prokaryotic, or eukaryotic host or in living mammals when injected as naked DNA, and more particularly a recombinant vector allowing the expression of any of the new HCV sequences of the invention spanning particularly the following amino acid positions:

- a polypeptide starting in the region between positions 1 and 10 and ending at any position in the region between positions 70 and 420, more particularly a polypeptide spanning positions 1 to 70, 1 to 85, positions 1 to 120, positions 1 to 150, positions 1 to 191, or positions 1 to 200, for expression of the Core protein, and a polypeptide spanning positions 1 to 263, positions 1 to 326, positions 1 to 383, or positions 1 to 420 for expression of the Core and E1 protein;
- a polypeptide starting at any position in the region between positions 117 and 192, and ending at any position in the region between positions 263 and 420, for expression of E1, or forms that have the hydrophobic region deleted (positions 264 to 293 plus or minus 8 amino acids);
- a polypeptide starting at any position in the region between positions 1556 and 1688, and ending at any position in the region between positions 1739 and 1764, for expression of NS4, more particularly; a polypeptide starting at position 1658 and ending at position 1711, for expression of NS4a antigen, and more particularly, a polypeptide starting at position 1712 and ending in the region between positions 1743 and 1972 (for instance 1712–1743, 1712–1764, 1712–1782, 1712–1972, 1712–1782, 1712–1902), for expression of NS4b antigen or parts thereof.

Any other HCV vector construction known in the art may also be used for the recombinant polypeptides of the present invention.

Also any of the known purification methods for recombinant proteins may be used for the production of the recombinant polypeptides of the present invention, particularly the HCV recombinant polypeptide purification methods as disclosed in PCT/EP 95/03031 in name of Innogenetics N.V.

The term "vector" may comprise a plasmid, a cosmid, a phage, or a virus or a transgenic animal. Particularly useful for vaccine development may be BCG or adenoviral vectors, as well as avipox recombinant viruses.

The present invention also relates to a method for the production of a recombinant polypeptide as defined above, comprising:

- transformation of an appropriate cellular host with a recombinant vector, in which a polynucleic acid or a part thereof according to as defined above has been inserted under the control of appropriate regulatory elements,
- culturing said transformed cellular host under conditions enabling the expression of said insert, and,
- harvesting said polypeptide.

The term 'recombinantly expressed' used within the context of the present invention refers to the fact that the proteins of the present invention are produced by recombinant expression methods be it in prokaryotes, or lower or higher eukaryotes as discussed in detail below.

The term 'lower eukaryote' refers to host cells such as yeast, fungi and the like. Lower eukaryotes are generally (but not necessarily) unicellular. Preferred lower eukaryotes are yeasts, particularly species within *Saccharomyces, Schizosaccharomyces, Kluyveromyces, Pichia* (e.g. *Pichia pastoris*), *Hansenula* (e.g. *Hansenula polymorpha*), *Schwanniomyces, Zygosaccharomyces, Yarowia*, and the like. *Saccharomyces cerevisiae, S. carlsbergensis* and *K. lactis* are the most commonly used yeast hosts, and are convenient fungal hosts.

The term 'prokaryotes' refers to hosts such as *E.coli, Lactobacillus, Lactococcus, Salmonella, Streptococcus, Bacillus subtilis* or *Streptomyces*. Also these hosts are contemplated within the present invention.

The term 'higher eukaryote' refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

The term 'recombinant polynucleotide or nucleic acid' intends a polynucleotide or nucleic acid of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term 'recombinant host cells', 'host cells', 'cells', 'cell lines', 'cell cultures', and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

The term 'replicon' is any genetic element, e.g., a plasmid, a chromosome, a virus, a cosmid, etc., that behaves as an autonomous unit of polynucleotide replication within a cell; i.e., capable of replication under its own control.

The term 'vector' is a replicon further comprising sequences providing replication and/or expression of a desired open reading frame.

The term 'control sequence' refers to polynucleotide sequences which are necessary to effect the expression of coding sequences to which they are ligated. The nature of such control sequences differs depending upon the host organism; in prokaryotes, such control sequences generally include promoter, ribosomal binding site, splicing sites and terminators; in eukaryotes, generally, such control sequences include promoters, splicing sites, terminators and, in some instances, enhancers. The term 'control sequences' is intended to include, at a minimum, all components whose presence is necessary for expression, and may also include additional components whose presence is advantageous, for example, leader sequences which govern secretion.

The term 'promoter' is a nucleotide sequence which is comprised of consensus sequences which allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence 'operably linked' to a coding sequence is ligated in such a way that expression of the coding sequence is achieved under conditions compatible with the control sequences.

The segment of the HCV cDNA encoding the desired sequence inserted into the vector sequence may be attached to a signal sequence. Said signal sequence may be that from a non-HCV source, e.g. the IgG or tissue plasminogen activator (tpa) leader sequence for expression in mammalian cells, or the a-mating factor sequence for expression into yeast cells, but particularly preferred constructs according to the present invention contain signal sequences appearing in the HCV genome before the respective start points of the proteins.

A variety of vectors may be used to obtain recombinant expression of HCV single or specific oligomeric envelope proteins of the present invention. Lower eukaryotes such as yeasts and glycosylation mutant strains are typically transformed with plasmids, or are transformed with a recombinant virus. The vectors may replicate within the host independently, or may integrate into the host cell genome.

Higher eukaryotes may be transformed with vectors, or may be infected with a recombinant virus, for example a recombinant vaccinia virus. Techniques and vectors for the insertion of foreign DNA into vaccinia virus are well known in the art, and utilize, for example homologous recombination. A wide variety of viral promoter sequences, possibly terminator sequences and poly(A)-addition sequences, possibly enhancer sequences and possibly amplification sequences, all required for the mammalian expression, are available in the art. Vaccinia is particularly preferred since vaccinia halts the expression of host cell proteins. Vaccinia is also very much preferred since it allows the expression of, for instance E1 and E2 proteins of HCV in cells or individuals which are immunized with the live recombinant vaccinia virus. For vaccination of humans the avipox and Ankara Modified Virus (AMV) are particularly useful vectors.

Also known are insect expression transfer vectors derived from baculovirus *Autographa californica* nuclear polyhedrosis virus (AcNPV), which is a helper-independent viral expression vector. Expression vectors derived from this system usually use the strong viral polyhedrin gene promoter to drive the expression of heterologous genes. Different vectors as well as methods for the introduction of heterologous DNA into the desired site of baculovirus are available to the man skilled in the art for baculovirus expression. Also different signals for posttranslational modification recognized by insect cells are known in the art.

The present invention also relates to a host cell transformed with a recombinant vector as defined above.

The present invention also relates to a method for detecting antibodies to HCV present in a biological sample, comprising:

(i) contacting the biological sample to be analyzed for the presence of HCV with a polypeptide as defined herein,
(ii) detecting the immunological complex formed between said antibodies and said polypeptide.

The present invention also relates to a method for HCV typing, comprising:

(i) contacting the biological sample to be analyzed for the presence of HCV with a polypeptide as defined herein,
(ii) detecting the immunological complex formed between said antibodies and said polypeptide.

In any of the above methods of the invention, the biological sample is suspected or liable to contain HCV or antibodies to HCV.

The present invention also relates to a diagnostic kit for use in detecting the presence of HCV, said kit comprising at least one polypeptide as defined herein, with said polypeptide being preferably bound to a solid support. The present invention also relates to a diagnostic kit for HCV typing, said kit comprising at least one polypeptide as defined herein, with said polypeptide being preferably bound to a solid support.

The present invention also relates to diagnostic kit according as defined above, said kit comprising a range of said polypeptides which are attached to specific locations on a solid substrate.

The present invention also relates to a diagnostic kit as defined above, wherein said solid support is a membrane strip and said polypeptides are coupled to the membrane in the form of parallel lines.

The immunoassay methods according to the present invention may utilize antigens from the different domains of the new and unique polypeptide sequences of the present invention that maintain linear (in case of peptides) and conformational epitopes (in case of polypeptides) recognized by antibodies in the sera from individuals infected with HCV. It is within the scope of the invention to use for instance single or specific oligomeric antigens, dimeric antigens, as well as combinations of single or specific oligomeric antigens. The HCV antigens of the present invention may be employed in virtually any assay format that employs a known antigen to detect antibodies. Of course, a format that denatures the HCV conformational epitope should be avoided or adapted. A common feature of all of these assays is that the antigen is contacted with the body component suspected of containing HCV antibodies under conditions that permit the antigen to bind to any such antibody present in the component. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be, without limitation, in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon™), diazotized paper, nylon membranes, activated beads, and Protein A beads. For example, Dynatech Immunolon™ 1 or Immunlon™ 2 microtiter plates can be used in the heterogeneous format. The solid support containing the antigenic polypeptides is typically washed after separating it from the test sample, and prior to detection of bound antibodies. Both standard and competitive formats are know in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of HCV antibodies in the antibody-antigen complexes is directly monitored. This may be accomplished by determining whether labeled anti-xenogeneic (e.g. anti-human) antibodies which recognize an epitope on anti-HCV antibodies will bind due to complex formation. In a competitive format, the amount of HCV antibodies in the sample is deduced by monitoring the competitive effect on the binding of a known amount of labeled antibody (or other competing ligand) in the complex.

Complexes formed comprising anti-HCV antibody (or in the case of competitive assays, the amount of competing antibody) are detected by any of a number of known techniques, depending on the format. For example, unlabeled HCV antibodies in the complex may be detected using a conjugate of anti-xenogeneic Ig complexed with a label (e.g. an enzyme label).

In an immunoprecipitation or agglutination assay format the reaction between the HCV antigens and the antibody forms a network that precipitates from the solution or suspension and forms a visible layer or film of precipitate. If no anti-HCV antibody is present in the test specimen, no visible precipitate is formed.

There currently exist several specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen antibodies present in the body component, if any, causes the RBCs coated with the purified antigen to agglutinate. To eliminate potential non-specific reactions in the hemagglutination assay, two artificial carriers may be used instead of RBC in the PA. The most common of these are latex particles. However, gelatin particles may also be used. The assays utilizing either of these carriers are based on passive agglutination of the particles coated with purified antigens.

The HCV antigens of the present invention comprised of conformational epitopes will typically be packaged in the form of a kit for use in these immunoassays. The kit will normally contain in separate containers the native HCV antigen, control antibody formulations (positive and/or negative), labeled antibody when the assay format requires the same and signal generating reagents (e.g. enzyme substrate) if the label does not generate a signal directly. The native HCV antigen may be already bound to a solid matrix or separate with reagents for binding it to the matrix. Instructions (e.g. written, tape, CD-ROM, etc.) for carrying out the assay usually will be included in the kit.

Immunoassays that utilize the native HCV antigen are useful in screening blood for the preparation of a supply from which potentially infective HCV is lacking. The method for the preparation of the blood supply comprises the following steps. Reacting a body component, preferably blood or a blood component, from the individual donating blood with HCV polypeptides of the present invention to allow an immunological reaction between HCV antibodies, if any, and the HCV antigen. Detecting whether anti-HCV antibody-HCV antigen complexes are formed as a result of the reacting. Blood contributed to the blood supply is from donors that do not exhibit antibodies to the native HCV antigens.

In cases of a positive reactivity to the HCV antigen, it is preferable to repeat the immunoassay to lessen the possibility of false positives. For example, in the large scale screening of blood for the production of blood products (e.g. blood transfusion, plasma, Factor VIII, immunoglobulin, etc.) 'screening' tests are typically formatted to increase sensitivity (to insure no contaminated blood passes) at the expense of specificity; i.e. the false-positive rate is increased. Thus, it is typical to only defer for further testing those donors who are 'repeatedly reactive'; i.e. positive in two or more runs of the immunoassay on the donated sample. However, for confirmation of HCV-positivity, the 'confirmation' tests are typically formatted to increase specificity (to insure that no false-positive samples are confirmed) at the expense of sensitivity.

The solid phase selected can include polymeric or glass beads, nitrocellulose, microparticles, microwells of a reaction tray, test tubes and magnetic beads. The signal generating compound can include an enzyme, a luminescent compound, a chromogen, a radioactive element and a chemiluminescent compound. Examples of enzymes include alkaline phosphatase, horseradish peroxidase and beta-galactosidase. Examples of enhancer compounds include biotin, anti-biotin and avidin. Examples of enhancer compounds binding members include biotin, anti-biotin and avidin. In order to block the effects of rheumatoid factor-like substances, the test sample is subjected to conditions sufficient to block the effect of rheumatoid factor-like substances. These conditions comprise contacting the test sample with a quantity of anti-human IgG to form a mixture, and incubating the mixture for a time and under conditions sufficient to form a reaction mixture product substantially free of rheumatoid factor-like substance.

The present invention particularly relates to an immunoassay format in which the peptides or polypeptides of the invention are coupled to a membrane in the form of parallel lines. This assay format is particularly advantageous for HCV typing purposes.

The present invention also relates to a pharmaceutical composition comprising at least one (recombinant) polypeptide or peptide as defined herein and a suitable excipient, diluent or carrier.

The present invention also relates to a pharmaceutical composition according to the present invention for use in a method of preventing HCV infection, comprising administering said pharmaceutical composition to a mammal in an effective amount to stimulate the production of protective antibody or protective T-cell response.

The present invention relates to the use of a composition as defined herein in a method for preventing HCV infection.

The present invention further relates to a vaccine for immunizing a mammal against HCV infection, comprising at least one (recombinant) polypeptide or peptide as defined herein, in a pharmaceutically acceptable carrier.

In a further aspect, the invention relates to a pharmaceutical composition comprising at least one HCV polynucleic acid or fragment thereof according to the invention and a suitable excipient, diluent or carrier. Said compositions are suitable for use in a method of preventing or treating a HCV infection, comprising administering said pharmaceutical composition to a mammal in an effective amount to stimulate the production of protective antibody or protective T-cell response.

Another aspect of the invention relates to a DNA vaccine for immunizing a mammal against HCV infection, comprising at least one HCV polynucleic acid or fragment thereof according to the invention, and a pharmaceutically acceptable carrier.

Generally, DNA-comprising pharmaceutical compositions or vaccines enable expression of the encoded proteins or peptides, in the present invention of HCV proteins or peptides, in the host treated with said composition or vaccine, or after administering said composition or vaccine to said host.

The term 'immunogenic' or "immunizing" refers to the ability of a substance to cause a humoral and/or cellular response, whether alone or when linked to a carrier, in the presence or absence of an adjuvant. 'Neutralization' refers to an immune response that blocks the infectivity, either partially or fully, of an infectious agent. A 'vaccine' is an immunogenic composition capable of eliciting protection against HCV, whether partial or complete. A vaccine may also be useful for treatment of an individual, in which case it is called a therapeutic vaccine.

The term 'therapeutic' refers to a composition capable of treating HCV infection.

The term 'effective amount' refers to an amount of epitope-bearing polypeptide sufficient to induce an immunogenic response in the individual to which it is administered, or to otherwise detectable immunoreact in its intended system (e.g., immunoassay). Preferably, the effective amount is sufficient to effect treatment, as defined above. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation. Preferred ranges of proteins for prophylaxis of HCV disease are 0.01 to 100 µg/dose, preferably 0.1 to 50 µg/dose. Several doses may be needed per individual in order to achieve a sufficient immune response and subsequent protection against HCV disease.

The present invention also relates to a vaccine as defined above, comprising at least one (recombinant) polypeptide as defined herein, with said polypeptide being unique for the new HCV type as defined above. Said vaccine may include prophylactic as well as therapeutic vaccines.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art.

Preferred adjuvants to enhance effectiveness of the composition include, but are not limited to: aluminum hydroxide (alum), N-acetyl-muramyl-L-threonyl-D-isoglutamine (thr-MDP) as found in U.S. Pat. No. 4,606,918, N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE) and RIBI, which contains three components extracted from bacteria, monophosphoryl lipid A, trehalose dimycolate, and cell wall skeleton (MPL+TDM+

CWS) in a 2% squalene/Tween 80 emulsion. Any of the 3 components MPL, TDM or CWS may also be used alone or combined 2 by 2. Additionally, adjuvants such as Stimulon (Cambridge Bioscience, Worcester, Mass.).

Immunogenic compositions used as vaccines comprise a 'sufficient amount' or 'an immunologically effective amount' of the proteins of the present invention, as well as any other of the above mentioned components, as needed. 'Immunologically effective amount', means that the administration of that amount to an individual, either in a single dose or as part of a series, is effective for treatment, as defined above. This amount varies depending upon the health and physical condition of the individual to be treated, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, the strain of infecting HCV, and other relevant factors. It is expected that the amount will fall in a relatively broad range that can be determined through routine trials. Usually, the amount will vary from 0.01 to 1000 μg/dose, more particularly from 0.1 to 100 μg/dose.

The proteins of the invention may also serve as vaccine carriers to present homologous (e.g. T cell epitopes or B cell epitopes from, for instance, the core, E1, E2, NS2, NS3, NS4 or NS5 regions) or heterologous (non-HCV) haptens, in the same manner as Hepatitis B surface antigen (see for example European Patent Application EP-0 174 444). In this use, envelope proteins provide an immunogenic carrier capable of stimulating an immune response to haptens or antigens conjugated to the aggregate. The antigen may be conjugated either by conventional chemical methods, or may be cloned into the gene encoding E1 and/or E2 at a location corresponding to a hydrophilic region of the protein. Such hydrophilic regions include the V1 region (encompassing amino acid positions 191 to 203), the V2 region (encompassing amino acid positions 213 to 223), the V3 region (encompassing amino acid positions 230 to 242), the V4 region (encompassing amino acid positions 248 to 257), the V5 region (encompassing amino acid positions 294 to 303) and the V6 region (encompassing amino acid positions 330 to 342). Another useful location for insertion of haptens is the hydrophobic region (encompassing approximately amino acid positions 264 to 293). It is shown in the present invention that this region can be deleted without affecting the reactivity of the deleted E1 protein with antisera. Therefore, haptens may be inserted at the site of the deletion.

The immunogenic compositions are conventionally administered parentally, typically by injection, for example, subcutaneously or intramuscularly. Additional formulations suitable for other methods of administration include oral formulations and suppositories. Dosage treatment may be a single dose schedule or a multiple dose schedule. The vaccine may be administered in conjunction with other immunoregulatory agents. The administration of the immunogen(s) of the present invention may be for either a prophylactic or therapeutic purpose. When provided prophylactically, the immunogen(s) is provided in advance of any exposure to HCV or in advance of any symptom of any symptoms due to HCV infection. The prophylactic administration of the immunogen serves to prevent or attenuate any subsequent infection of HCV in a mammal. When provided therapeutically, the immunogen(s) is provided at (or shortly after) the onset of the infection or at the onset of any symptom of infection or disease caused by HCV. The therapeutic administration of the immunogen(s) serves to attenuate the infection or disease.

In addition to use as a vaccine, the compositions can be used to prepare antibodies to HCV (E1) proteins. The antibodies can be used directly as antiviral agents. To prepare antibodies, a host animal is immunized using the E1 proteins native to the virus particle bound to a carrier as described above for vaccines. The host serum or plasma is collected following an appropriate time interval to provide a composition comprising antibodies reactive with the (E1) protein of the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs.

The present invention also relates particularly to a peptide corresponding to an amino acid sequence encoded by at least one of the HCV genomic sequences as defined above, with said peptide being unique to the new HCV type according to the invention, as defined in Table 5, and which contains at least one amino acid differing from any of the known HCV types or subtypes, or an analog thereof being substantially homologous and biologically equivalent.

The present invention relates particularly to a peptide comprising at least one unique epitope of the new sequences of the invention as represented in SEQ ID NOs:3, 5, 7, 9, 11, 13, 15, or 50–63.

The present invention relates also particularly to a peptide comprising in its sequence a unique amino acid residue of the invention as defined herein.

The present invention relates particularly to a peptide which is biotinylated as explained in WO 93/18054.

All the embodiments (immunoassay formats, vaccines, compositions, uses, etc.) illustrated for the polypeptides of the invention as above also relate to the peptides of the invention.

The present invention also relates to a method for detecting antibodies to HCV present in a biological sample, comprising:
(i) contacting the biological sample to be analyzed for the presence of HCV with a peptide as defined herein,
(ii) detecting the immunological complex formed between said antibodies and said peptide.

The present invention also relates to a method for HCV typing, comprising:
(i) contacting the biological sample to be analyzed for the presence of HCV with a peptide as defined herein,
(ii) detecting the immune complex formed between said antibodies and said peptide.

In any of the above methods of the invention, the biological sample is suspected or liable to contain HCV or antibodies to HCV.

The present invention also relates to a diagnostic kit for use in detecting the presence of HCV, said kit comprising at least one peptide as defined herein, with said peptide being preferably bound to a solid support.

The present invention also relates to a diagnostic kit for HCV typing, said kit comprising at least one peptide as defined herein, with said peptide being preferably bound to a solid support.

The present invention also relates to a diagnostic kit as defined above, wherein said peptides are selected from the following:
  at least one NS4 peptide,
  at least one NS4 peptide and at least one Core peptide, at least one NS4 peptide and at least one Core peptide and at least one E1 peptide, at least one NS4 peptide and at least one E1 peptide, at least one NS5 peptide, and at least one NS5 peptide and at least one Core peptide.

The present invention also relates to a diagnostic kit as defined above, said kit comprising a range of said peptides which are attached to specific locations on a solid substrate.

The present invention also relates to a diagnostic kit as defined above, wherein said solid support is a membrane strip and said peptides are coupled to the membrane in the form of parallel lines.

The present invention relates also to a vaccine as defined above, comprising at least one peptide as defined above, with said peptide being unique for the new HCV type according to the invention, as defined in Table 5.

Furthermore, the present invention relates to an antibody raised upon immunization with at least one polypeptide or peptide as defined herein, with said antibody being specifically reactive with any of said polypeptides or peptides, and with said antibody being preferably a monoclonal antibody.

The monoclonal antibodies of the invention can be produced by any hybridoma liable to be formed according to classical methods from splenic cells of an animal, particularly from a mouse or rat, immunized against the HCV polypeptides according to the invention as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labeled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains or from cDNA clones coding for H and L chains.

Alternatively, the monoclonal antibodies according to this preferred embodiment of the invention may be human monoclonal antibodies. These antibodies according to the present embodiment of the invention can also be derived from human peripheral blood lymphocytes of patients infected with the new HCV type according to the invention, or vaccinated against HCV. Such human monoclonal antibodies are prepared, for instance, by means of human peripheral blood lymphocytes (PBL) repopulation of severe combined immune deficiency (SCID) mice (for recent review, see Duchosal et al. 1992) or by screening Epstein Barr-virus-transformed lymphocytes of infected or vaccinated individuals for the presence of reactive B-cells by means of the antigens of the present invention.

The invention also relates to the use of the proteins of the invention, muteins thereof, or peptides derived therefrom for the selection of recombinant antibodies by the process of repertoire cloning (Persson et al., 1991).

Antibodies directed to peptides derived from a certain genotype may be used either for the detection of such HCV genotypes, or as therapeutic agents.

The present invention relates also to a method for detecting HCV antigens present in a biological sample, comprising:

(i) contacting said biological sample with an antibody as defined herein, (ii) detecting the immune complexes formed between said HCV antigens and said antibody.

The present invention relates also to a method for HCV typing present in a biological sample, comprising:

(i) contacting said biological sample with an antibody as defined herein, (ii) detecting the immune complexes formed between said HCV antigens and said antibody.

In any of the above methods of the invention, the biological sample is suspected or liable to contain HCV or its antigens.

The present invention relates also to a diagnostic kit for use in detecting the presence of HCV, said kit comprising at least one antibody as defined above, with said antibody being preferably bound to a solid support.

The present invention relates also to a diagnostic kit for HCV typing, said kit comprising at least one antibody as defined herein, with said antibody being preferably bound to a solid support.

The present invention relates also to a diagnostic kit as defined herein, said kit comprising a range of said antibodies which are attached to specific locations on a solid substrate.

The present invention relates also to a pharmaceutical composition comprising at least one antibody as defined herein and a suitable excipient, diluent or carrier.

The present invention relates also to a method of preventing or treating HCV infection, comprising administering the pharmaceutical composition as defined herein to a mammal in effective amount.

The present invention relates also to the use of a composition as defined herein in a method for preventing or treating HCV infection.

The genotype may also be detected by means of a type-specific antibody as defined herein, which may also linked to any polynucleotide sequence that can afterwards be amplified by PCR to detect the immune complex formed (Immuno-PCR, Sano et al., 1992).

The present invention relates in particular to the 5'NCR (non-coding region). It will be understood that the terms "5'NCR", "5' non-coding region", "5'UTR" and "5' untranslated region" are used interchangeably herein.

The present invention relates in particular to a polynucleic acid according to the present invention or a part of said polynucleic acid, or the complement of said polynucleic acid or said part, comprising in its nucleotide sequence at least the following nucleotide residue: A171, with the notation being composed of a letter representing the nucleotide residue by its one-letter code, and a number representing the nucleotide numbering as shown in Table 1, or a part of said polynucleic acid containing at least said nucleotide residue, or the complement of said polynucleic acid or said part. Alternatively, A171 can be indicated as the adenine nucleotide at position −159 of the HCV genome (see above).

The present invention relates in particular to an HCV virus characterized by any of the following 5'UTR nucleotide sequences: SEQ ID NO:1.

The present invention relates in particular to a method for detecting the presence of an infection with a virus to the present invention in a biological sample.

The present invention relates in particular to a method for detecting the presence of an infection with a virus to the present invention in a biological sample on the basis of the presence of a genotype-specific sequence or an isolate-specific mutation present in SEQ ID NO:1.

The present invention relates in particular to a method for detecting the presence of an infection with a virus to the present invention in a biological sample on the basis of the presence of at least part of SEQ ID NOs:1, 2, 4, 6, 8, 10, 12, 14, or 36–49.

The present invention relates in particular to the method as defined herein, wherein said method comprises a sequencing reaction, a hybridization reaction or an amplification reaction.

The present invention relates in particular to a method comprising the determination of the presence in a biological sample of at least one of the following variable nucleotide regions or positions of any HCV 5'UTR sequence by means of a sequencing, hybridization or amplification reaction, wherein said method detects any nucleotide variation present between HCV strains in at least one of the following regions of HCV: the type-specific variable region between positions 43 and 298

The present invention relates in particular to a method as defined herein, wherein said method comprises the determination of said nucleotide variations present in said region of SEQ ID NO:1.

The present invention relates in particular to a method as defined herein, wherein said method comprises the determination of at least one of the following nucleotides of any of the following sequences: A at position 171 in SEQ ID NO:1. Alternatively, A171 can be indicated as the adenine nucleotide at position −159 of the HCV genome (see above).

The present invention relates in particular to a method as defined herein, for identifying sequences of the new HCV type according to the invention.

The present invention relates in particular to an HCV genotyping method comprising the steps of a method as defined herein.

The present invention relates in particular to a method as defined herein, wherein said hybridization reaction is carried out with hybridization probes which are coupled to a solid support and wherein said probes are optionally capture probes.

The present invention relates in particular to a method for amplification of an HCV genomic sequence isolated from an HCV virus as defined herein.

The present invention relates in particular to a method as defined herein, wherein said amplification method is PCR, LCR, NASBA, TAS, or amplification by means of Qβ replicase.

The present invention relates in particular to a method as defined herein, wherein an appropriate label is incorporated during said amplification reaction.

The present invention relates in particular to an isolated HCV 5'UTR nucleic acid comprising a region comprised in SEQ ID NO:1, or the complement thereof, wherein said region contains a strain-, isolate- or genotype-specific nucleotide sequence.

The present invention relates in particular to a nucleic acid sequence as defined herein which acts as a hybridization probe.

The present invention relates in particular to a nucleic acid as defined herein, which acts as a type or subtype-specific probe.

The present invention relates in particular to a nucleic acid as defined herein, which targets at least part of any of the following genotype-specific motifs characterized by SEQ ID NO:1, or the complement thereof.

The present invention relates in particular to a nucleic acid as defined herein, which targets at least part of any of the following universal motifs characterized by SEQ ID NO:1, or the complement thereof.

The present invention relates in particular to a nucleic acid as defined herein, which comprises a label and/or which is coupled to a solid support.

The present invention relates in particular to a nucleic acid as defined herein, which acts as a specific amplification primer.

The present invention relates in particular to a nucleic acid as defined herein, which is a capture probe.

The present invention relates also to an HCV genotype comprising at least one virus characterized by a genome comprising a 5'UTR region defined by SEQ ID NO:1 or part of the NS5 nucleic acid region defined by SEQ ID NO:8.

The present invention relates also to a method for detecting the presence of an infection with an HCV virus or genotype as defined herein in a biological sample.

The present invention relates also to a method for detecting the presence of an infection with a virus as defined herein in a biological sample on the basis of the presence of a genotype-specific sequence or an isolate-specific mutation present in a nucleic acid encoding SEQ ID NO:8.

The present invention relates also to a method for detecting the presence of an infection with a virus as defined herein in a biological sample on the basis of the presence of at least part of a nucleic acid sequence encoding SEQ ID NO:8.

The present invention relates also to a method as defined herein, wherein said hybridization reaction is carried out with hybridization probes which are coupled to a solid support, preferably a membrane, and wherein said probes are optionally capture probes.

The present invention relates also to an isolated HCV NS5 nucleic acid encoding a region comprised in an amino acid sequence selected from SEQ ID NO:9, wherein said region contains a strain-, isolate- or genotype-specific nucleotide sequence.

The present invention relates also to a polypeptide or peptide comprising at least part of SEQ ID NO:9, wherein said part is specific for a virus comprising in its genome part of the NS5 nucleic acid region defined by SEQ ID NO:8.

The present invention relates also to a method for detecting the presence of an infection with an HCV virus as defined herein, comprising detection of the presence of an amino acid sequence, polypeptide or peptide as defined herein.

The present invention relates also to the use of a nucleic acid as defined herein for the detection of HCV.

The present invention relates also to the use of a nucleic acid as defined herein for the determination of an HCV genotype.

The present invention relates also to a diagnostic kit for the detection of HCV in a biological sample comprising an HCV 5'UTR nucleic acid as defined herein.

The present invention relates also to a diagnostic kit for the detection of HCV in a biological sample comprising an HCV NS5 nucleic acid as defined herein.

The present invention relates also to a diagnostic kit for the detection of HCV in a biological sample comprising an HCV NS5 amino acid sequence, a peptide or a polypeptide as defined herein.

The present invention relates also to a diagnostic kit allowing the detection of an HCV virus as defined herein.

The present invention relates also to a diagnostic kit for use with a method as defined herein.

Any publications or patent applications referred to herein are incorporated by reference. The following examples illustrate aspects of the invention but are in no way intended to limit the scope thereof.

EXAMPLES

Example 1

Genotyping of the Sample with the INNO-LiPA HCV II

Starting from a serum sample originating from the US (IG57272), RNA isolation, cDNA Synthesis, PCR, and genotyping using the INNO-LiPA HCV II genotyping assay were performed as described by the manufacturer (Innogenetics NV, Zwijnaarde, Belgium). On the LiPA strip, an unusual line pattern (positive lines 1, 2 and 6), which could not be attributed to any described genotype, was seen.

Example 2

Sequencing of the 5'NCR, Core and NS5B Regions of Sample IG57272

For the determination of the sequence of the 5'NCR region of IG57272, a 300 bp 5'NCR fragment was amplified as described in Stuyver et al. (1996). This PCR fragment was subsequently cloned in a pGEM-T vector (Promega Corp., USA) and clones were sequenced using vector SP6/T7 primers. The resulting 5' NCR sequence is depicted in FIG. 1.A.

For the determination of the sequence of the Core region of IG57272, a 1172 bp Core/E1 fragment was amplified using primers HCPr52, HCPr54, HCPr634, HCPr635, HCPr636, HCPr637, HCPr638, HCPr639, HCPr640, HCPr641, HCPr666, HCPr667. All possible combinations of primers were analyzed but only the combination of primers HCPr666/HCPr635 for the outer PCR and HCPr667/HCPr637 for nested PCR was able to produce the desired PCR fragment. This PCR fragment was subsequently cloned in a pGEM-T vector (Promega Corp., USA) and clones were sequenced using vector SP6/T7 primers. The resulting Core nucleic acid sequences from 3 individual clones, i.e. clone 28454 (SEQ ID NO:2), clone 28452 (SEQ ID NO:4) and clone 28451 (SEQ ID NO:6), are depicted in FIGS. 1.B and 1.C. The amino acid sequences deduced from these Core nucleic acid sequences of these 3 individual clones, i.e. clone 28454 (SEQ ID NO:3), clone 28452 (SEQ ID NO:5) and clone 28451 (SEQ ID NO:7), are depicted in FIGS. 1.B and 1.C. The resulting Core/E1 nucleic acid sequences from 3 additional individual clones, i.e. clone 33400 (SEQ ID NO:10), clone 33402 (SEQ ID NO:12) and clone 33403 (SEQ ID NO:14), are depicted in the alignment as shown in FIG. 4. The amino acid deduced from these Core/E1 nucleic acid sequences from 3 individual clones, i.e. clone 33400 (SEQ ID NO:11), clone 33402 (SEQ ID NO:13) and clone 33403 (SEQ ID NO:15), are depicted in the alignment as shown in FIG. 2. The latter Clustal W (1.8) multiple sequence alignment of the amino acid sequences deduced from clones 28454, 28452, 28451, 33400, 33402 and 33403 shows differences only between said three clones at positions 7 and 52.

For determination of the sequence of the NS5B region of IG57272, a 400 bp NS5B fragment was amplified using primers HCPr292 and HCPr295, followed by a nested PCR with primers HCPr293 and HCPr294, resulting in a final NS5B fragment of 380 bp. This NS5B PCR fragment was isolated from a 1.5% LMT agarose gel and used for cycle sequencing using primers HCPr293 and HCPr294. The resulting NS5B nucleic acid sequence (SEQ ID NO:8) is depicted in FIG. 1.D. The amino acid sequence deduced thereof (SEQ ID NO:9) is also shown in FIG. 1.D.

The primers used for cloning are depicted below:

| SEQ ID NO: | HCPr No. | Primer sequence (5' to 3') |
|---|---|---|
| 16 | 29 | GCTCATG(A/G)TGCACGGTCTACGAGACCT |
| 17 | 52 | ATGTTGGGTAAGGTCATCGATACCCT |
| 18 | 54 | CTATTACCAGTTCATCATCATATCCCA |
| 19 | 95 | TCTAGCCATGGCGTTAGT(A/T)(G/T)GAGTGT |
| 20 | 96 | CACTCGCAAGCACCCTATCAGGCAGT |
| 21 | 98 | CCCTGTGAGGAACT(C/G)CTGTCTTCACGC |
| 22 | 292 | CCCTATGGGCTTCTCGTATGA |
| 23 | 293 | TATGACACCCGCTGCTTTGACTC |
| 24 | 294 | CCTGGTCATAGCCTCCGTGAA |
| 25 | 295 | GGGGCCGAGTACCTGGTCAT |
| 26 | 634 | CTCTCTTGC(G/T)TGACTGTGCCCGC |
| 27 | 635 | CGCGTCGACGCCGGCAAATAGCAGC |
| 28 | 636 | GC(G/T)TGACTGTGCCCGCTTC(A/T)GCC |
| 29 | 637 | TCGACGCCGGCAAA(G/T)AGCA(A/T)CAGCAC |
| 30 | 638 | CTGTC(G/T)TG(G/T)TTGACC(A/T)TCCCAGC |
| 31 | 639 | CCCGTCAACGCCGGC(A/T)AAGAGTA(A/T)C |

-continued

| SEQ ID NO: | HCPr No. | Primer sequence (5' to 3') |
|---|---|---|
| 32 | 640 | GT(G/T)TGACCA(G/T)CCCAGCTTCCGCT |
| 33 | 641 | TCAACGCCGGC(A/T)AA(A/T)AGTA(A/T)C(A/T)(G/T)CAC |
| 34 | 666 | ACTGCCTGATAGGGTGCTTGCGAG |
| 35 | 667 | CCCGGGAGGTCTCGTAGACC |

Example 3

Phylogenetic Analysis

Previously published sequences were taken from the EMBL/Genbank database. Alignments were created using the program HCVALIGN (Stuyver et al. 1994c) or GENEBASE (Applied Maths, Kortrijk, Belgium). Phylogenetic tree construction was done using the programs TREECON and GENEBASE. The resulting phylogenetic tree is depicted in FIG. 3.

Example 4

Identification of a New HCV Genotype

Isolate IG57272 did not cluster with any of the known 12 genotypes of HCV (see Example 3). IG57272 seems to be very distantly related to other Clade 6 genotypes (genotypes 6, 7, 8, 9, 11), but phylogenetic analysis indicated that isolate IG57272 should be assigned a new genotype. Depending on international guidelines for assigning type and subtype levels, IG57272 may be classified as HCV genotype 13.

TABLE 6

Overview of protein and nucleotide regions of the new HCV type according to the invention with indication of the corresponding SEQ ID NO:, the region of the fragment in the HCV polyprotein or genome (see Figures for numbering of amino acids and nucleotides), the region of the fragment in the SEQ ID NO: (i.e. length of the sequence defined by the SEQ ID NO:), and the % identity a given HCV sequence at least must have with a sequence of the new HCV type according to the invention.

| HCV protein region and corresponding SEQ ID NO: | Fragment of HCV protein region | Fragment of SEQ ID NO: (SEQ ID NO of fragment) | % identity |
|---|---|---|---|
| Core; SEQ ID NOs: 53–55 | 1–191 | 1–191 | >92% |
| E1; SEQ ID NO: 56 | 192–373 | 1–182 | >79% |
| Core/E1; SEQ ID NOs: 11, 13, 15 | 1–373 | 1–373 | >85% |
| Core/E1 [17–209]; SEQ ID NOs: 50–52 | 17–209 | 1–193 | >91% |
| NS5B; SEQ ID NO: 9 | 2647–2753 | 1–107 | >87% |

TABLE 5

An overview of the different clones, their nucleic acid and amino acid sequence positions in the genome and polyprotein of the new HCV type according to the invention, and their SEQ ID NOs is given in the Table below. Also given are the sequence positions, SEQ ID NOs and regions of a number of fragments of the genome or protein of the new HCV type according to the invention. All sequences were obtained from the IG57272 HCV-isolate.

| Clone | nucleotide sequence position | SEQ ID NO: | Region | Clone | Amino acid sequence position | SEQ ID NO: | Region |
|---|---|---|---|---|---|---|---|
|  | 31–329 | 1 | 5'UTR | 28454 | 1–209 | 3 | Core/partial E1 |
| 28454 | 330–957 | 2 | Core/partial E1 | 28452 | 1–161 | 5 | partial Core |
| 28452 | 330–813 | 4 | partial Core | 28451 | 1–209 | 7 | Core/partial E1 |
| 28451 | 330–957 | 6 | Core/partial E1 |  | 2647–2753 | 9 | NS5B |
|  | 8267–8590 | 8 | NS5B | 30400 | 1–373 | 11 | Core/E1 |
| 30400 | 323–1448 | 10 | Core/E1 | 30402 | 1–373 | 13 | Core/E1 |
| 30402 | 323–1448 | 12 | Core/E1 | 30403 | 1–373 | 15 | Core/E1 |
| 30402 | 323–1448 | 14 | Core/E1 | 30400 | 17–209 | 50 | Core/partial E1 |
| 30400 | 378–957 | 36 | Core/partial E1 | 30402 | 17–209 | 51 | Core/partial E1 |
| 30402 | 378–957 | 37 | Core/partial E1 | 30403 | 17–209 | 52 | Core/partial E1 |
| 30403 | 378–957 | 38 | Core/partial E1 | 30400 | 1–191 | 53 | Core |
| 30400 | 330–902 | 39 | Core | 30402 | 1–191 | 54 | Core |
| 30402 | 330–902 | 40 | Core | 30403 | 1–191 | 55 | Core |
| 30403 | 330–902 | 41 | Core |  | 192–373 | 56 | E1 |
|  | 903–1448 | 42 | E1 |  | 68–78 | 57 | V–Core |
|  | 531–563 | 43 | V–Core |  | 191–203 | 58 | V1 |
|  | 903–938 | 44 | V1 |  | 213–223 | 59 | V2 |
|  | 966–998 | 45 | V2 |  | 230–242 | 60 | V3 |
|  | 1017–1055 | 46 | V3 |  | 248–257 | 61 | V4 |
|  | 1071–1100 | 47 | V4 |  | 294–303 | 62 | V5 |
|  | 1209–1238 | 48 | V5 |  | 330–342 | 63 | V6 |
|  | 1317–1355 | 49 | V6 |  |  |  |  |

TABLE 6-continued

| HCV nucleic acid region and corresponding SEQ ID NO: | Fragment of HCV nucleic acid region | Fragment of SEQ ID NO: | % identity |
|---|---|---|---|
| 5'UTR; SEQ ID NO: 1 | 31–328 | 1–298 | >99% |
| Core; SEQ ID NOs: 39–41 | 330–902 | 1–573 | >85% |
| E1; SEQ ID NO: 42 | 903–1448 | 1–546 | >71% |
| Core/E1; SEQ ID NOs: 10, 12, 14 | 330–1448 | 1–1119 | >78% |
| Core/E1 [378–957]; SEQ ID NOs: 36–38 | 378–957 | 1–580 | >84% |
| NS5B; SEQ ID NO: 8 | 8267–8590 | 1–324 | >75% |

TABLE 7

Overview of fragments of the E1 nucleotide sequence with SEQ ID NO: 42 of the new HCV type according to the invention with indication of the region of the fragment in SEQ ID NO: 42 (i.e. SEQ ID NO: 42 is a sequence of 546 nucleotides numbered as 1 to 546), and the % identity a given HCV sequence at least must have with the E1 fragment of the new HCV type according to the invention.

| E1 fragment Fragment of SEQ ID NO: 42 | % identity | E1 fragment Fragment of SEQ ID NO: 42 | % identity |
|---|---|---|---|
| 19–92 | 85% | 337–400 | 85% |
| 26–63 | 89% | 337–407 | 88% |
| 208–282 | 84% | 337–413 | 87% |
| 220–272 | 88% | 340–407 | 86% |
| 223–282 | 83% | 340–413 | 86% |
| 241–272 | 90% | 346–407 | 90% |
| 307–410 | 92% | 349–407 | 86% |
| 316–406 | 82% | 358–410 | 88% |
| 316–407 | 83% | 365–413 | 93% |
| 323–407 | 85% | 367–407 | 95% |
| 325–407 | 85% | 367–410 | 93% |
| 327–410 | 84% | 368–407 | 95% |
| 328–407 | 83% | 370–407 | 92% |
| 328–410 | 85% | 370–410 | 92% |
| 328–413 | 86% | 373–407 | 97% |
| 329–407 | 83% | 373–413 | 95% |
| 330–400 | 84% | 373–415 | 95% |
| 330–401 | 84% | 376–410 | 94% |
| 330–407 | 83% | 376–413 | 94% |
| 330–410 | 83% | 379–407 | 93% |
| 331–407 | 81% | 379–410 | 96% |
| 331–410 | 83% | 379–419 | 95% |
| 334–407 | 86% | 510–540 | 93% |
| 335–407 | 84% | | |

TABLE 8

Overview of fragments of the NS5B nucleotide sequence with SEQ ID NO: 8 of the new HCV type according to the invention with indication of the region of the fragment in SEQ ID NO: 8 (i.e. SEQ ID NO: 8 is a sequence of 324 nucleotides numbered as 1 to 324), and the % identity a given HCV sequence at least must have with the NS5B fragment of the new HCV type according to the invention.

| NS5B fragment Fragment of SEQ ID NO: 8 | % identity | NS5B fragment Fragment of SEQ ID NO: 8 | % identity | NS5B fragment Fragment of SEQ ID NO: 8 | % identity |
|---|---|---|---|---|---|
| 23–48 | 96% | 121–216 | 82% | 155–222 | 83% |
| 26–62 | 89% | 122–216 | 80% | 158–217 | 85% |
| 26–123 | 80% | 138–207 | 87% | 161–218 | 86% |
| 26–195 | 79% | 138–208 | 84% | 177–207 | 96% |
| 34–240 | 81% | 138–213 | 82% | 177–208 | 93% |
| 59–217 | 80% | 139–162 | 95% | 177–213 | 91% |
| 71–216 | 80% | 139–168 | 93% | 177–216 | 90% |
| 83–207 | 80% | 139–180 | 90% | 179–208 | 93% |
| 82–208 | 81% | 139–184 | 86% | 179–216 | 89% |
| 86–124 | 89% | 139–201 | 87% | 182–207 | 96% |
| 86–133 | 87% | 139–213 | 88% | 182–208 | 96% |
| 86–198 | 81% | 139–216 | 83% | 191–216 | 96% |
| 86–206 | 80% | 140–184 | 88% | 247–297 | 84% |
| 89–162 | 82% | 146–207 | 87% | 256–279 | 95% |
| 89–198 | 82% | 146–210 | 89% | 256–282 | 96% |
| 89–216 | 79% | 146–216 | 88% | 256–290 | 91% |
| 92–162 | 84% | 149–198 | 86% | 256–297 | 88% |
| 92–165 | 82% | 149–207 | 84% | 256–298 | 90% |
| 92–216 | 80% | 149–208 | 86% | 256–299 | 90% |
| 104–195 | 81% | 152–217 | 83% | 256–303 | 87% |
| 194–207 | 80% | 153–207 | 85% | 257–282 | 96% |
| 107–216 | 81% | 155–204 | 88% | 257–291 | 93% |
| 110–180 | 84% | 155–207 | 86% | 257–298 | 90% |
| 110–240 | 81% | 155–208 | 87% | 257–303 | 91% |
| 121–162 | 88% | 155–216 | 83% | 272–294 | 95% |
| | | 155–217 | 84% | 272–298 | 92% |

REFERENCES

1. Agarwal et al. (1972) *Agnew Chem Int Ed Engl* 11, 451.
2. Asseline, U., Delarue, M., Lancelot, G., Toulme, F., Thuong, N. T., Montenay-Garestier, T., and Helene, C. (1984) *Proc. Natl. Acad. Sci. U.S.A* 81, 3297–3301.
3. Beaucage, S. L. and Caruthers, M. H. (1981) *Tetrahedron Lett* 22, 1859–1862.
4. Bej, A. K., Mahbubani, M. H., Miller, R., DiCesare, J. L., Haff, L., and Atlas, R. M. (1990) *Mol Cell Probes* 4, 353–365.
5. Bukh, J., Purcell, R. H., and Miller, R. H. (1993) *Proc. Natl. Acad. Sci. U.S.A* 90, 8234–8238.
6. Cha, T. A., Beall, E., Irvine, B., Kolberg, J., Chien, D., Kuo, G., and Urdea, M. S. (1992) *Proc. Natl. Acad. Sci. U.S.A* 89, 7144–7148.
7. Chan, S. W., Simmonds, P., McOmish, F., Yap, P. L., Mitchell, R., Dow, B., and Follett, E. (1991) *Lancet* 338, 1391.
8. Chan, S. W., McOmish, F., Holmes, E. C., Dow, B., Peutherer, J. F., Follett, E., Yap, P. L., and Simmonds, P. (1992) *J. Gen Virol.* 73 (Pt 5), 1131–1141.
9. Choo, Q. L., Richman, K. H., Han, J. H., Berger, K., Lee, C., Dong, C., Gallegos, C., Coit, D., Medina-Selby, R., Barr, P. J., and. (1991) *Proc. Natl. Acad. Sci. U.S.A* 88, 2451–2455.
10. Compton, J. (1991) *Nature* 350, 91–92.
11. Cusi, M. G., Valassina, M., and Valensin, P. E. (1994) *Biotechniques* 17, 1034–1036.
12. Duchosal, M. A., Eming, S. A., Fischer, P., Leturcq, D., Barbas, C. F., III, McConahey, P. J., Caothien, R. H., Thornton, G. B., Dixon, F. J., and Burton, D. R. (1992) *Nature* 355, 258–262.
13. Duck, P., Alvarado-Urbina, G., Burdick, B., and Collier, B. (1990) *Biotechniques* 9, 142–148.

14. Gingeras, T. R., Whitfield, K. M., and Kwoh, D. Y. (1990) *Ann. Biol Clin (Paris.)* 48, 498–501.
15. Guatelli, J. C., Whitfield, K. M., Kwoh, D. Y., Barringer, K. J., Richman, D. D., and Gingeras, T. R. (1990) *Proc. Natl. Acad. Sci. U.S.A* 87, 1874–1878.
16. Hsiung, H. M., Brousseau, R., Michniewicz, J., and Narang, S. A. (1979) *Nucleic Acids Res* 6, 1371–1385.
17. Jacobs, K. A., Rudersdorf, R., Neill, S. D., Dougherty, J. P., Brown, E. L., and Fritsch, E. F. (1988) *Nucleic Acids Res* 16, 4637–4650.
18. Kato, N., Hijikata, M., Ootsuyama, Y., Nakagawa, M., Ohkoshi, S., Sugimura, T., and Shimotohno, K. (1990) *Proc. Natl. Acad. Sci. U.S.A* 87, 9524–9528.
19. Kievits, T., van Gemen, B., van Strijp, D., Schukkink, R., Dircks, M., Adriaanse, H., Malek, L., Sooknanan, R., and Lens, P. (1991) *J Virol Methods* 35, 273–286.
20. Kwoh, D. Y., Davis, G. R., Whitfield, K. M., Chappelle, H. L., DiMichele, L. J., and Gingeras, T. R. (1989) *Proc. Natl. Acad. Sci. U.S.A* 86, 1173–1177.
21. Kwok, S., Kellogg, D. E., McKinney, N., Spasic, D., Goda, L., Levenson, C., and Sninsky, J. J. (1990) *Nucleic Acids Res* 18, 999–1005.
22. Landegren, U., Kaiser, R., Sanders, J., and Hood, L. (1988) *Science* 241, 1077–1080.
23. Lizardi, P. M., Guerra, C. E., Lomeli, H., Tussie-Luna, I., and Kramer, F. R. (1988) *Biotechnology* 6, 1197–1202.
24. Lizardi, P. M., Huang, X., Zhu, Z., Bray-Ward, P., Thomas, D. C., and Ward, D. C. (1998) *Nat Genet* 19, 225–232.
25. Lomeli, H., Tyagi, S., Pritchard, C. G., Lizardi, P. M., and Kramer, F. R. (1989) *Clin. Chem* 35, 1826–1831.
26. Machida, A., Ohnuma, H., Tsuda, F., Munekata, E., Tanaka, T., Akahane, Y., Okamoto, H., and Mishiro, S. (1992) *Hepatology* 16, 886–891.
27. Maertens, G., Duccateeuw, A., Stuyver, L., Vandeponseele, P., Venneman, A., Wyseur, A., Bosman, F., Heijtink, R., and de Martynoff, G. (1994) in *Viral Hepatitis and Liver Disease. Proceedings of the International Symposium on Viral Hepatitis and Liver Disease* (Nishioka, K., Suzuki, H., Mishiro, S., and Oda, T., Eds.) pp 314–316, Springer Verlag, Tokyo.
28. Maertens, G. and Stuyver, L. (1997) in *The molecular medicine of viral hepatitis* (Harrison, T. J. and Zuckerman, A. J., Eds.) pp 183–233, John Wiley & Sons.
29. Matsukura, M., Shinozuka, K., Zon, G., Mitsuya, H., Reitz, M., Cohen, J. S., and Broder, S. (1987) *Proc. Natl. Acad. Sci. U.S.A* 84, 7706–7710.
30. Miller, P. S., Yano, J., Yano, E., Carroll, C., Jayaraman, K., and Ts'o, P. O. (1979) *Biochemistry* 18, 5134–5143.
31. Mori, S., Kato, N., Yagyu, A., Tanaka, T., Ikeda, Y., Petchclai, B., Chiewsilp, P., Kurimura, T., and Shimotohno, K. (1992) *Biochem Biophys Res Commun.* 183, 334–342.
32. Myers, T. W. and Gelfand, D. H. (1991) *Biochemistry* 30, 7661–7666.
33. Nielsen, P. E., Egholm, M., Berg, R. H., and Buchardt, O. (1991) *Science* 254, 1497–1500.
34. Nielsen, P. E., Egholm, M., Berg, R. H., and Buchardt, 0. (1993) *Nucleic Acids Res.* 21, 197–200.
35. Nielsen, P. E. (2001) *Curr Med Chem* 8, 545–550.
36. Okamoto, H., Okada, S., Sugiyama, Y., Kurai, K., lizuka, H., Machida, A., Miyakawa, Y., and Mayumi, M. (1991) *J. Gen Virol.* 72 (Pt 11), 2697–2704.
37. Okamoto, H., Kurai, K., Okada, S., Yamamoto, K., Lizuka, H., Tanaka, T., Fukuda, S., Tsuda, F., and Mishiro, S. (1992) *Virology* 188, 331–341.
38. Orum, H. and Wengel, J. (2001) *Curr Opin. Mol. Ther.* 3, 239–243.
39. Persson, M. A., Caothien, R. H., and Burton, D. R. (1991) *Proc. Natl. Acad. Sci. U.S.A* 88, 2432–2436.
40. Robertson, B., Myers, G., Howard, C., Brettin, T., Bukh, J., Gaschen, B., Gojobori, T., Maertens, G., Mizokami, M., Nainan, O., Netesov, S., Nishioka, K., Shin i T, Simmonds, P., Smith, D., Stuyver, L., and Weiner, A. (1998) *Arch Virol.* 143, 2493–2503.
41. Saiki, R. K., Gelfand, D. H., Stoffel, S., Scharf, S. J., Higuchi, R., Horn, G. T., Mullis, K. B., and Erlich, H. A. (1988) *Science* 239, 487–491.
42. Saiki, R. K., Walsh, P. S., Levenson, C. H., and Erlich, H. A. (1989) *Proc Natl Acad Sci USA* 86, 6230–6234.
43. Sambrook, J., Fritsch, E. F., and Maniatis, T. (1989) *Molecular Cloning: A Laboratory Manual* Cold Spring Harbor Laboratory Press.
44. Sano, T., Smith, C. L., and Cantor, C. R. (1992) *Science* 258, 120–122.
45. Simmonds, P., Holmes, E. C., Cha, T. A., Chan, S. W., McOmish, F., Irvine, B., Beall, E., Yap, P. L., Kolberg, J., and Urdea, M. S. (1993) *J. Gen Virol.* 74 (Pt 11), 2391–2399.
46. Simmonds, P., McOmish, F., Yap, P. L., Chan, S. W., Lin, C. K., Dusheiko, G., Saeed, A. A., and Holmes, E. C. (1993) *J. Gen Virol.* 74 (Pt 4), 661–668.
47. Simmonds, P., Alberti, A., Alter, H. J., Bonino, F., Bradley, D. W., Brechot, C., Brouwer, J. T., Chan, S. W., Chayama, K., Chen, D. S., and. (1994) *Hepatology* 19, 1321–1324.
48. Stary, A., Schuh, E., Kerschbaumer, M., Gotz, B., and Lee, H. (1998) *J Clin Microbiol* 36, 2666–2670.
49. Stuyver, L., Rossau, R., Wyseur, A., Duhamel, M., Vanderborght, B., Van Heuverswyn, H., and Maertens, G. (1993) *J. Gen Virol.* 74 (Pt 6), 1093–1102.
50. Stuyver, L., van Arnhem, W., Wyseur, A., DeLeys, R., and Maertens, G. (1993) *Biochem Biophys Res. Commun.* 192, 635–641.
51. Stuyver, L., van Arnhem, W., Wyseur, A., Hernandez, F., Delaporte, E., and Maertens, G. (1994) *Proc. Natl. Acad. Sci. U.S.A* 91, 10134–10138.
52. Stuyver, L., van Arnhem, W., Wyseur, A., and Maertens, G. (1994) *Biochem Biophys Res Commun.* 202, 1308–1314.
53. Stuyver, L., Wyseur, A., van Arnhem, W., Rossau, R., Delaporte, E., Dazza, M.-C., Van Doorn, L.-J., Kleter, B., and Maertens, G. (1994) in *Viral Hepatitis and Liver Disease. Proceedings of the International Symposium on Viral Hepatitis and Liver Disease* (Nishioka, K., Suzuki, H., Mishiro, S., and Oda, S., Eds.) pp 317–319, Springer Verlag, Tokyo.
54. Stuyver, L., Wyseur, A., van Arnhem, W., Hernandez, F., and Maertens, G. (1996) *J Clin Microbiol* 34, 2259–2266.
55. Wahlestedt, C., Salmi, P., Good, L., Kela, J., Johnsson, T., Hokfelt, T., Broberger, C., Porreca, F., Lai, J., Ren, K., Ossipov, M., Koshkin, A., Jakobsen, N., Skouv, J., Oerum, H., Jacobsen, M. H., and Wengel, J. (2000) *Proc Natl Acad Sci USA* 97, 5633–5638.
56. Walker, G. T., Little, M. C., Nadeau, J. G., and Shank, D. D. (1992) *Proc Natl Acad Sci USA* 89, 392–396.

57. Wu, D. Y. and Wallace, R. B. (1989) *Genomics* 4, 560–569.
58. Altschul, S. F., Gish, W., Miller, W., Myers, E. W., and Lipman, D. J. (1990) *J. Mol Biol.* 215, 403–410.
59. Altschul, S. F. (1991) *J. Mol Biol.* 219, 555–565.
60. Arguello, J. R., Little, A. M., Pay, A. L., Gallardo, D., Rojas, I., Marsh, S. G., Goldman, J. M., and Madrigal, J. A. (1998) *Nat. Genet* 18, 192–194.
61. Baner, J., Nilsson, M., Mendel-Hartvig, M., and Landegren, U. (1998) *Nucleic Acids Res* 26, 5073–5078.
62. Bazar, L. S., Collier, G. B., Vanek, P. G., Siles, B. A., Kow, Y. W., Doetsch, P. W., Cunningham, R. P., and Chirikjian, J. G. (1999) *Electrophoresis* 20, 1141–1148.
63. Beaucage, S. L. (2001) *Curr. Med. Chem* 8, 1213–1244.
64. Beaudet, L., Bedard, J., Breton, B., Mercuri, R. J., and Budarf, M. L. (2001) *Genome Res* 11, 600–608.
65. Bernard, P. S., Reiser, A., and Pritham, G. H. (2001) in *Rapid Cycle Real-Time PCR. Methods and Applications* (Meuer, S., Wittwer, C., and Nakagawara, K., Eds.) pp 11–19, Springer Verlag, Berlin Heidelberg New York.
66. Bosserhoff, A. K., Seegers, S., Hellerbrand, C., Scholmerich, J., and Buttner, R. (1999) *Biotechniques* 26, 1106–1110.
67. Bray, M. S., Boerwinkle, E., and Doris, P. A. (2001) *Hum. Mutat.* 17, 296–304.
68. Brow, M. A., Oldenburg, M. C., Lyamichev, V., Heisler, L. M., Lyamicheva, N., Hall, J. G., Eagan, N. J., Olive, D. M., Smith, L. M., Fors, L., and Dahlberg, J. E. (1996) *J Clin Microbiol* 34, 3129–3137.
69. Cairns, M. J., King, A., and Sun, L. Q. (2000) *Nucleic Acids Res* 28, E9.
70. Cha, R. S., Zarbl, H., Keohavong, P., and Thilly, W. G. (1992) *PCR Methods Appl* 2, 14–20.
71. Chen, X. and Kwok, P. Y. (1997) *Nucleic Acids Res* 25, 347–353.
72. Chen, X., Livak, K. J., and Kwok, P. Y. (1998) *Genome Res* 8, 549–556.
73. Church, G. M. and Gilbert, W. (1984) *Proc Natl Acad Sci USA* 81, 1991–1995.
74. Cronin, M. T., Fucini, R. V., Kim, S. M., Masino, R. S., Wespi, R. M., and Miyada, C. G. (1996) *Hum Mutat* 7, 244–255.
75. Day, I. N., Spanakis, E., Palamand, D., Weavind, G. P., and O'Dell, S. D. (1998) *Trends. Biotechnol* 16, 287–290.
76. De Francesco, L. (1998) *The Scientist* 12, 16.
77. Del Tito B J, J., Poff, H. E., Novotny, M. A., Cartledge, D. M., Walker, R. I., Earl, C. D., and Bailey, A. L. (1998) *Clin Chem* 44, 731–739.
78. Delwart, E. L., Shpaer, E. G., Louwagie, J., McCutchan, F. E., Grez, M., Rubsamen-Waigmann, H., and Mullins, J. I. (1993) *Science* 262, 1257–1261.
79. Delwart, E. L., Sheppard, H. W., Walker, B. D., Goudsmit, J., and Mullins, J. I. (1994) *J Virol* 68, 6672–6683.
80. Drmanac, R., Drmanac, S., Strezoska, Z., Paunesku, T., Labat, I., Zeremski, M., Snoddy, J., Funkhouser, W. K., Koop, B., and Hood, L. (1993) *Science* 260, 1649–1652.
81. Dubertret, B., Calame, M., and Libchaber, A. J. (2001) *Nat Biotechnol.* 19, 365–370.
82. Eis, P. S., Olson, M. C., Takova, T., Curtis, M. L., Olson, S. M., Vener, T. I., Ip, H. S., Vedvik, K. L., Bartholomay, C. T., Allawi, H. T., Ma, W. P., Hall, J. G., Morin, M. D., Rushmore, T. H., Lyamichev, V. I., and Kwiatkowski, R. W. (2001) *Nat Biotechnol.* 19, 673–676.
83. Faruqi, A. F., Hosono, S., Driscoll, M. D., Dean, F. B., Alsmadi, O., Bandaru, R., Kumar, G., Grimwade, B., Zong, Q., Sun, Z., Du, Y., Kingsmore, S., Knott, T., and Lasken, R. S. (2001) *BMC. Genomics* 2, 4.
84. Faudoa, R., Xue, Z., Lee, F., Baser, M. E., and Hung, G. (2000) *Hum Mutat* 15, 474–478.
85. Ganguly, T., Dhulipala, R., Godmilow, L., and Ganguly, A. (1998) *Hum Genet* 102, 549–556.
86. Goldrick, M. M., Kimball, G. R., Liu, Q., Martin, L. A., Sommer, S. S., and Tseng, J. Y. (1996) *Biotechniques* 21, 106–112.
87. Grange, D. K., Gottesman, G. S., Lewis, M. B., and Marini, J. C. (1990) *Nucleic Acids Res* 18, 4227–4236.
88. Griffin, T. J., Hall, J. G., Prudent, J. R., and Smith, L. M. (1999) *Proc Natl Acad Sci USA* 96, 6301–6306.
89. Griffin, T. J. and Smith, L. M. (2000) *Trends. Biotechnol.* 18, 77–84.
90. Hacia, J. G., Brody, L. C., Chee, M. S., Fodor, S. P., and Collins, F. S. (1996) *Nat Genet* 14, 441–447.
91. Hall, J. G., Eis, P. S., Law, S. M., Reynaldo, L. P., Prudent, J. R., Marshall, D. J., Allawi, H. T., Mast, A. L., Dahlberg, J. E., Kwiatkowski, R. W., de Arruda, M., Neri, B. P., and Lyamichev, V. I. (2000) *Proc Natl Acad Sci U S A* 97, 8272–8277.
92. Hawkins, G. A. and Hoffman, L. M. (1999) *Electrophoresis* 20, 1171–1176.
93. Healey, B. G., Matson, R. S., and Walt, D. R. (1997) *Anal. Biochem* 251, 270–279.
94. Howell, W. M., Jobs, M., Gyllensten, U., and Brookes, A. J. (1999) *Nat Biotechnol.* 17, 87–88.
95. Huber, C. G., Premstaller, A., Xiao, W., Oberacher, H., Bonn, G. K., and Oefner, P. J. (2001) *J Biochem Biophys Methods* 47, 5–19.
96. Iwahana, H., Fujimura, M., Takahashi, Y., Iwabuchi, T., Yoshimoto, K., and Itakura, M. (1996) *Biotechniques* 21, 510–519.
97. James, W. and al-Shamkhani, A. (1995) *Curr Opin. Biotechnol.* 6, 44–49.
98. Kenney, M., Ray, S., and Boles, T. C. (1998) *Biotechniques* 25, 516–521.
99. Khanna, M., Park, P., Zirvi, M., Cao, W., Picon, A., Day, J., Paty, P., and Barany, F. (1999) *Oncogene* 18, 27–38.
100. Khrapko, K., Hanekamp, J. S., Thilly, W. G., Belenkii, A., Foret, F., and Karger, B. L. (1994) *Nucleic Acids Res* 22, 364–369.
101. Khrapko, K., Coller, H., Andre, P., Li, X. C., Foret, F., Belenky, A., Karger, B. L., and Thilly, W. G. (1997) *Nucleic Acids Res* 25, 685–693.
102. Khrapko, K., Coller, H. A., Li-Sucholeiki, X. C., Andre, P. C., and Thilly, W. G. (2001) *Methods Mol. Biol* 163, 57–72.
103. Korkko, J., Annunen, S., Pihlajamaa, T., Prockop, D. J., and Ala-Kokko, L. (1998) *Proc Natl Acad Sci USA* 95, 1681–1685.
104. Kristensen, V. N., Keleflotis, D., Kristensen, T., and Borresen-Dale, A. L. (2001) *Biotechniques* 30, 318–22, 324, 326.
105. Langemeier, J. L., Cook, R. F., Issel, C. J., and Montelaro, R. C. (1994) *Biotechniques* 17, 484–6, 488, 490.
106. Ledford, M., Friedman, K. D., Hessner, M. J., Moehlenkamp, C., Williams, T. M., and Larson, R. S. (2000) *J Mol. Diagn.* 2, 97–104.

107. Li-Sucholeiki, X. C. and Thilly, W. G. (2000) *Nucleic Acids Res* 28, E44.
108. Liu, Q., Feng, J., and Sommer, S. S. (1996) *Hum Mol. Genet* 5, 107–114.
109. Liu, Q., Weinshenker, B. G., Wingerchuk, D. M., and Sommer, S. S. (1998) *Biotechniques* 24, 140–147.
110. Luo, J., Bergstrom, D. E., and Barany, F. (1996) *Nucleic Acids Res* 24, 3071–3078.
111. Lyamichev, V., Mast, A. L., Hall, J. G., Prudent, J. R., Kaiser, M. W., Takova, T., Kwiatkowski, R. W., Sander, T. J., de Arruda, M., Arco, D. A., Neri, B. P., and Brow, M. A. (1999) *Nat Biotechnol.* 17, 292–296.
112. Maxam, A. M. and Gilbert, W. (1977) *Proc Natl Acad Sci USA* 74, 560–564.
113. Mein, C. A., Barratt, B. J., Dunn, M. G., Siegmund, T., Smith, A. N., Esposito, L., Nutland, S., Stevens, H. E., Wilson, A. J., Phillips, M. S., Jarvis, N., Law, S., de Arruda, M., and Todd, J. A. (2000) *Genome Res* 10, 330–343.
114. Meller, A., Nivon, L., Brandin, E., Golovchenko, J., and Branton, D. (2000) *Proc Natl Acad Sci USA* 97, 1079–1084.
115. Murakami, A., Nakaura, M., Nakatsuji, Y., Nagahara, S., Tran-Cong, Q., and Makino, K. (1991) *Nucleic Acids Res* 19, 4097–4102.
116. Myakishev, M. V., Khripin, Y., Hu, S., and Hamer, D. H. (2001) *Genome Res* 11, 163–169.
117. Myers, R. M., Fischer, S. G., Lerman, L. S., and Maniatis, T. (1985) *Nucleic Acids Res* 13, 3131–3145.
118. Myers, R. M., Larin, Z., and Maniatis, T. (1985) *Science* 230, 1242–1246.
119. Narayanaswarni, G. and Taylor, P. D. (2001) *Genet Test.* 5, 9–16.
120. Nazarenko, I. A., Bhatnagar, S. K., and Hohman, R. J. (1997) *Nucleic Acids Res* 25, 2516–2521.
121. Nikiforov, T. T., Rendle, R. B., Goelet, P., Rogers, Y. H., Kotewicz, M. L., Anderson, S., Trainor, G. L., and Knapp, M. R. (1994) *Nucleic Acids Res* 22, 4167–4175.
122. Nilsson, M., Malmgren, H., Samiotaki, M., Kwiatkowski, M., Chowdhary, B. P., and Landegren, U. (1994) *Science* 265, 2085–2088.
123. Nishimura, A. and Tsuhako, M. (2000) *Chem Pharm. Bull.* (Tokyo.) 48, 774–778.
124. Pastinen, T., Partanen, J., and Syvanen, A. C. (1996) *Clin Chem* 42, 1391–1397.
125. Pastinen, T., Kurg, A., Metspalu, A., Peltonen, L., and Syvanen, A. C. (1997) *Genome Res* 7, 606–614.
126. Pastinen, T., Raitio, M., Lindroos, K., Tainola, P., Peltonen, L., and Syvanen, A. C. (2000) *Genome Res* 10, 1031–1042.
127. Patolsky, F., Lichtenstein, A., and Willner, I. (2001) *Nat Biotechnol.* 19, 253–257.
128. Prince, J. A., Feuk, L., Howell, W. M., Jobs, M., Emahazion, T., Blennow, K., and Brookes, A. J. (2001) *Genome Res* 11, 152–162.
129. Resch, W., Parkin, N., Stuelke, E. L., Watkins, T., and Swanstrom, R. (2001) *Proc Natl Acad Sci USA* 98, 176–181.
130. Righetti, P. G. and Gelfi, C. (1997) *Electrophoresis* 18, 1709–1714.
131. Ronaghi, M., Uhlen, M., and Nyren, P. (1998) *Science* 281, 363, 365.
132. Rowley, G., Saad, S., Giannelli, F., and Green, P. M. (1995) *Genomics* 30, 574–582.
133. Ruano, G. and Kidd, K. K. (1991) *Proc Natl Acad Sci USA* 88, 2815–2819.
134. Runnels, L. W. and Scarlata, S. F. (1995) *Biophys J* 69, 1569–1583.
135. Ryan, D., Nuccie, B., and Arvan, D. (1999) *Mol. Diagn.* 4, 135–144.
136. Sanger, F., Nicklen, S., and Coulson, A. R. (1977) *Proc Natl Acad Sci USA* 74, 5463–5467.
137. Sapolsky, R. J., Hsie, L., Berno, A., Ghandour, G., Mittmann, M., and Fan, J. B. (1999) *Genet Anal.* 14, 187–192.
138. Sarkar, G., Yoon, H. S., and Sommer, S. S. (1992) *Genomics* 13, 441–443.
139. Schumm, J. W., Knowlton, R. G., Braman, J. C., Barker, D. F., Botstein, D., Akots, G., Brown, V. A., Gravius, T. C., Helms, C., and Hsiao, K. (1988) *Am. J Hum Genet* 42, 143–159.
140. Sheffield, V. C., Cox, D. R., Lerman, L. S., and Myers, R. M. (1989) *Proc Natl Acad Sci USA* 86, 232–236.
141. Smith, R. D., Cheng, X., Bruce, J. E., Hofstadler, S. A., and Anderson, G. A. (1994) *Nature* 369, 137–139.
142. Sreevatsan, S., Bookout, J. B., Ringpis, F. M., Pottathil, M. R., Marshall, D. J., de Arruda, M., Murvine, C., Fors, L., Pottathil, R. M., and Barathur, R. R. (1998) *J Clin Microbiol* 36, 1895–1901.
143. States, D. J., Gish, W., and Altschul, S. F. (1991) *Methods* 3, 66–70.
144. Taylor, G. R. (1999) *Electrophoresis* 20, 1125–1130.
145. Tyagi, S. and Kramer, F. R. (1996) *Nat Biotechnol.* 14, 303–308.
146. Tyagi, S., Bratu, D. P., and Kramer, F. R. (1998) *Nat Biotechnol.* 16, 49–53.
147. Vijg, J. and van Orsouw, N. J. (1999) *Electrophoresis* 20, 1239–1249.
148. Vos, P., Hogers, R., Bleeker, M., Reijans, M., van de Lee, T., Hornes, M., Frijters, A., Pot, J., Peleman, J., and Kuiper, M. (1995) *Nucleic Acids Res* 23, 4407–4414.
149. Whitcombe, D., Theaker, J., Guy, S. P., Brown, T., and Little, S. (1999) *Nat Biotechnol.* 17, 804–807.
150. Wittwer, C. (2001) in *Rapid Cycle Real-Time PCR. Methods and Applications.* (Meuer, S., Wittwer, C., and Nakagawara, K., Eds.) pp 1–8, Springer Verlag, Berlin Heidelberg New York.
151. Wu, D. Y., Ugozzoli, L., Pal, B. K., and Wallace, R. B. (1989) *Proc Natl Acad Sci U S A* 86, 2757–2760.
152. Xiao, W. and Oefner, P. J. (2001) *Hum Mutat* 17, 439–474.
153. Yager, T. D., Baron, L., Batra, R., Bouevitch, A., Chan, D., Chan, K., Darasch, S., Gilchrist, R., Izmailov, A., Lacroix, J. M., Marchelleta, K., Renfrew, J., Rushlow, D., Steinbach, E., Ton, C., Waterhouse, P., Zaleski, H., Dunn, J. M., and Stevens, J. (1999) *Electrophoresis* 20, 1280–1300.
154. Zhang, D. Y., Brandwein, M., Hsuih, T. C., and Li, H. (1998) *Gene* 211, 277–285.
155. Nakao, T., Enomoto, N., Takada, N., Takada, A., and Date, T. (1991) *J. Gen Virol.* 72 (Pt 9), 2105–2112.

The contents of all references cited herein are incorporated in their entirety by reference.

The invention claimed is:

1. An isolated HCV polynucleic acid of a clade 6 type 13 HCV genotype, said polynucleic acid characterized in that it is comprising
 (i) a 5' UTR nucleic acid sequence defined by SEQ ID NO:1, or
 (ii) the complement of the nucleic acid sequence of (i); and wherein said polynucleic acid is RNA, DNA, cDNA or a synthetic polynucleic acid.

2. An isolated oligonucleotide comprising at least 65 contiguous nucleotides taken from the HCV polynucleic acid defined by SEQ ID NO:1 or the complement thereof, and comprising, relative to the start codon of the HCV polyprotein coding sequence, an adenine nucleotide at position −159.

3. An isolated oligonucleotide consisting of at least 65 contiguous nucleotides taken from the HCV polynucleic acid defined by SEQ ID NO:1 or the complement thereof, and comprising, relative to the start codon of the HCV polyprotein coding sequence, an adenine nucleotide at position −159.

4. The isolated oligonucleotide according to claim 2 which is a primer capable of specifically amplifying a HCV polynucleic acid.

5. The isolated oligonucleotide according to claim 2 which is a probe capable of specifically hybridizing to a HCV polynucleic acid.

6. The isolated oligonucleotide according to claim 2 which is capable of specifically detecting a HCV polynucleic acid.

7. The isolated oligonucleotide according to claim 2 which is capable of determining the genotype of a HCV polynucleic acid.

8. The isolated oligonucleotide according to claim 2 comprising besides deoxyribonucleic acid monomers either one or more of:
 a modified nucleotide base,
 a labeled nucleotide,
 a modified polynucleotide backbone,
 a peptide nucleic acid monomer,
 a locked nucleic acid monomer, and/or
 a ribonucleic acid monomer.

9. A recombinant vector comprising a HCV polynucleic acid according to claim 1.

10. The vector according to claim 9 which is an expression vector capable of driving expression of a HCV peptide encoded by the HCV polynucleic acid comprised in said vector.

11. An isolated host cell containing the HCV polynucleic acid according to claim 1 or transformed with a vector containing said HCV polynucleic acid.

12. A method for production of the recombinant polypeptide comprising:
 transformation of an appropriate cellular host with a recombinant vector according to claim 9,
 culturing said transformed cellular host under conditions enabling the expression of said insert, and,
 harvesting said polypeptide.

13. A method for detecting the presence of a HCV virus in a biological sample comprising the step of detecting the presence of a polynucleic acid according to claim 1.

14. The method according to claim 13 comprising the steps of:
 (i) obtaining a target HCV polynucleic acid from a biological sample suspected to contain a HCV polynucleic acid or fragment thereof;
 (ii) obtaining the nucleic acid sequence of the target HCV polynucleic acid of (i);
 (iii) infering, from the nucleic acid sequence obtained in (ii), the presence of a HCV polynucleic acid or fragment thereof and, therefrom, the presence of a HCV virus in said biological sample.

15. The method according to claim 13 comprising the steps of:
 (i) obtaining a target HCV polynucleic acid from a biological sample suspected to contain a HCV polynucleic acid or fragment thereof;
 (ii) contacting the target HCV polynucleic acid of (i) with an oligonucleotide capable of discriminating at least one genotype-specific nucleotide present in said target HCV polynucleic acid, and said contacting generating a discriminatory signal;
 (iii) infering, from the discriminatory signal obtained in (ii), the presence of a HCV polynucleic acid or fragment thereof and, therefrom, the presence of a HCV virus in said biological sample.

16. A method for determining the genotype of a HCV virus present in a biological sample comprising the step of detecting the presence of a HCV polynucleic acid according to claim 1.

17. The method according to claim 16 comprising the steps of:
 (i) obtaining a target HCV polynucleic acid from a biological sample suspected to contain a HCV polynucleic acid or fragment thereof;

(ii) obtaining the nucleic acid sequence of the target HCV polynucleic acid of (i);
(iii) infering, from the nucleic acid sequence obtained in (ii), the presence of a HCV polynucleic acid or fragment thereof and, therefrom, the genotype of said HCV virus present in said biological sample.

18. The method according to claim 16 comprising the steps of:
(i) obtaining a target HCV polynucleic acid from a biological sample suspected to contain a HCV polynucleic acid or fragment thereof;
(ii) contacting the target HCV polynucleic acid of (i) with an oligonucleotide capable of discriminating at least one genotype-specific nucleotide present in said target HCV polynucleic acid, and said contacting generating a discriminatory signal;
(iii) infering, from the discriminatory signal obtained in (ii), the presence of a HCV polynucleic acid or fragment thereof and, therefrom, the genotype of said HCV virus present in said biological sample.

19. The method according to claim 13 which is based on an amplification reaction, a hybridization reaction, a reverse hybridization reaction or a sequencing reaction.

20. The method according to claim 13 comprising:
amplification of the polynucleic acid or fragment thereof with an oligonucleotide;
hybridization of the polynucleic acid or fragment thereof with an oligonucleotide; or
detection of the polynucleic acid or fragment thereof with an oligonucleotide.

21. The method according to claim 16 comprising determination of the genotype of the polynucleic acid or fragment thereof.

22. A diagnostic kit for detecting the presence of a HCV virus in a biological sample, said kit comprising an oligonucleotide according to claim 4.

23. A diagnostic kit for determining the genotype of a HCV virus present in a biological sample, said kit comprising an oligonucleotide according to claim 4.

24. The diagnostic kit according to claim 22 wherein said oligonucleotide is attached to a solid support.

25. The diagnostic kit according to claim 24 wherein a range of oligonucleotides are attached to specific locations on the solid support.

26. The diagnostic kit according to claim 25 wherein said solid support is a membrane strip and wherein said oligonucleotides are probes coupled to the membrane in the form of parallel lines.

27. A diagnostic kit for determining the presence and/or for determining the genotype of a HCV virus in a biological sample, said kit comprising:
(i) a means for obtaining the nucleic acid sequence of a target HCV polynucleic acid from a biological sample suspected to contain HCV polynucleic acid according to claim 1;
(ii) a means for infering, from the nucleic acid sequence obtained from the target HCV polynucleic acid, the presence of a polynucleic acid sequence unique to a HCV polynucleic acid and, therefrom, the presence in said biological sample of a HCV and/or the genotype of said HCV.

* * * * *